(12) United States Patent
Allen et al.

(10) Patent No.: US 8,951,235 B2
(45) Date of Patent: *Feb. 10, 2015

(54) SYSTEMS AND METHODS FOR CONTROLLING OPERATION OF A REDUCED PRESSURE THERAPY SYSTEM

(75) Inventors: Julie Allen, Hull (GB); Ben Alan Askem, Brough (GB); Sarah Jenny Collinson, Hull (GB); Richard Thomas Hughey, Dallas, TX (US); Derek Nicolini, South Cave (GB)

(73) Assignee: Smith & Nephew PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/403,715

(22) Filed: Feb. 23, 2012

(65) Prior Publication Data

US 2012/0165764 A1 Jun. 28, 2012

Related U.S. Application Data

(63) Continuation of application No. 13/287,959, filed on Nov. 2, 2011, and a continuation-in-part of application No. PCT/GB2011/051745, filed on Sep. 16, 2011.

(60) Provisional application No. 61/511,950, filed on Jul. 26, 2011.

(30) Foreign Application Priority Data

Sep. 20, 2010 (GB) .................................. 1015656.0

(51) Int. Cl.
*A61M 1/00* (2006.01)
*A61M 31/00* (2006.01)
*A61M 5/168* (2006.01)

(52) U.S. Cl.
CPC ........... *A61M 1/0037* (2013.01); *A61M 1/0031* (2013.01); *A61M 1/0088* (2013.01);
(Continued)

(58) Field of Classification Search
CPC ............ A61M 1/0031; A61M 1/0088; A61M 2205/15; A61M 2205/18; A61M 2205/8212

USPC .......................... 604/318, 319, 320, 323, 500
See application file for complete search history.

(56) References Cited

U.S. PATENT DOCUMENTS

| 4,062,012 A | 12/1977 | Colbert et al. |
| 4,643,641 A | 2/1987 | Clausen et al. |

(Continued)

FOREIGN PATENT DOCUMENTS

| WO | WO 98/19068 | 5/1998 |
| WO | WO 03/057307 A1 | 7/2003 |

(Continued)

OTHER PUBLICATIONS

U.S. Appl. No. 13/824,982, filed Mar. 18, 2013, and its ongoing prosecution history, including without limitation Office Actions, Amendments, Remarks, and any other potentially relevant documents, Derek Nicolini.

(Continued)

*Primary Examiner* — Tatyana Zalukaeva
*Assistant Examiner* — Andrew J Mensh
(74) *Attorney, Agent, or Firm* — Knobbe, Martens, Olson & Bear, LLP

(57) ABSTRACT

Negative pressure wound therapy apparatuses and dressings, and systems and methods for operating such apparatuses for use with dressings are disclosed. In some embodiments, controlling the delivery of therapy can be based on monitoring and detecting various operating conditions. An apparatus can have a controller configured to monitor the duty cycle of a source of negative pressure and, based on the monitored duty cycle, determine whether a leak is present. The controller can be configured to provide an indication that a leak is present. For example, the controller can be configured to suspend and/or pause the delivery of therapy, and to restart the delivery of therapy due to a timeout, request from a user, etc. In addition, the controller can be configured to pause and/or restart the delivery of therapy upon a request from the user, such as in response to the user operating a switch.

21 Claims, 55 Drawing Sheets

(52) U.S. Cl.
CPC ........ *A61M2205/18* (2013.01); *A61M 5/16831* (2013.01); *A61M 2205/15* (2013.01); *A61M 2205/3344* (2013.01); *A61M 2205/8212* (2013.01)
USPC ........... 604/319; 604/318; 604/320; 604/323; 604/500

(56) References Cited

U.S. PATENT DOCUMENTS

| | | | |
|---|---|---|---|
| 4,969,880 | A | 11/1990 | Zamierowski |
| 5,127,388 | A | 7/1992 | Cicalese et al. |
| 5,616,121 | A * | 4/1997 | McKay ............................ 604/35 |
| 7,524,315 | B2 | 4/2009 | Blott et al. |
| 7,708,724 | B2 | 5/2010 | Weston |
| 7,909,805 | B2 | 3/2011 | Weston |
| 7,964,766 | B2 | 6/2011 | Blott et al. |
| 8,062,272 | B2 | 11/2011 | Weston |
| 8,080,702 | B2 | 12/2011 | Blott et al. |
| 8,105,295 | B2 | 1/2012 | Blott et al. |
| 8,282,611 | B2 | 10/2012 | Weston |
| 8,303,552 | B2 | 11/2012 | Weston |
| 8,398,614 | B2 | 3/2013 | Blott et al. |
| D679,819 | S | 4/2013 | Peron |
| D679,820 | S | 4/2013 | Peron |
| 8,449,509 | B2 | 5/2013 | Weston |
| 2002/0171553 | A1 | 11/2002 | Omry et al. |
| 2002/0198504 | A1* | 12/2002 | Risk et al. ..................... 604/318 |
| 2003/0014022 | A1 | 1/2003 | Lockwood et al. |
| 2005/0267402 | A1 | 12/2005 | Stewart et al. |
| 2006/0025727 | A1 | 2/2006 | Boehringer et al. |
| 2006/0083623 | A1 | 4/2006 | Higgins et al. |
| 2006/0282175 | A1* | 12/2006 | Haines et al. ................... 623/24 |
| 2007/0032762 | A1 | 2/2007 | Vogel |
| 2007/0113849 | A1 | 5/2007 | Matthews et al. |
| 2007/0219532 | A1 | 9/2007 | Karpowicz et al. |
| 2008/0200857 | A1 | 8/2008 | Lawhorn |
| 2009/0012441 | A1 | 1/2009 | Mulligan |
| 2009/0123513 | A1 | 5/2009 | Greener |
| 2009/0125004 | A1 | 5/2009 | Shen et al. |
| 2009/0270833 | A1* | 10/2009 | DeBelser et al. ............. 604/500 |
| 2009/0292264 | A1 | 11/2009 | Hudspeth et al. |
| 2010/0036367 | A1 | 2/2010 | Krohn |
| 2010/0126484 | A1 | 5/2010 | Skell et al. |
| 2010/0160880 | A1 | 6/2010 | Weston |
| 2010/0249733 | A9 | 9/2010 | Blott |
| 2010/0274207 | A1 | 10/2010 | Weston |
| 2011/0009838 | A1 | 1/2011 | Greener |
| 2011/0028918 | A1 | 2/2011 | Hartwell |
| 2011/0054421 | A1 | 3/2011 | Hartwell |
| 2011/0054423 | A1 | 3/2011 | Blott et al. |
| 2011/0060284 | A1 | 3/2011 | Harr |
| 2011/0077605 | A1 | 3/2011 | Karpowicz et al. |
| 2011/0118683 | A1 | 5/2011 | Weston |
| 2011/0202220 | A1* | 8/2011 | Seta et al. ........................ 701/22 |
| 2011/0257572 | A1 | 10/2011 | Locke et al. |
| 2011/0282309 | A1* | 11/2011 | Adie et al. .................... 604/319 |
| 2012/0130325 | A1* | 5/2012 | Blott et al. .................... 604/319 |
| 2012/0136325 | A1 | 5/2012 | Allen et al. |
| 2013/0110058 | A1 | 5/2013 | Adie et al. |

FOREIGN PATENT DOCUMENTS

| | | |
|---|---|---|
| WO | WO 2006/046060 A2 | 5/2006 |
| WO | WO 2007/087811 A1 | 8/2007 |
| WO | WO 2008/048481 | 4/2008 |
| WO | WO 2008/100440 A1 | 8/2008 |
| WO | WO 2008/135997 A2 | 11/2008 |
| WO | WO 2009/019415 A2 | 2/2009 |
| WO | WO 2009/047524 A2 | 4/2009 |
| WO | WO 2009/089390 A2 | 7/2009 |
| WO | WO 2010/039481 A1 | 4/2010 |
| WO | WO 2010/051418 | 7/2010 |
| WO | WO 2010/093753 A1 | 8/2010 |
| WO | WO 2010/126444 A1 | 11/2010 |
| WO | WO 2011/087871 A2 | 7/2011 |
| WO | WO 2012/038724 | 3/2012 |

OTHER PUBLICATIONS

International Search Report in PCT/GB2011/051745 mailed on Feb. 2, 2012 in 5 pages.

International Preliminary Report on Patentability in PCT/GB2011/051745 issued on Mar. 26, 2013 in 7 pages.

International Search Report in PCT/IB2011/002943 mailed on Jan. 28, 2013 in 9 pages.

International Search Report and Written Opinion for International Application No. PCT/US2011/059016 mailed on Apr. 23, 2014 in 18 pages.

Invitation to Pay Additional Fees for International Application No. PCT/US2011/059016 mailed on Feb. 17, 2014 in 7 pages.

International Search Report for PCT Application No. PCT/GB2011/051745, mailed Feb. 2, 2012 in 5 pages.

International Preliminary Report on Patentability issued on Mar. 26, 2013 in International Application No. PCT/GB2011/051745 in 7 pages.

Office Action issued on Aug. 15, 2013 in U.S. Appl. No. 13/824,982 in 14 pages.

* cited by examiner

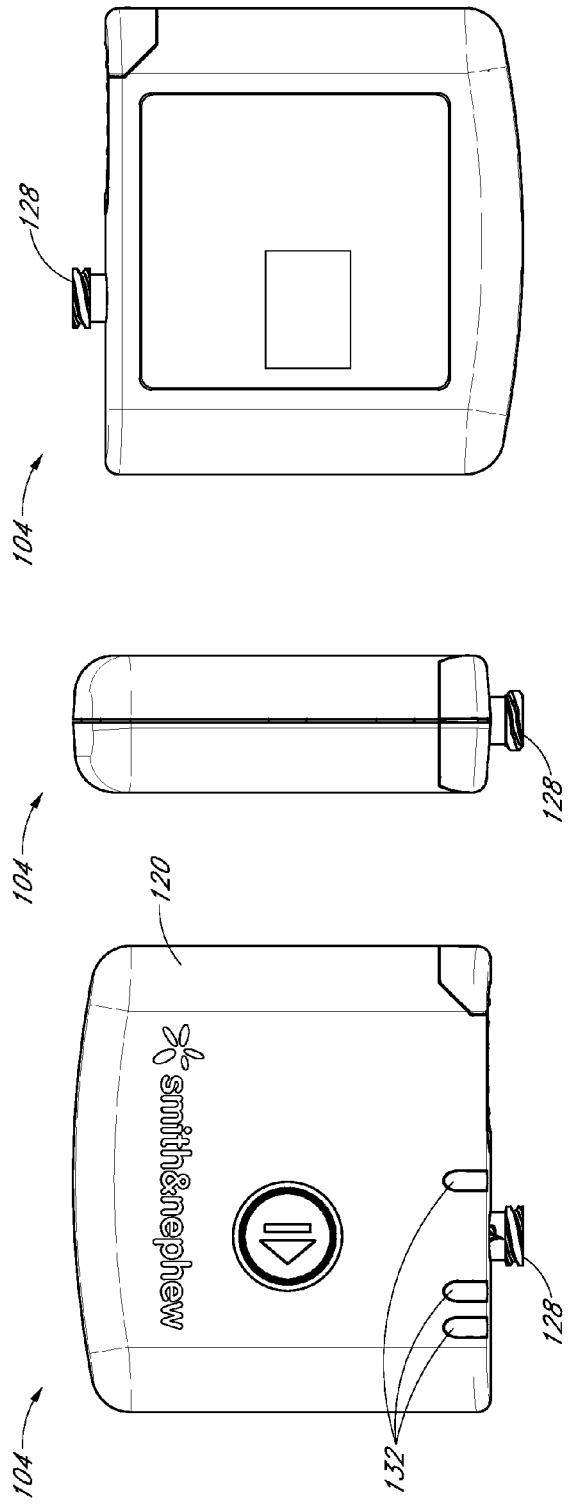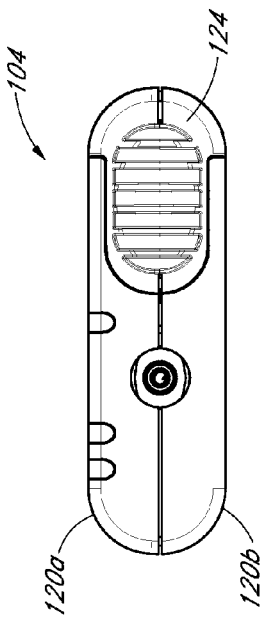

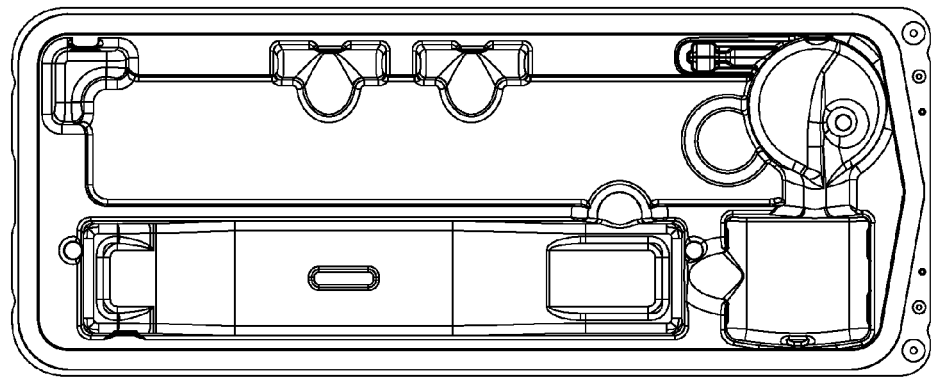
FIG. 13C
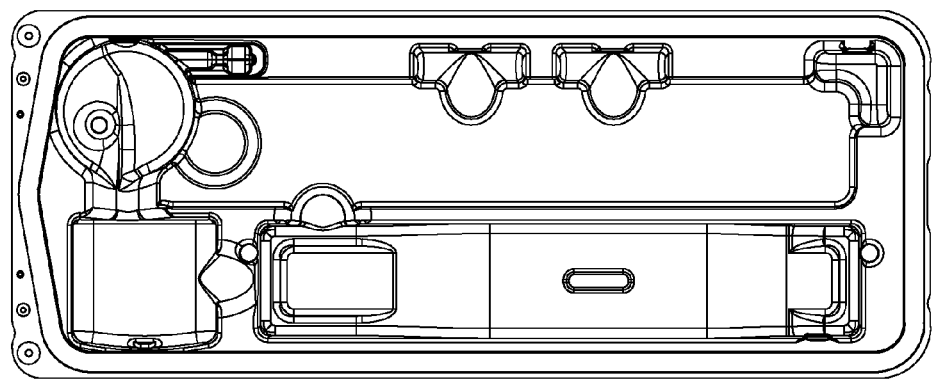
FIG. 13D
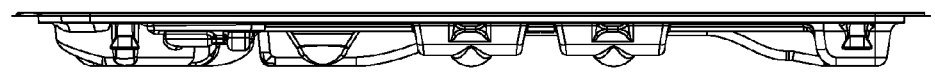
FIG. 13E
FIG. 13F
  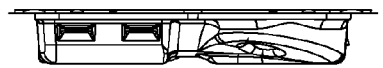
FIG. 13G       FIG. 13H

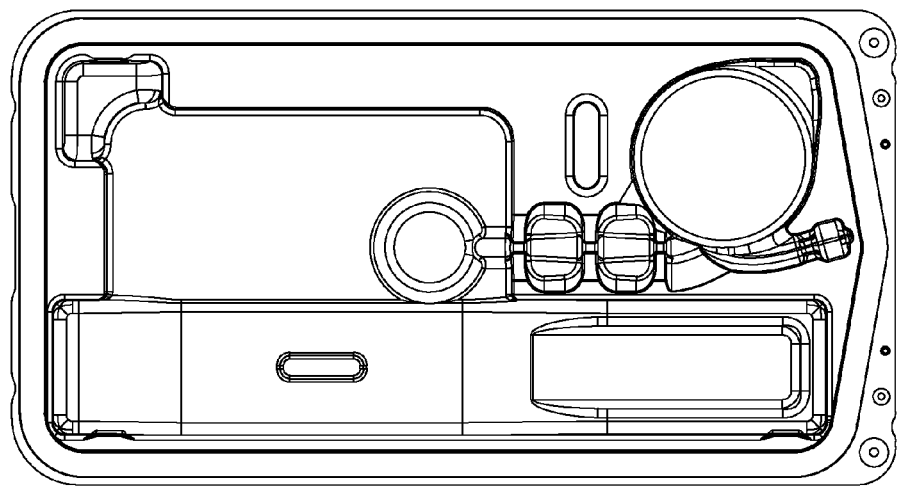
FIG. 16C
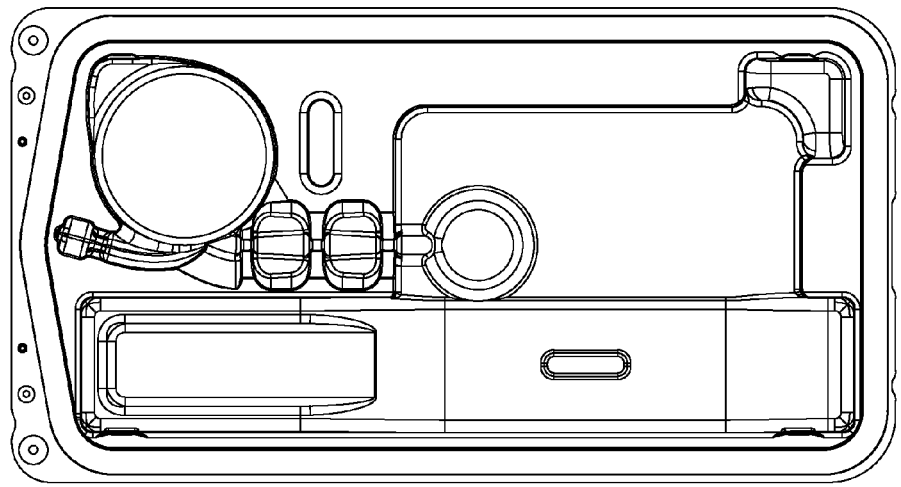
FIG. 16D
FIG. 16E
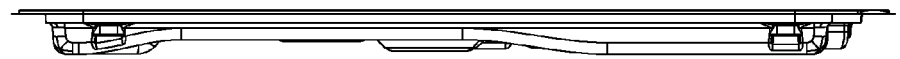
FIG. 16F
 
FIG. 16G  FIG. 16H

SYSTEMS AND METHODS FOR CONTROLLING OPERATION OF A REDUCED PRESSURE THERAPY SYSTEM

CROSS-REFERENCE TO RELATED APPLICATIONS

This application is a continuation of U.S. patent application Ser. No. 13/287,959, filed on Nov. 2, 2011, which claims priority to U.S. Provisional Patent Application No. 61/511,950, filed on Jul. 26, 2011, and is a continuation-in-part of International Application No. PCT/GB 2011/051745, entitled "PRESSURE CONTROL APPARATUS," filed on Sep. 16, 2011, which claims priority to Great Britain Patent Application 1015656.0, filed on Sep. 20, 2010. The disclosures of all these prior applications are hereby incorporated by references in their entireties. In addition, the disclosures of co-pending U.S. patent application Ser. No. 13/287,897, entitled "REDUCED PRESSURE THERAPY APPARATUSES AND METHODS OF USING SAME," filed on Nov. 2, 2011, and co-pending International Patent Application No. PCT/IB2011/002943, entitled "REDUCED PRESSURE THERAPY APPARATUSES AND METHODS OF USING SAME," filed on Nov. 2, 2011, are hereby incorporated by reference in their entireties.

BACKGROUND

1. Field of the Disclosure

Embodiments disclosed herein relate to methods and apparatuses for dressing and treating a wound with topical negative pressure (TNP) therapy. For example but without limitation, some embodiments disclosed herein relate to treating a wound with reduced pressure provided from a pump kit. Although not required, some embodiments of the pump kit can be sterile. As another non-limiting example, some embodiments disclosed herein relate to apparatuses and methods for controlling the operation of a TNP system.

2. Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

SUMMARY OF SOME EMBODIMENTS

Some embodiments disclosed herein relate to a pump assembly for reduced pressure wound therapy, comprising a housing, a pump supported within or by the housing, a flow pathway through the pump assembly, and a one-way flow valve in fluid communication with the pump and supported by the housing. Some embodiments of the one-way flow valve can be configured to substantially prevent a flow of gas through the flow pathway in a direction of flow away from the pump. The pump can have a motor, an inlet and an outlet, a first valve supported by the pump and configured to control a flow of a fluid through the inlet, and a second valve supported by the pump and configured to control a flow of a fluid through the outlet.

Some embodiments disclosed herein relate to a pump assembly for reduced pressure wound therapy, comprising a housing, a pump supported within or by the housing, a one-way flow valve in fluid communication with the pump, and a flow pathway through the pump assembly. The one-way flow valve can be configured to substantially prevent a flow of gas through the flow pathway in a direction of flow away from the pump. The pump can comprise a motor, an inlet, and an outlet. In any of the pump embodiments disclosed herein, though not required, the pump can also have a first valve configured to control a flow of a fluid through the inlet, and a second valve configured to control a flow of a fluid through the outlet. Some pump embodiments disclosed herein can use orifices or other features or components to control a flow or rate of flow of fluid through the pump.

Some embodiments disclosed herein relate to a negative pressure therapy kit for reduced pressure wound therapy, comprising a pump assembly comprising a housing, a pump supported within the housing, and a controller supported within or by the housing, and at least one switch or button supported by the housing. As used throughout this specification, the phrase "some embodiments" or "in some embodiments" is meant to refer to any embodiment described, illustrated, incorporated by reference, or otherwise disclosed herein. The at least one switch or button can be in communication with the controller and can be accessible to a user so as to permit a user to control one or more modes of operation of the pump. In some embodiments, though not required, the negative pressure therapy kit can comprise a dressing configured to form a substantially fluid tight seal over a wound, a conduit coupleable with the dressing and the pump assembly and configured to provide a substantially or completely enclosed fluid flow pathway from the pump assembly to the dressing, and a first packaging element for packaging the pump assembly, the one or more batteries, the dressing, and the conduit. In some embodiments, the controller can be configured to control an operation of the pump and the valve. Some embodiments of the negative pressure therapy kit can be configured such that the negative pressure therapy kit has been sterilized. The negative pressure therapy kit can be sterilized such that at least an inside and an outside of the housing, the at least one valve, the pump, the controller, and the at least one switch or button have been sterilized. In some embodiments, the pump can have a pump motor, an inlet and an outlet, at least one valve configured to control a flow of fluid through at least one of the inlet and the outlet, and a flow pathway through at least the inlet, the outlet, and the at least one valve.

Some embodiments disclosed herein relate to reduced pressure treatment of wounds with a reduced pressure pump. The pump embodiments disclosed herein are not required to be sterilized. However, sterilizing the reduced pressure pump before use and providing the pump and/or dressing or pump kit components in a sterile condition can permit the use of the pump in an operating room (also referred to as an operating theater) or any other location where sterility of the devices is required. For example and without limitation, some embodiments are directed to a sterile pump kit comprising a sterile pump, a sterile dressing, and a sterile conduit connectable to the dressing and the pump that can be used in an operating room.

Some embodiments disclosed herein relate to a negative pressure therapy kit for reduced pressure wound therapy, comprising a pump having a flow rate of approximately 350 milliliters per minute or less, and a dressing comprising a cover layer. The dressing can have a wound contact surface that is covered with a silicone based adhesive.

Some embodiments disclosed herein relate to a canisterless pump for reduced pressure wound therapy, comprising a housing, a flow pathway through the pump, one or more valves in communication with the flow pathway, and a pump supported within or by the housing, wherein the pump is canisterless. Some embodiments disclosed herein relate to a canisterless pump assembly for reduced pressure wound therapy, comprising a housing and a pump supported within or by the housing. The pump can have a motor, an inlet and an outlet, a first valve supported by the pump and configured to control a flow of a fluid through the inlet, and a second valve supported by the pump and configured to control a flow of a fluid through the outlet. The pump or pump assembly can be canisterless. Further, though not required for all embodiments disclosed herein, and the first and second valves can each have a leakage rate of from approximately 0.1 mL/min to approximately 10 mL/min at nominal working pressures and/or during nominal sterilization pressures, or from 0.1 mL/min or less to 5 mL/min or more, or from 1 mL/min or less to 3 mL/min or more, or between any two values in any of the foregoing ranges at nominal working pressures. In some embodiments, the leakage rate can be from approximately 0.4 mL/min to 0.7 mL/min at nominal working pressures and/or during nominal sterilization pressures.

Some embodiments of the pump assembly can have a piezoelectric pump, such as without limitation the piezoelectric pump disclosed in U.S. Pat. No. 7,550,034 and/or US 2011/186765. Some piezoelectric pumps can have orifices to perform the valve functions such that, when the pump is at rest, the flow rate through the pump can be as high as 200 mL/min. Therefore, in some embodiments, where the pump rate can be as high as approximately 300 mL/min or 320 mL/min or otherwise, the first and second valves (which can be orifices) can each have a leakage rate of up to approximately 200 mL/min.

Some embodiments disclosed herein relate to a sterile pump kit, comprising any of the pump embodiments disclosed herein, a dressing, a conduit coupleable with the dressing and the sterile pump and configured to provide a fluid pathway of reduced pressure to the dressing, one or more batteries, and a first packaging element and a second packaging element configured to be removably coupled with the first packaging element. In some embodiments, at least one of the first and second packaging elements can have recesses for receiving the sterile pump, a dressing, a conduit coupleable with the dressing and the sterile pump and configured to provide a fluid pathway of reduced pressure to the dressing. The sterile pump kit can be been sterilized after the pump, the dressing, the conduit, and the one or more batteries have been supported inside at least one of the first packaging element and the second packaging element.

Some embodiments disclosed herein relate to a method for initiating treatment of a wound in an operating room, comprising applying a sterile dressing over a wound so as to create a substantially fluid tight seal over the wound, coupling a sterile pump to dressing via a sterile conduit, and reducing a level of pressure between the dressing and the wound in an operating room by activating the pump in the operating room.

Some embodiments disclosed herein relate to apparatuses and methods for controlling operation of a negative pressure wound therapy system. In particular, but without limitation, embodiments disclosed herein relate to negative pressure therapy apparatuses and dressings, and methods and algorithms for operating such negative pressure therapy systems. In some embodiments, though not required, an apparatus can comprise a dressing configured to be placed over a wound and to create a substantially fluid impermeable seal over the wound. An apparatus can comprise a source of negative pressure configured to be coupled to the dressing. The apparatus can further comprise a controller configured to activate the source of negative pressure, monitor a duty cycle of the source of negative pressure, and determine if the duty cycle exceeds a duty cycle threshold. In some embodiments, the controller can be configured to monitor a plurality of duty cycles of the source of negative pressure over a plurality of consecutive and equal time durations, and determine if a duty cycle of the plurality of duty cycles exceeds a duty cycle threshold. The duty cycle can reflect an amount of time the source of negative pressure is active during a period of time or during a time duration of the plurality of consecutive and equal time durations In some embodiments, the controller can be configured to determine if a number of duty cycles exceed the duty cycles threshold and if that number exceeds an overload threshold. In some embodiments, the controller can be configured to determine if a set of duty cycles from the plurality of duty cycles exceeds a duty cycle threshold and determine if the number of duty cycles in the set exceeds an overload threshold. The controller can be configured to determine if the number of duty cycles that exceeds the duty cycle threshold are consecutive. In some embodiments, the overload threshold can comprise 30 duty cycles, the period of time or time duration can comprise one minute, and/or the duty cycle threshold can comprise 9%. In some embodiments, the controller can be configured to continuously monitor the duty cycle or the plurality of duty cycles.

Some embodiments of the apparatus comprise a switch configured to pause the source of negative pressure for a period of time and the controller can be configured to restart the source of negative pressure upon expiration of the period of time. The period of time can be variable. In some embodiments, the apparatus can be enclosed in a housing comprising an exterior surface and the switch comprises a button located on the exterior surface of the housing.

Some embodiments of the apparatus comprise a controller configured to provide an indication of an operating condition. The operation condition can comprise determining that the duty cycle exceeds the duty cycle threshold and the indication can comprise deactivating the source of negative pressure to indicate a leak in the seal. In some embodiments, the operating condition comprises whether the source of negative pressure is paused and the controller can be configured to provide a first indication when the source of negative pressure is active and a second indication when the source of negative pressure is paused, wherein the second indication is different from the first indication.

In some embodiments, the controller can be configured to activate the source of negative pressure to attempt to generate a desired negative pressure level under the dressing and if upon expiration of a first time interval, a pressure level under the dressing has not reached the desired negative pressure level, the controller can deactivate the source of negative pressure for a second time interval. Upon expiration of the second time interval, the controller can activate the source of negative pressure to attempt to generate the desired negative pressure level under the dressing. The controller can be configured to vary the second time interval based on a number of times the pressure level under the dressing has not reached the desired negative pressure level. For example, the controller can be configured to double the second time interval provided that a resulting value does not exceed a second interval threshold. The apparatus can comprise a sensor configured to sense pressure under the dressing and to communicate the sensed pressure to the controller.

In some embodiments, the controller can be configured to deactivate the source of negative pressure when the pressure level under the dressing has reached the desired negative pressure level and activate the source of negative pressure when the pressure level under the dressing rises above a negative pressure threshold, wherein the desired negative pressure level corresponds to a pressure that is more negative than the negative pressure threshold.

In some embodiments, the source of negative pressure can be operated by positioning a dressing over a wound to create a substantially fluid impermeable seal over the wound, delivering negative pressure to the dressing from the source of negative pressure, monitoring a duty cycle of the source of negative pressure, and providing an indication if the duty cycle is determined to exceed a duty cycle threshold. The duty cycle can reflect an amount of time the source of negative pressure is active during a period of time, such as once per minute.

Some embodiments of the apparatus can be configured to monitor a total elapsed time since an initial activation and disable the activation of the source of negative pressure when the total elapsed time reaches a lifetime threshold. The life time threshold can comprise, for example, 7 days.

In some embodiments, the apparatus for applying negative pressure to a wound comprises a dressing configured to be placed over the wound and to create a substantially fluid impermeable seal over the wound, a source of negative pressure configured to be coupled to the dressing, and a controller configured to activate the source of negative pressure, monitor a duty cycle of the source of negative pressure, and provide an indication if the duty cycle exceeds a duty cycle threshold.

In some embodiments, the apparatus comprises a dressing configured to be placed over the wound and to create a substantially fluid impermeable seal over a wound, and a pump is configured to be coupled to the dressing, a switch configured to pause the pump for a period of time, and a controller configured to restart the pump upon expiration of the period of time. The period of time can be variable. Some embodiments of the apparatus comprise a miniature diaphragm pump operated by a motor or a miniature diaphragm pump operated by a piezoelectric transducer. In some embodiments, the pump can comprise a miniature piston pump and a miniature diaphragm pump.

Some embodiments disclose a method of operating a source of negative pressure (e.g., a negative pressure pump), the method comprising positioning a dressing over a wound to create a substantially fluid impermeable seal over the wound, delivering negative pressure to the dressing from the pump, pausing the pump for a period of time, and restarting the pump upon expiration of the period of time. The period of time can be variable.

In some embodiments, a negative pressure pump can be operated by positioning a dressing over a wound to create a substantially fluid impermeable seal over the wound, aspirating fluid from the wound using the negative pressure pump, measuring a level of activity of the pump, comparing the level of activity of the pump to a threshold, and providing an indication if the level of activity exceeds the threshold. Measuring the level of activity can comprise determining a duty cycle of the pump, determining a flow rate of the fluid aspirated from the wound (e.g., by using a flow meter), measuring a rate of change of pressure under the dressing using a pressure sensor, etc. or any combination thereof.

Some embodiments disclose a method for operating a negative pressure pump, comprising positioning a dressing over a wound to create a substantially fluid impermeable seal over the wound, delivering negative pressure to the dressing from the pump to draw pressure under the dressing toward a first negative pressure set point, activating the pump to draw pressure under the dressing toward the first set point if the level of negative pressure under the dressing rises above a second negative pressure set point, monitoring an amount of time the pump has been operating, and providing an indication if the amount of time exceeds a predetermined amount of time. The method can further comprise determining the amount of time that the pump has been operating over a period of time and providing the indication if the amount of time exceeds 9% of the period of time. In some embodiments, providing the indication further comprises determining the amount of time that the pump has been operating over a period of time. In some embodiments, providing the indication further comprises activating an alarm.

In some embodiments, the apparatus can be configured to activate a source of negative pressure to draw a pressure under a negative pressure wound therapy dressing to a desired negative pressure value, such as a value between a first set point and a second set point or approximately equal to the second set point value. The level of pressure under the dressing can be measured. The apparatus can be configured to activate the source of negative pressure to draw the pressure under the dressing toward a second desired negative pressure level (e.g., the second set point value) if pressure under the dressing decays above a threshold (e.g., decays to the first set point value). The amount of time that the source of negative pressure has been operating, for example, continuously, can be monitored. The operation of the source of negative pressure can be paused or discontinued if the source of negative pressure has been operating for a predetermined amount of time without establishing approximately the second desired negative pressure level under the dressing (e.g., the second set point value).

Some embodiments disclose a method of operating a source of negative pressure, comprising positioning a dressing over a wound to create a substantially fluid impermeable seal over the wound and delivering negative pressure to the dressing from the source of negative pressure. Delivering negative pressure to the dressing from the source of negative pressure comprises activating the source of negative pressure to attempt to generate a desired negative pressure level under the dressing and updating a first count of activations; if upon expiration of a first time interval, negative pressure under the dressing has not reached the desired negative pressure level, deactivating the source of negative pressure for a second time interval, provided that the first count of activations is less than a first retry threshold; if the first count of activations is not less than the first retry threshold, deactivating the source of negative pressure for a third time interval, resetting the first count of activations, and, upon expiration of the third time interval, activating the source of negative pressure to attempt to generate the desired negative pressure level under the dressing; activating the source of negative pressure upon expiration of the second time interval to attempt to generate the desired negative pressure level under the dressing and updating the first count of activations; deactivating the source of negative pressure when the negative pressure under the dressing has reached the desired negative pressure level, resetting the first count of activations, and monitoring negative pressure under the dressing; when negative pressure under the dressing rises above a negative pressure threshold, activating the source of negative pressure and updating a second count of activations, wherein the desired negative pressure level corresponds to a pressure that is more negative than the negative pressure threshold; if before expiration of a fourth time interval negative pressure under the dressing has reached the desired negative pressure level, deactivating the source of negative pressure, monitoring negative pressure under the dressing, and resetting the second count of activations; if upon expiration of the fourth time interval negative pressure under the dressing has not reached the desired negative pressure level, deactivating the source of negative pressure for the second time interval, provided that the second count of activations is less than a second retry threshold; if the second count of activations is not less that the second retry threshold, deactivating the source of negative pressure for the third time interval, resetting the second count of activations, and, upon expiration of the third time interval, activating the source of negative pressure to attempt to generate the desired negative pressure level under the dressing and updating the first count of activations; continuously monitoring a duty cycle of the source of negative pressure; tracking a number of duty cycles that exceed a duty cycle threshold; and deactivating the source of negative pressure for a duration of the third time interval when the number of duty cycles that exceed the duty cycle threshold exceeds an overload threshold.

BRIEF DESCRIPTION OF THE DRAWINGS

Embodiments of the present invention will now be described hereinafter, by way of example only, with reference to the accompanying drawings in which:

FIGS. 2A-2F are various views of the embodiment of the pump illustrated in FIG. 1.

In the drawings like reference numerals refer to like parts.

DETAILED DESCRIPTION OF THE PREFERRED EMBODIMENTS

Figure 1:
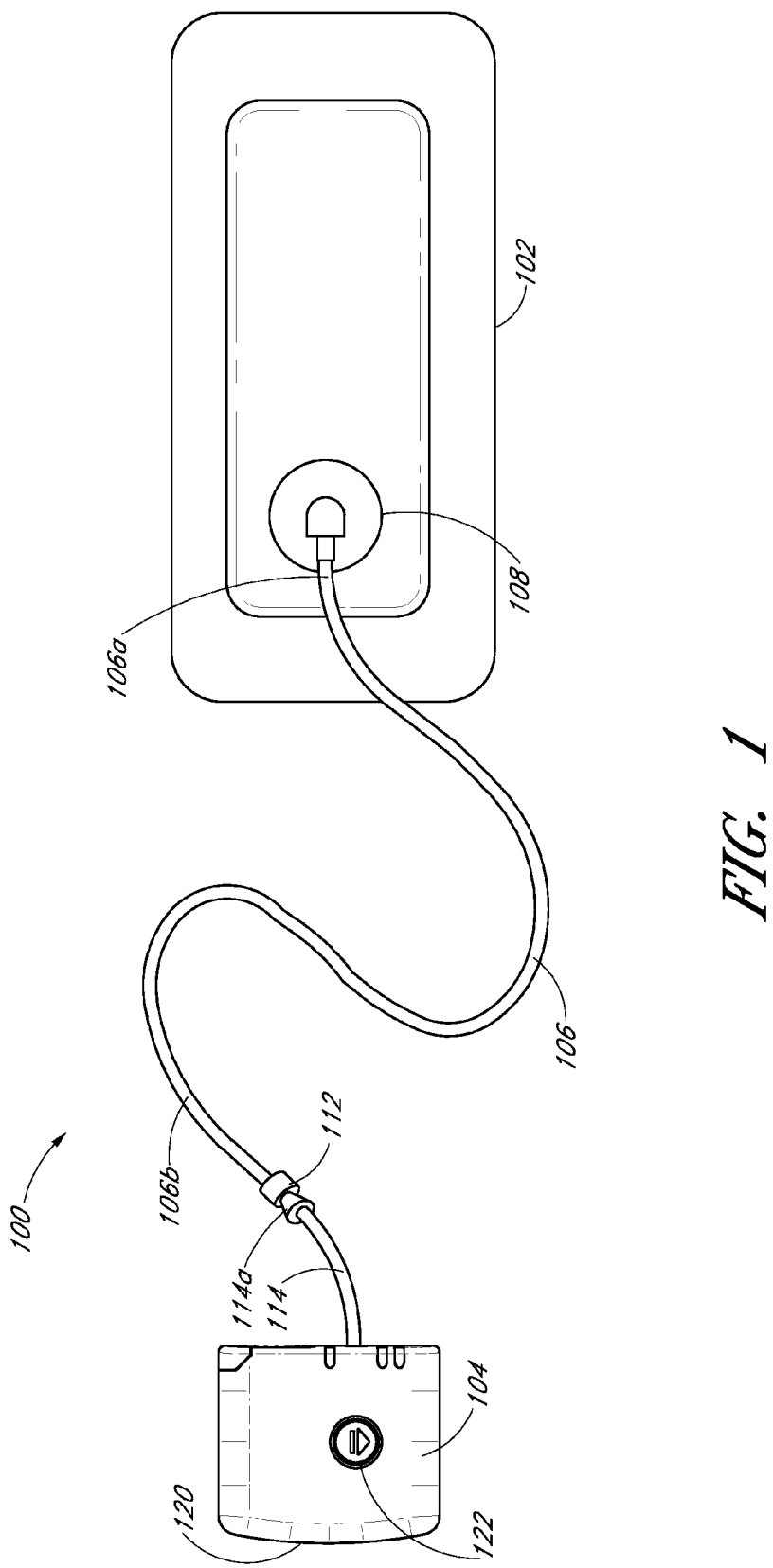
FIG. 1 illustrates an embodiment of a reduced pressure wound therapy apparatus comprising a pump, a dressing, and a conduit.
Figure 2A:
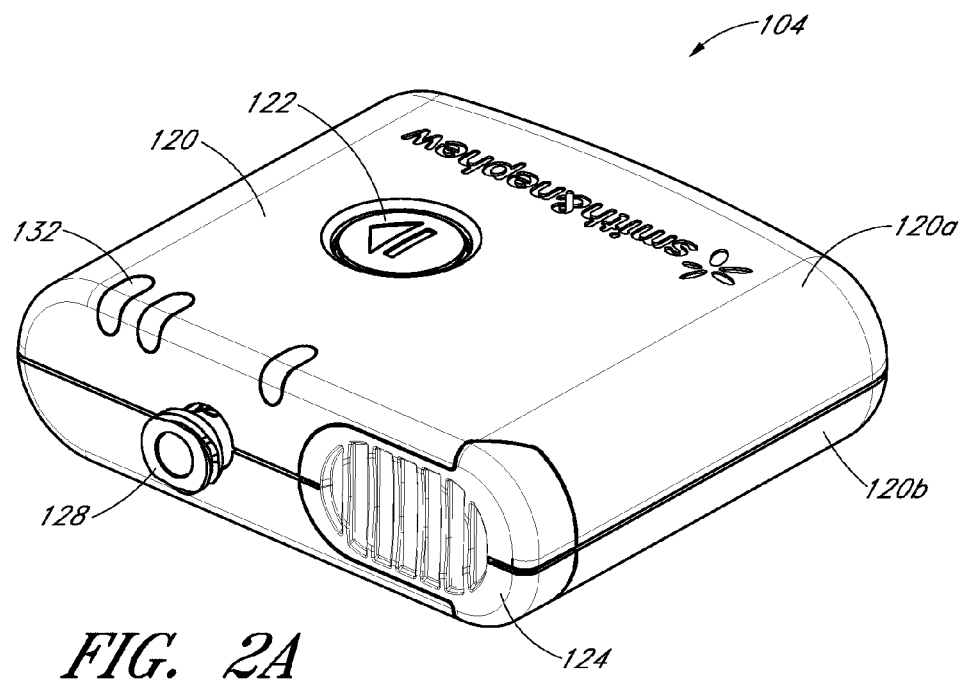
Figure 2B:
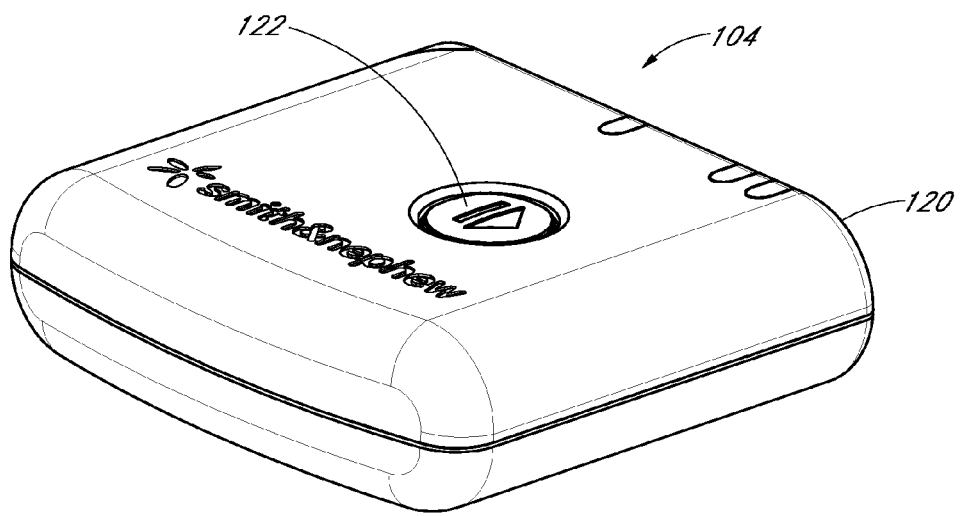

Embodiments disclosed herein relate to apparatuses and methods of treating a wound with reduced pressure. As is used herein, reduced or negative pressure levels, such as −X mmHg, represent pressure levels that are below standard atmospheric pressure, which corresponds to 760 mmHg (or 1 atm, 29.93 in Hg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Some of the embodiments comprise a pump and/or a pump and dressing kit. Some embodiments are directed to a pump and/or pump and dressing kit that have been sterilized before delivery to the hospital, operating room or theatre, or to the medical practitioner using such devices such that the sterile pump and/or a sterile pump/dressing kit can be applied immediately following the surgical or operating procedures. One advantage of this is that the surgeon can release the patient from the operating room knowing that the reduced pressure pump is operating and that the reduced pressure therapy has been started at the earliest point in time possible. A further advantage of applying the dressing kit immediately following the surgical or other procedure is that doing so can reduce the chance of infection by eliminating a subsequent dressing change that may otherwise be required in the ward. In other words, for those patients where a dressing (but not a pump) is applied in the operating theatre and then a problem is found thereafter, such as a leak or other issue with the dressing, if the dressing is required to be removed to be repositioned, replaced, or otherwise after the patient is released from the operating theater, the patient's wound may be exposed to infection risk when the dressing is repositioned, replaced, or otherwise outside of the operating theater. However, with the embodiments disclosed herein, if the pump is applied and tested while the patient is in the operating theater, any issues with the dressing that may require the dressing to be removed, repositioned, or otherwise, can be handled in the sterile operating room environment, thereby significantly reducing or eliminating the risk of exposure to pathogens, bacteria, or other contaminants. Further, it is generally not possible for a hospital to sterilize a traditional pump once it has been received by the hospital, and therefore the hospital may resort to bagging the pumps in sterile bags but risk compromising the operating room sterile field with this approach, particularly once the device is turned on and pathogens, bacteria, or other contaminants that may be inside the pump are release due to the operation of the pump.

In some embodiments, the pump can be configured to be amenable to gas sterilization, having features, components, and other characteristics that make the pump amenable to full sterilization gas exposure and penetration throughout the components of the pump. For example, without limitation, one or more pump valves have been selected or configured to permit a sufficient flow of sterilization gas therethrough such that the entire fluid pathway within the pump can be exposed to the sterilization gas. As will be explained in greater detail below, in some embodiments, the pump can have other components, such as without limitation, strategically positioned one way flow valves, to complement the other valves within the pump, which can improve the efficiency of the pump by reducing leakage through the flow pathway within the pump assembly.

Additionally, where provided, the sterile pump/dressing kit can also be designed and configured to be amenable to gas sterilization. As described below, the sterile pump/dressing kit can be configured such that all of the components comprising the sterile pump/dressing kit, including the pump assembly, are packaged together in at least a first packaging element before sterilization, permitting all of the components to be sterilized together. Furthermore, as will be described, the components comprising the sterile pump/dressing kit can be arranged in the packaging such that at least some of the components can be removed in a predefined order, making it easier for the surgeon or medical practitioner to assemble and apply the dressing to the patient.

There are a number of benefits to being able to begin treatment of a wound in the operating theater, including without limitation providing a substantially sealed barrier over the wound while the wound is in a sterile condition and environment that will inhibit or prevent bacteria or other contaminants from getting into the wound. Additionally, initiating the reduced pressure treatment at the earliest stage possible is also advantageous to healing of the wound.

Additionally, embodiments disclosed or incorporated by reference herein, such as those disclosed in U.S. patent application Ser. No. 13/092,042, Great Britain Patent Application Nos. 1015656.0, 1006986.2, 1006983.9, 1006985.4, 1006988.8, and 1008347.5 comprise improved wound dressing components. All embodiments, components, features, and other details of such disclosures are hereby incorporated by reference herein as if made part of this disclosure, and can be used in place of or in combination with any of the components, features, and other details of the embodiments disclosed herein. For example, in some embodiments, the wound dressing can be configured to act as a buffer to help prevent compression or shear forces exerted on the wound dressing, for example due to patient movement, from harming a healing wound. Embodiments of the wound dressing may act as a waste canister to collect and store wound exudate removed from a wound site, and also relate to the management of solid build-up in a wound dressing covering a wound site whilst TNP therapy is applied. Further, embodiments disclosed herein relate to a method and suction port for applying negative pressure to a wound dressing and a method of manufacturing a suction port and wound dressing.

Moreover, some embodiments disclosed herein are directed to systems that include negative pressure therapy apparatuses and dressings, and methods and algorithms for operating such negative pressure therapy apparatuses for use with negative pressure therapy dressings. In some embodiments, a negative pressure therapy apparatus comprises a pump assembly configured to, inter alia, provide negative pressure to a wound. Some embodiments of pump assemblies disclosed herein comprise novel and inventive control logic configured to control the operation of the pump assembly. For example, some embodiments comprise novel and inventive control logic configured to control the operation of a pump assembly in response to monitoring and detecting various operating conditions, such as presence and/or severity of a leak or leaks in the system, rate of flow of fluid (e.g., air, liquid and/or solid exudate, etc.) aspirated from a wound, and the like. In some embodiments, the control logic can be configured to detect a leak or leaks in a system (e.g., leak or leaks in the dressing that is in fluid communication with the pump, leak or leaks in the seal created by the dressing over the wound, etc.) as well as to control the operation of the pump assembly when such leak or leaks are detected. In some embodiments, the pump assembly can be configured to distinguish between at least a normal or low leak (e.g., a leak that has a relatively low flow rate), a high leak (e.g., a leak that has a relatively high flow rate), and a very high leak (e.g., a leak that has a relatively very high flow rate). Some embodiments can further be configured to also distinguish between the aforementioned leaks and an extremely high leak.

In some embodiments, the pump assembly can comprise a source of negative pressure, such as a miniature, disposable pump, powered by a power source, such as a battery source. The pump assembly can be configured to provide therapy for a predetermined period of time, such as approximately 1 day, 2-10 days, etc. In some embodiments, the pump assembly can be required to provide uninterrupted therapy for such period of time. In some embodiments, the pump assembly can be configured to deactivate itself a predetermined period of time (e.g., 7 days) after an initial activation. The algorithms or logic disclosed herein can help the pump assembly operate more efficiently and conserve power, for example but without limitation, battery power.

In some embodiments, the pump assembly can be configured to monitor the duty cycle of the source of negative pressure (e.g., a pump). As is used herein, "duty cycle" reflects the amount of time the source of negative pressure is active or running over a period of time. In other words, the duty cycle reflects time that the source of negative pressure is in an active state as a fraction of total time under consideration. This can be represented mathematically as:

$$DC = t/T, \qquad (1)$$

where DC is the duty cycle, t is the duration that the source of negative pressure is active, and T is the total time under consideration. Duty cycle can be measured as an absolute value (e.g., X seconds), a proportion (e.g., 1/X), a percentage (e.g., X %), etc. For example, if over a period of 1 minute the source of negative pressure has been on (or operating) for 6 seconds and off (or not operating) for 54 seconds, the duty cycle can be represented as 6 seconds, $1/10$, 10%, etc.

In some embodiments, the pump assembly can include a controller configured to monitor the duty cycle of the source of negative pressure. Duty cycle measurements can reflect a level of activity of the source of negative pressure. For example, duty cycle can indicate that the source of negative pressure is operating normally, working hard, working extremely hard, etc. Moreover, duty cycle measurements, such as periodic duty cycle measurements, can reflect various operating conditions, such as presence and/or severity of leaks in the system, rate of flow of fluid (e.g., air, liquid and/or solid exudate, etc.) aspirated from a wound, and the like. Based on the duty cycle measurements, such as by comparing the measured duty cycle with a set of thresholds (e.g., determined in calibration), the controller can execute and/or be programmed to execute algorithms or logic that control the operation of the system in accordance with various system requirements. For example, duty cycle measurements can indicate presence of a high leak in the system, and the controller can be programmed to indicate this condition to a user (e.g., patient, caregiver, physician, etc.) and/or temporarily suspend or pause operation of the source of negative pressure in order to conserve power.

In some embodiments, the system can be configured to monitor the rate of flow by any other suitable means. The pump assembly can be configured to use flow meters (e.g., mechanical, pressure-based, optical, mass, thermal mass, electromagnetic, sonic, ultrasonic, laser Doppler, etc.), anemometers, pressure transducers or sensors, electromagnetic sensors (e.g., sensors configured to measure pump speed, such as Hall sensors), electromagnetic measurements (e.g., measuring the current and/or power draw of the pump, measuring current and/or power drain of the power source, measuring the remaining capacity of the power source, etc.) or any combination thereof. Based on the monitored rate of flow, such as by comparing the rate of flow with a set of thresholds (e.g., determined in calibration), the controller can execute and/or be programmed to execute algorithms or logic that control the operation of the system in accordance with various system requirements. For example, the controller can be configured to obtain periodic measurements from a pressure sensor or obtain periodic feedback from a pump motor. The pressure sensor can measure pressure under the dressing. The controller can determine the rate of flow, for example, by determining a pressure gradient, rate of change of pressure, and/or pressure decay rate. For instance, a positive pressure gradient (e.g., one that is increasing) can reflect an increasing rate of flow as (e.g., a leak) in relation to a threshold, and the controller can be programmed to indicate this condition to the user.

In some embodiments, the system can be provided for treatment of a wound. The dressing can create a substantially sealed or closed space around the wound (e.g., under the dressing), and the pump assembly can have a sensor which can periodically or continuously measure or monitor a level of pressure in this space. The pump assembly or a controller thereof can be configured to control the level of pressure in the space (e.g., under the dressing) between a first negative pressure set point limit and at least a second negative pressure set point limit. In some embodiments, the first set point limit can be approximately −70 mmHg, or from approximately −60 mmHg or less to approximately −80 mmHg or more. In some embodiments, the second set point limit can be approximately −90 mmHg, or from approximately −80 mmHg or less to approximately −100 mmHg or more.

In some embodiments, the system can be configured to include "retry" functionality and/or logic. The pump assembly can be configured to monitor a level of negative pressure under the dressing (which can correspond to the level of negative pressure in the wound cavity), compare the monitored level to a desired negative pressure level (e.g., first set point, second set point, etc.), and suspend or pause therapy if the desired negative pressure level is not reached during a certain time interval. Following the suspension or pause of therapy, the pump assembly can be configured to restart therapy (e.g., restart the source of negative pressure) and attempt to again generate the desired negative pressure level under the dressing. Retry functionality can, for instance, conserve battery power and allow transient and/or non-transient leaks to become resolved without user intervention or allow the user to fix the leak (e.g., straighten the dressing, fix the seal, check the connection or connections, etc.). In some embodiments, a controller can execute and/or be programmed to execute retry functionality and/or logic.

In some embodiments, the system can be configured to provide "play/pause" functionality and/or logic via a switch, button, etc. located on the exterior of the pump assembly's housing or any other suitable place where it can be accessed by the user. Play/pause functionality can allow the user to suspend and/or restart therapy (e.g., pause and/or restart the pump). The pump assembly can be configured to automatically restart therapy following a certain predetermined or variable pause interval. The pump assembly can be configured to automatically restart therapy upon expiration of such interval and/or indicate to the user expiration of such interval.

In some embodiments, the system can be configured to provide indication, alarms, etc. to the user reflecting operating conditions. The system can include visual, audible, tactile, and other types of indicators and/or alarms configured to signal to the user various operating conditions. Such conditions include system on/off, standby, pause, normal operation, dressing problem, leak, error, and the like. The indicators and/or alarms can include speakers, displays, light sources, etc., and/or combinations thereof. For example, indication can be provided by activating or deactivating the source of negative pressure, reducing negative pressure level generated by the source of negative, lowering the amount of power used by the source of negative pressure, etc. or any combination thereof.

FIG. 1 illustrates an embodiment of a reduced pressure wound treatment apparatus 100 comprising a wound dressing 102 in combination with a pump assembly 104. In any of the apparatus embodiments disclosed herein, as in the embodiment illustrated in FIG. 1, the pump assembly can be a canisterless pump assembly (meaning that the pump assembly does not have an exudate or liquid collection canister). However, any of the pump embodiments disclosed herein can be configured to include or support a canister. Additionally, in any of the apparatus embodiments disclosed herein, any of the pump assembly embodiments can be mounted to or supported by the dressing, or adjacent to the dressing. The dressing 102 may be placed over a wound (not illustrated) as described in greater detail in U.S. patent application Ser. No. 13/092,042, which disclosure is hereby incorporated by reference and made part of this disclosure, and a conduit 106 may then be connected to the dressing 102. Dressing 102 or any other dressing disclosed herein can have any of the materials, sizes, components, or other details of any of the dressing embodiments disclosed in U.S. patent application Ser. No. 13/092,042, and such embodiments and illustrations thereof are hereby incorporated by reference in their entireties as if made part of this disclosure. The conduit 106 or any other conduit disclosed herein can be formed from polyurethane, PVC, nylon, polyethylene, silicone, or any other suitable material.

Some embodiments of the dressing 102 can have a port 108 configured to receive an end of the conduit 106 (e.g., the first end 106a of the conduit 106), though such port 108 is not required. In some embodiments, the conduit can otherwise pass through and/or under the dressing 108 to supply a source of reduced pressure to a space between the dressing 102 and the wound so as to maintain a desired level of reduced pressure in such space. Some embodiments of the apparatus 100 can be configured such that the first end 106a of the conduit 106 is preattached to the port 108. The conduit 106 can be any suitable article configured to provide at least a substantially sealed fluid flow pathway between the pump assembly 104 and the dressing 102, so as to supply the reduced pressure provided by the pump assembly 104 to the dressing 102.

The dressing 102 can be provided as a single article with all wound dressing elements (including the port 108) pre-attached and integrated into a single unit. The wound dressing 102 may then be connected, via the conduit 106, to a source of negative pressure such as the pump assembly 104. In some embodiments, though not required, the pump assembly 104 can be miniaturized and portable, although larger conventional pumps such as the EZ CARE™ pump can also be used with the dressing 102.

It will be understood that embodiments of the present invention are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

The wound dressing 102 can be located over a wound site to be treated. The dressing 102 can form a substantially sealed cavity or enclosure over the wound site. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the apparatus are designed to operate without the use of an exudate canister. The dressing 102 can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

The apparatus 100 can be manufactured in a wide variety of different models or versions, wherein the size of the dressing 100 can be varied to accommodate a wide range of wound sizes. For example, apparatuses 100 can be made having the following sizes of dressings 102 and wound pads (i.e., absorbent elements, not illustrated in FIG. 1).

| Approximate Dressing Size | Approximate Wound Pad Size |
| --- | --- |
| 10 cm × 30 cm (4 in × 11.75 in) | 5 cm × 20 cm (2 in × 8 in) |
| 15 cm × 15 cm (6 in × 6 in) | 10 cm × 10 cm (4 in × 4 in) |
| 15 cm × 20 cm (6 in × 8 in) | 10 cm × 15 cm (4 in × 6 in) |
| 10 cm × 20 cm (4 in × 8 in) | 5 cm × 10 cm (2 in × 4 in) |
| 20 cm × 20 cm (8 in × 8 in) | 15 cm × 15 cm (6 in × 6 in) |

Some embodiments of the overlay or dressing can be substantially impervious to air flow and the flow of bacteria or other contaminants through the overlay layer, while being pervious to vapor transmission.

In some embodiments, it may be preferable for the wound site to be filled partially or completely with a wound packing material. This wound packing material is optional, but may be desirable in certain wounds, for example deeper wounds. The wound packing material can be used in addition to the wound dressing 102. The wound packing material generally can comprise a porous and conformable material, for example foam (including reticulated foams), and gauze. Preferably, the wound packing material is sized or shaped to fit within the wound site so as to fill any empty spaces. The wound dressing 102 can then be placed over the wound site and wound packing material overlying the wound site. When a wound packing material is used, once the wound dressing 102 is sealed over the wound site, TNP is transmitted from a pump through the wound dressing 102, through the wound packing material, and to the wound site. This negative pressure draws wound exudate and other fluids or secretions away from the wound site.

In some embodiments, the tubing 106 can have a connector 112 positioned at a second end 106b of the tubing 106. The connector 112 can be configured to couple with a short length of conduit 114 projecting from the pump assembly 104, with a mating connector 114a in communication with the short length of conduit 114, with a connector supported by the pump housing (as described in greater detail below), or otherwise. The length of the tubing 114 in some embodiments can be approximately 14 mm (0.55 in), or from approximately 0.5 in to approximately 5 inches. The short length of conduit or tubing 114 can decrease the discomfort to a patient while laying or otherwise resting on the pump and connector 112. Configuring the pump assembly 104 and tubing 106 so that the tubing 106 can be quickly and easily removed from the pump assembly 104 can facilitate or improve the process of dressing or pump changes, if necessary. Any of the pump embodiments disclosed herein can be configured to have any of the connection configurations disclosed herein between the tubing and the pump.

In some embodiments, as in the illustrated embodiment, the pump assembly 104 can be of a sufficiently small and portable size to be supported on a user's body or in a user's clothing. For example, the pump assembly 104 can be sized to be attached using adhesive medical tape or otherwise to a person's skin in a comfortable location, adjacent to or on the dressing 102 or otherwise. Further, the pump assembly 104 can be sized to fit within a person's pants or shirt pocket, or can be tethered to a person's body using a lanyard, pouch, or other suitable device or article.

In some embodiments, the pump assembly 104 can be powered by one or more batteries (for example, two batteries) and can weigh approximately 84 grams, or less than 90 grams, including the weight of the batteries. In some embodiments, the pump assembly 104 can have any desired number of batteries and can weigh from approximately 80 grams to approximately 90 grams, or from approximately 75 grams to approximately 100 grams, or between any values within the foregoing ranges. For example, the weight and/or size of the pump assembly 104 could be reduced by reducing the battery size and/or weight (to, for example, AAA sized batteries, or smaller) or the pump size and/or weight.

Further, some embodiments of the pump assembly 104 can be sized to have a total volume defined by an outside surface of the pump of approximately 92.5 cubic centimeters (approximately 5.6 cubic inches), or 92.5 cubic centimeters (5.6 cubic inches) or less, or between 75 cubic centimeters or less and 115 cubic centimeters or more, or between 85 cubic centimeters and 100 cubic centimeters. Additionally, the pump assembly 104 can be further miniaturized using techniques known to one of ordinary skill in the art to sizes in the range of approximately 40 cubic centimeters, or 40 cubic centimeters or less, or between 30 cubic centimeters or less and 60 cubic centimeters or more. Some embodiments of the pump assembly 104 can be sized to have a total volume of between 2 cubic inches or less and 6.5 cubic inches or more, or from approximately 4 cubic inches to approximately 6 cubic inches, or between any values within the foregoing ranges.

The pump assembly 104 can have an overall outside size that is approximately 7.2 cm×approximately 6.4 cm×approximately 2.1 cm (or 7.2 cm×6.4 cm×2.1 cm), or a maximum of approximately 8.5 cm×approximately 8.5 cm×approximately 3 cm. Additionally, the pump assembly 104 can have an overall outside size that is approximately 5.5 cm×approximately 4.8 cm×approximately 1.5 cm (or 5.5 cm×4.8 cm×1.5 cm). As mentioned, the size and weight of the pump assembly 104 can be optimized, as it is in the embodiments disclosed herein, to make it more comfortable to wear or carry by the user, thereby affording increased mobility.

The negative pressure range for some embodiments of the present disclosure can be approximately −80 mmHg, or between about −20 mmHg and −200 mmHg. Note that these pressures are relative to normal ambient atmospheric pressure thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the apparatus 100. Other details regarding the operation of the pump assembly 104 are set forth in U.S. patent application Ser. No. 13/092,042, and such embodiments, configurations, details, and illustrations thereof are hereby incorporated by reference in their entireties as if made part of this disclosure.

Figure 3A:
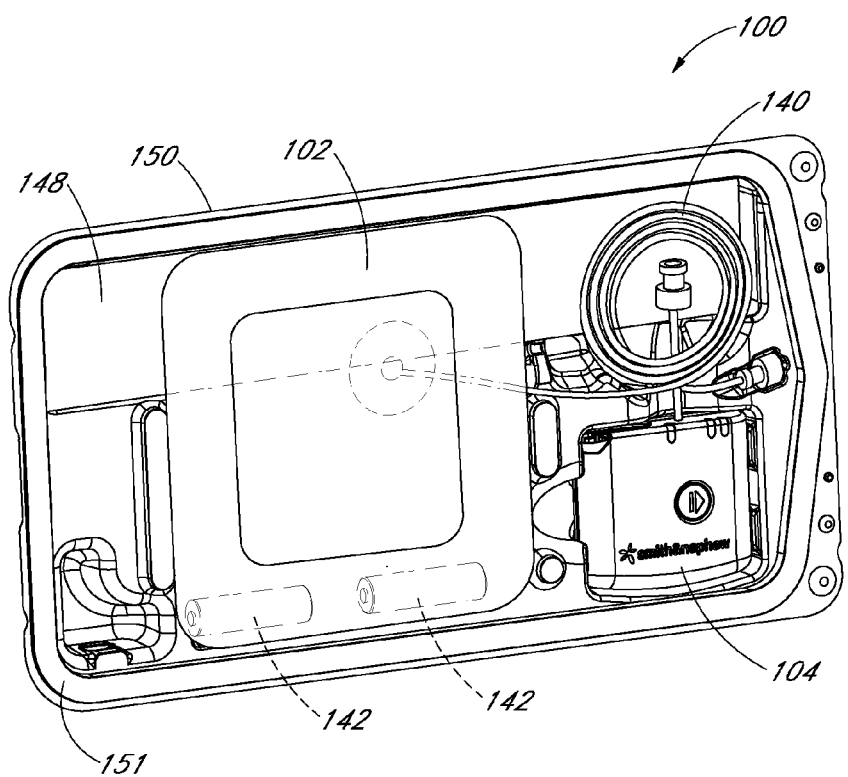
FIG. 3A illustrates an embodiment of a wound dressing kit comprising a dressing, a pump, a conduit, two batteries, and one or more sealing strips supported in a first packaging element.
Figure 3B:
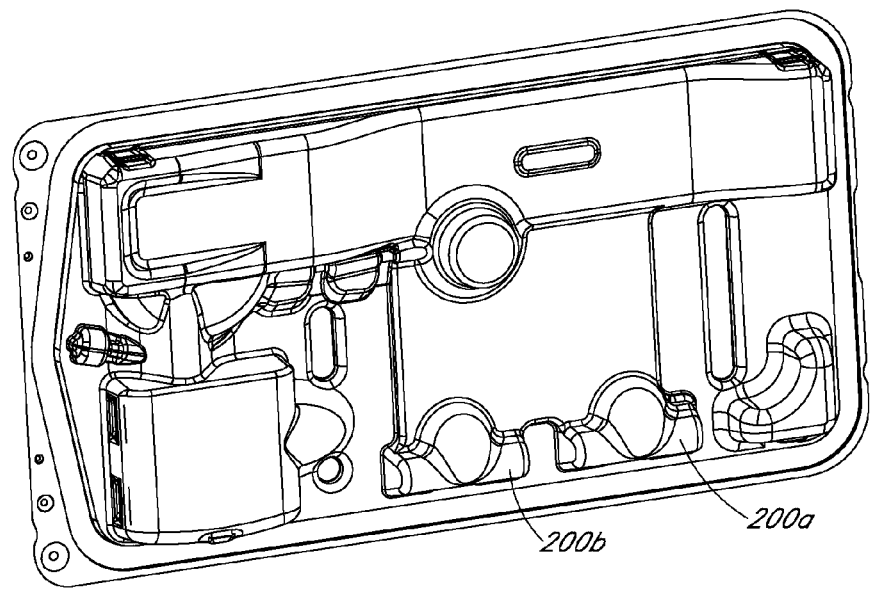
FIG. 3B is a bottom isometric view of the embodiment of the wound dressing kit of FIG. 3A.
Figure 3C:
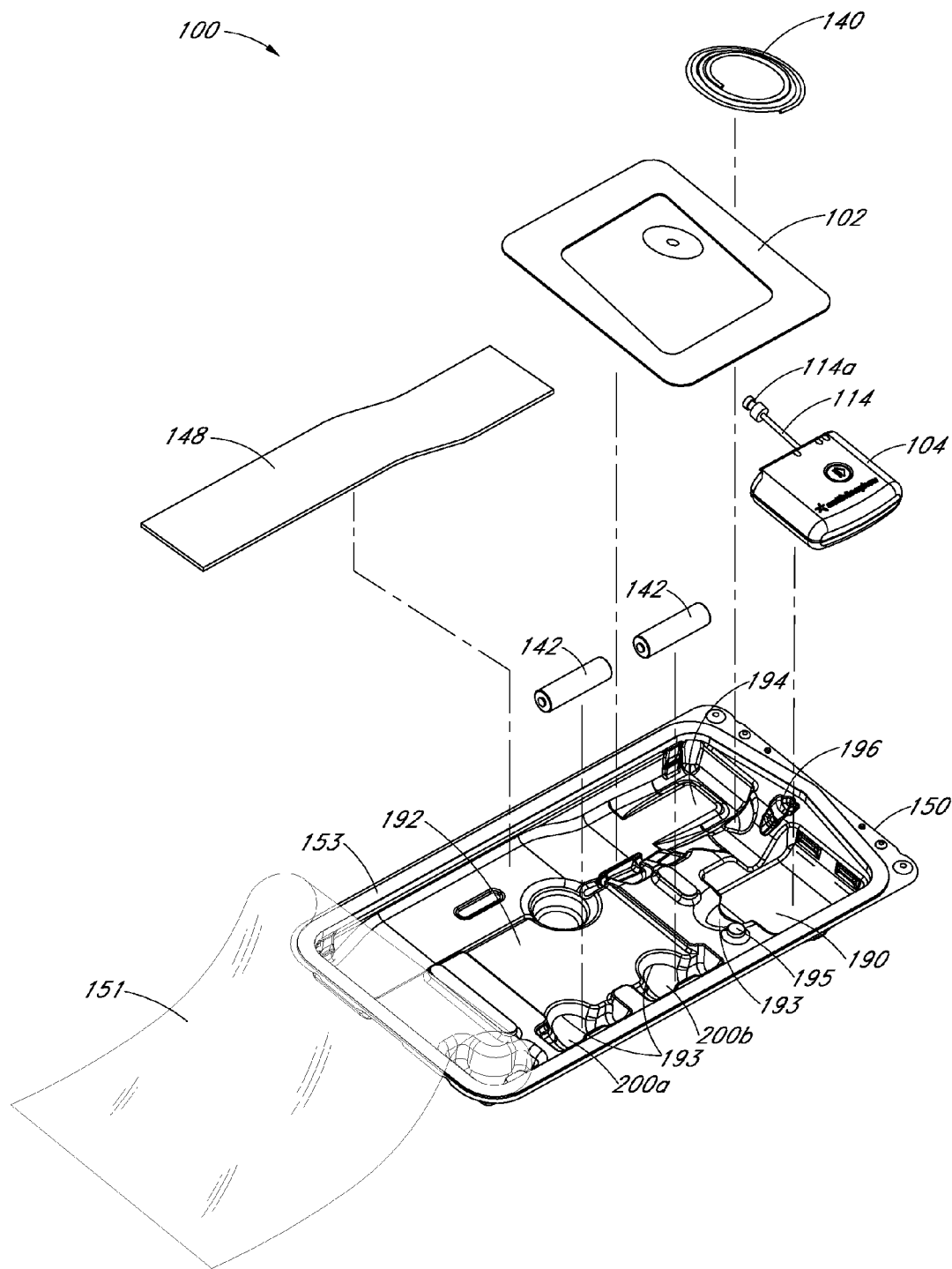
FIG. 3C is an exploded view of the embodiment of the wound dressing kit of FIG. 3A.

FIGS. 2A-2F are various views of the embodiment of the pump assembly 104 illustrated in FIG. 1. FIG. 3A illustrates an embodiment of a wound dressing kit 100 comprising a dressing 102 (which can be any of the dressing embodiments disclosed or incorporated by reference herein), a pump assembly 104, a conduit 140, one or more batteries 142 (two being shown), and one or more sealing strips 148 supported in a first packaging element 150. FIG. 3B is a bottom isometric view of the embodiment of the wound dressing kit 100 of FIG. 3A. FIG. 3C is an exploded view of the embodiment of the wound dressing kit 100 of FIG. 3A.

With reference to FIGS. 2A-3C, the pump assembly 104 can have a housing 120 comprising a first housing member 120a and a second housing member 120b, a control button 122 (which can also be a switch or other similar component), a battery cover 124, a connector 128, and one or more lights, which can be LED lights. In some embodiments, the pump assembly 104 can have more than one button 122, and can have three or more lights 132. The lights 132 can be configured to alert a user to a variety of operating and/or failure conditions of the pump assembly 104, including alerting the user to normal or proper operating conditions, pump failure, power supplied to the pump or power failure, the condition or voltage level of the batteries, detection of a leak within the dressing or flow pathway, suction blockage, or any other similar or suitable conditions or combinations thereof.

The housing 120 can be configured such that a sterilization gas, such as ethylene dioxide, can penetrate into the housing such that the internal components of the pump assembly 104 are exposed to the sterilization gas during normal sterilization processes. Typically, the pump will be exposed to the sterilization gas in a chamber that has been substantially evacuated of air or any other gas, so that the sterilization gas is drawn into the pump housing 120 and into the other spaces and chambers within the pump assembly 104. For example, some embodiments of the pump housing 120 can have an unsealed gap surrounding the connector 128 through which the sterilization gas can pass. Also, in some embodiments, the first housing member 120a can be joined to the second housing member 120b without the use of a seal therebetween.

For the sterilization process, in some embodiments, the components to be sterilized can be subjected to the following steps, inter alia, in any order. The components can be placed in a chamber or container that is evacuated to approximately 70 mBarA (or between 67 mBar A and 80 mBarA) for between approximately 15 minutes and 1 hour and 15 minutes. The components can also be subjected to inert dilution, steam pressure or conditioning, or nitrogen cycles, which can be followed by further evacuation cycles. Ethylene oxide or any other suitable sterilization gas can be introduced into the chamber or container at a pressure set point of approximately 482 mBarA (or from approximately 467 mBarA to approximately 500 mBarA). The components can be exposed to the sterilization gas at a temperature of approximately 46 degrees Celsius (or from approximately 42 degrees Celsius to 49 degrees Celsius), or up to 60 degrees Celsius. The components can be exposed to the sterilization gas for approximately 10 minutes (short cycle) or approximately 1 hour (long cycle), or from approximately 9 minutes to approximately 11 minutes (short cycle), or from approximately 59 minutes to approximately 1 hour (long cycle), or longer. The components or chamber can be flushed with nitrogen and/or air and/or degassed thereafter.

The pump assembly 104 can be powered by one or more batteries 142. The batteries 142 can be lithium chloride or any other suitable batteries that are suitable for exposure to ethylene dioxide and/or other sterilization gases. The batteries 142 can be supported outside of the pump housing 120 so as to minimize or eliminate the chance of an electrical spark which could cause an explosion in the presence of the sterilization gas or an explosive gas during the sterilization process when supported in the packaging element or elements. Additionally, where there are a plurality of batteries 142, the batteries can be spaced apart or otherwise separated in the packaging to prevent any power loss or sparking of the batteries during the sterilization process or otherwise before usage.

With reference to FIG. 3A, the batteries 142 and the sealing strip or strips 148 can be positioned beneath the dressing 102 so that the dressing 102 must be removed from the first packaging element 150 before the batteries 142 are removed, thereby suggesting an order by which the components of dressing kit 100 are removed from the packaging 150 and/or applied to the patient or assembled to the other components comprising the apparatus 100.

In some embodiments, the conduit 140 can be positioned within the packaging 150 so that both ends of the conduit 140 are free or otherwise disconnected from the other components of the apparatus 100 to improve the exposure of the internal surfaces of the conduit 140 to and/or to ensure complete exposure of the tubing to the sterilization gas. The ends of the conduit 140 can be supported within recesses formed in the first packaging element 150.

The first packaging element 150 can have one or more recesses configured to receive and support the components of the apparatus 100, including a recess 190 for receiving the pump assembly 104, a recess 192 for receiving the dressing 102, a recess 194 for receiving the one or more sealing strips 148 and/or the conduit 140, a recess 196 for receiving the conduit 114 and/or connector 114a, if present, and spaced apart recesses 200a and 200b for the batteries 142. Spacing apart the batteries can reduce or eliminate the risk of explosion during sterilization procedures due to the potentially flammable nature of ethylene oxide.

In some embodiments, the first packaging element 150 can be made from a material or combination of materials that is sufficiently rigid and/or robust to hold the batteries, pump and/or other components in place during processing or transportation of the dressing kit. For example, some embodiments of the first packaging element 150 can be configured to provide a compression or interference fit for the components, such as the batteries, the pump, or other components, sufficient to withstand accelerations of between approximately 15 G and approximately 25 G, or between 1 G and 40 G, or between 1 G and 20 G, or between 25 G and 40 G. Some embodiments of the first packaging element 150 can be configured to tightly hold the pump, batteries, tubing (with tubing pinches or recesses) and other components sufficient to prevent movement or dislodgement of components which could lead to short circuit or melting/abrasion of the packaging, resulting in damage to the packaging or bacterial ingress while not impeding the ability of the user to remove such components from the packaging when needed.

Additionally, as illustrated, the first packaging element 150 can have grooves or recesses 193 sized and configured to facilitate the surgeon's or user's access and removal of the various components of the apparatus 100, both with and without a gloved hand. Further, bosses or projections 195 can be formed in the first packaging element 150 to provide additional support and protection to the packaging and kit components. The first packaging element 150 can be made from any suitable material that can be sterilized, including a recyclable virgin PETG Blue tinted 0.80 Eastman 6763 medical grade provided by Nelipak Custom Thermoformed Products. The packaging element 150 can be extruded and thermoformed from EASTAR™ Chemical Product EASTAR copolyester resin. For example, the raw material, which can be an extruded sheet or film, can be thermoformed using a vacuum and press over a dye tool under elevated temperatures. Other suitable materials for the first packaging element 150 include polycarbonate, PVC, or any other suitable resin or plastic material. In some embodiments, the first packaging element can be made from a material (including a plate, sheet, film, or otherwise) having a thickness of 0.8 mm (or approximately 0.8), or a thickness of 0.8 mm or less, or 1.0 mm or less, or between approximately 0.7 mm and 1.2 mm.

A gas permeable cover 151 (also referred to herein as a second packaging element) can be sealingly positioned over the first packaging element 150 to provide a bacteria and contaminant barrier to the contents of the dressing kit 100. For example, a sheet-like layer or film of TYVEK™, paper, or any other suitable material can be sealed to a rim portion 153 of the first packaging element 150. The cover 151 can be made from any suitable material, including TYVEK, which is permeable to the sterilization gas but provides a barrier to bacteria and other contamination. The cover 151 can be opaque, clear, or translucent.

The cover 151 can be sealingly coupled with the first packaging element 150 after all of the dressing kit components assembled therein. Thereafter, the first packaging element 150, cover 151, and the dressing kit components can be positioned within a sealed, impermeable bag having a TYVEK or other sterilization gas permeable patch of material over an opening formed in the bag to permit the sterilization gas to enter the bag and sterilize the components of the dressing kit.

Figure 4A:
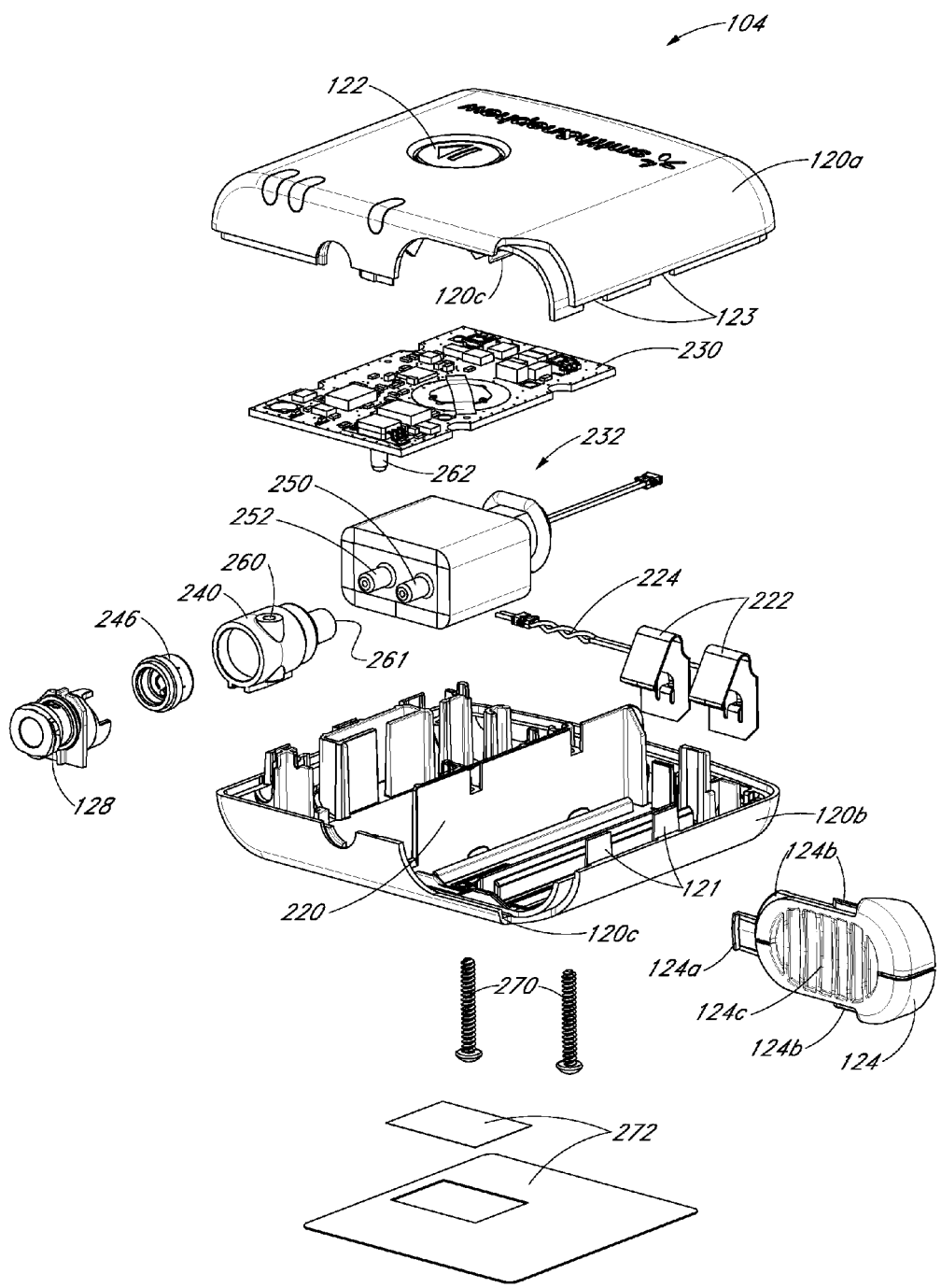
FIG. 4A is a first exploded view of the embodiment of the pump of FIG. 1.
Figure 4B:
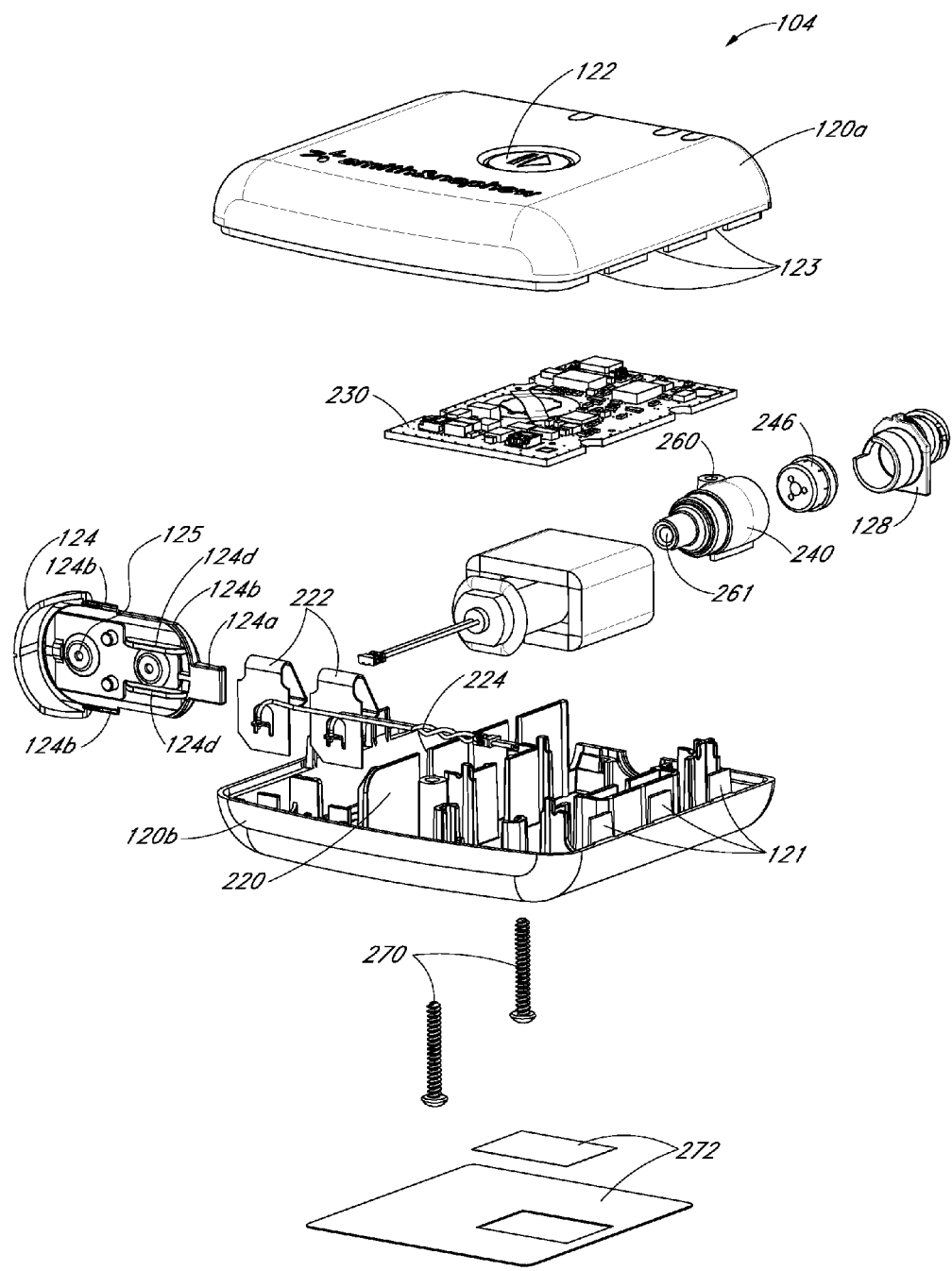
FIG. 4B is a second exploded view of the embodiment of the pump of FIG. 1.
Figure 5B:
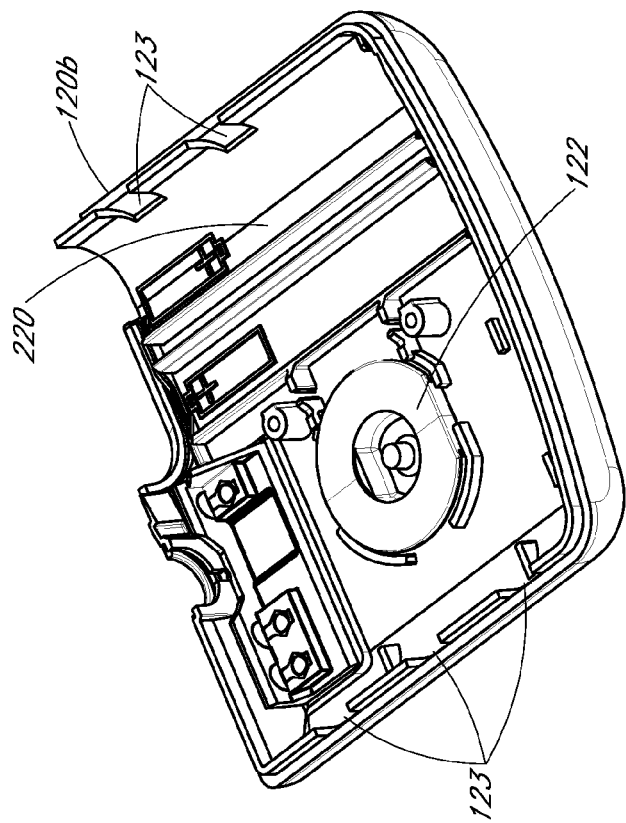
FIGS. 5A and 5B are first and second views of the first housing member.
Figure 5A:
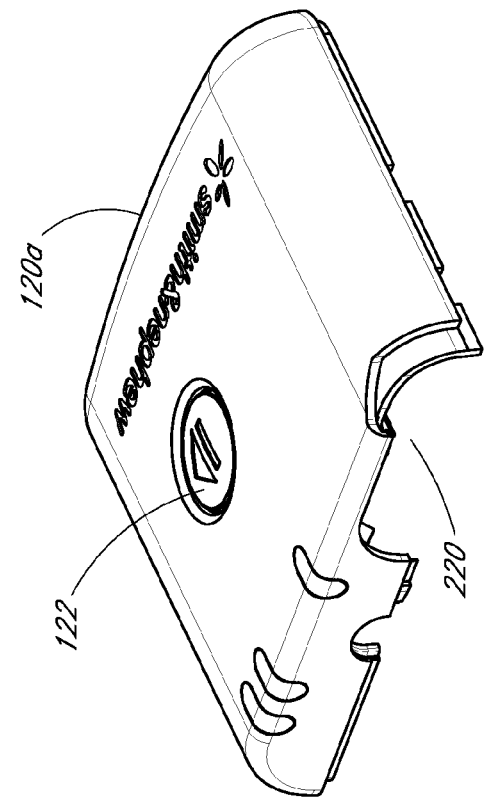
Figure 6B:
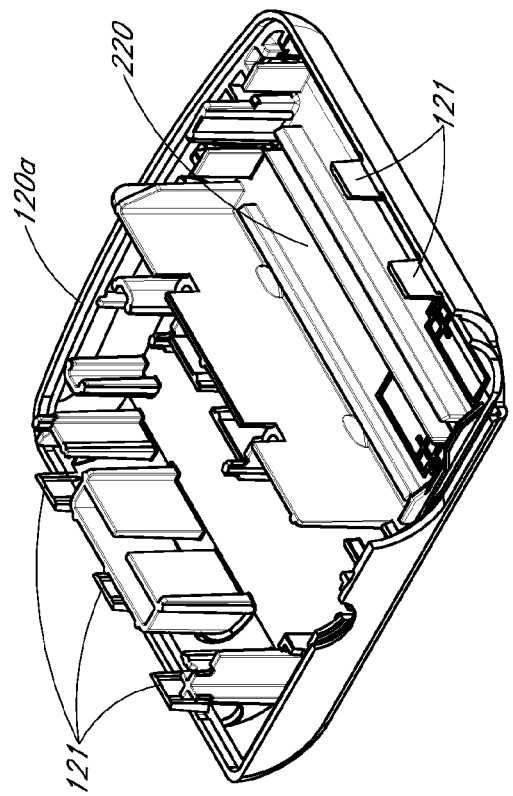
FIGS. 6A and 6B are first and second views of the second housing member.
Figure 6A:
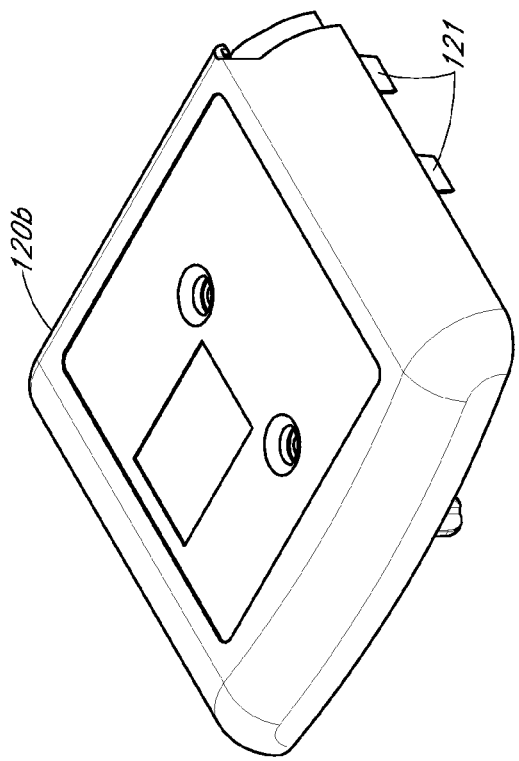

FIGS. 4A and 4B are first and second exploded views of the embodiment of the pump assembly 104 of FIG. 1, showing the first housing member 120a separated from the second housing member 120b. FIGS. 5A and 5B are first and second views of the first housing member 120a. FIGS. 6A and 6B are first and second views of the second housing member 120b. With reference to FIGS. 4A-6B, some embodiments of the pump assembly 104 can have a battery compartment 220 supported or formed within the housing 120. One or more battery contacts 222 can be supported within the battery compartment 220. One or more electrical wires 224 can connect the battery contacts 222 to a pump 232 and/or a control board 230. The pump assembly 104 can be assembled in a clean room to reduce the risk of contamination or bioburden that the pump is exposed to or can collect during assembly.

In some embodiments, the pump 232 can comprise a motor, an inlet port or connector 250, and an outlet port 252. The pump 232 can have one or more valves therein. For example, a first valve can be positioned within the pump 232 adjacent the inlet port 250. Additionally, a second valve can be positioned within the pump 232 adjacent the outlet port 252. The pump 232 can define a flow pathway through the inlet port 250, through the first and second valves, and out the outlet port 252.

In some embodiments, the battery contacts 222 can also be configured to have polarity protection. For example, similar to the one or more protrusions 124d adjacent to the battery contact 125, the one or more of the battery contacts 222 can have plastic or other protrusions (not illustrated) adjacent to the contacts to inhibit the contact between the battery contact 222 and the incorrect side of a battery that is inserted into the battery compartment in the incorrect orientation. For example, the one or more protrusions can be sized and configured to prevent the negative side of a standard cylindrical battery from contacting the battery contact 222 adjacent to the one or more protrusions, while permitting a positive side of such battery to contact the battery contact 222. Generally, with this configuration, the battery can generally only make contact with the contact 222 if the battery is inserted in the battery compartment 220 in the correct orientation, thereby providing polarity protection to the pump assembly 104. The protrusions will preferably be made from a non-conductive material. Alternatively or additionally, the control board 230 can be configured to have polarity protective features or components. Additionally, the control board 230 can have one or more fuses to protect against overpower conditions or surge power conditions.

The pump assembly 104 can have a flow manifold 240 and a one-way flow valve 246 in communication with a fluid flow pathway within the pump assembly 104. The one-way flow valve 246 (also referred to as a check valve) can be a diaphragm valve made from silicone or any other suitable elastomeric or soft material, including without limitation, polyurethane, viton, nitrile rubber, neoprene, Teflon, and other suitable materials. Other suitable valves for the one-way flow valve are, for example and without limitation, umbrella valves, ball valves, reed valves, duckbill valves. In some embodiments, the leakage rate of the one-way flow valve 246 can be approximately 0.05 mL/minute. In some embodiments, the one-way flow valve 246 can be positioned within the pump 232 or in place of one of the valves positioned within the pump 232.

The manifold 240 and/or the one-way flow valve 246 can be in communication with the connector 128. In some embodiments, the one-way flow valve 246 can be supported within the manifold 240, and the manifold 240 can be substantially sealingly coupled with the inlet port or connector 250 on the pump 232 or otherwise supported within the housing 120 so as to be in fluid communication with the inlet port or connector 250. For example, with reference to FIGS. 4A and 4B, the manifold 240 can be assembled with the pump 232 such that the inlet connector 250 is received within the opening 261 formed in the manifold 240. Air and or other gas can exit the pump 232 through outlet port or connector 252. During sterilization, the pump 232 can be configured such that the sterilization gas can penetrate into the internal spaces or chambers of the pump 232, to ensure that the entire pump 232 (both internally and externally) have been sterilized. One or more valves (which can be umbrella valves or any other suitable valve) can be positioned in the pump 232. For example, without limitation, one or more valves can be supported in the pump 232, one being positioned adjacent to each of the inlet port 250 and the outlet port 252.

For optimal sterilization, in some embodiments, the sterilization gas can be introduced slowly to optimize the flow of the sterilization gas through the valves and to prevent the pressure from the sterilization gas from completely closing the valves. As mentioned, the valves (such as the first and second valves) can be configured to be somewhat leaky, thereby permitting the flow of sterilization gas to advance past the valves to sterilize the internal components of the pump 232. For example, the valves can permit a leakage flow rate of fluid therethrough (i.e., flow rate through the valve when the valve is in a closed position) at a rate of between 0.1 mL/min and 10 mL/min or more at nominal or typical working pressures (i.e., at nominal working pressures of the fluid in the conduit) or at nominal or typical sterilization pressures. In some configurations, the portion of the flow pathway between the two valves, or between the valves and the one-way valve, can be the most challenging portion of the flow path or pump assembly 104 to sterilize.

Some embodiments of the pump assembly can have a piezoelectric pump. Some piezoelectric pumps or other pumps disclosed herein can have or can be configured to have orifices to perform the valve functions such that, when the pump is at rest, the flow rate through the pump can be as high as 200 mL/min. Therefore, in some embodiments, where the pump rate can be as high as approximately 300 mL/min or 320 mL/min or otherwise, the first and second valves (which can be orifices) can each have a leakage rate of up to approximately 200 mL/min.

The pump 232 can be of any suitable type such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combinations of the foregoing. The pump 232 can be, for example, a standard off-the-shelf vacuum pump such as the Koge Electronics KPV8A-3A pump. The pump 232 can also be a KNF diaphragm pump or any suitable KNF pump.

Some embodiments of the pump can be as light as approximately 10 grams, or between approximately 6 grams and 15 grams, or between any values within the foregoing range. The pump 232 can have a pump capacity of approximately 500 mL per minute, or between approximately 300 mL per minute or less and approximately 600 mL per minute or more, or between approximately 400 mL per minute and approximately 500 mL per minute, or between any values within the foregoing ranges. In some embodiments, the pump assembly 104 could comprise two or more pumps 232. For example, the pump assembly 104 could have a first pump having a high flow rate, configured to provide a rapid drawdown of the space between the wound overlay and the wound, and a second, smaller capacity pump configured to maintain the level of reduced pressure of the space between the wound overlay and the wound after the initial draw down. In some embodiments, the pump flow rate can be approximately 20 times the leak alarm flow rate, which can be set at approximately 15 milliliters per minute.

As mentioned, the connector 128 can be a threaded connector (as illustrated) that can threadingly receive a mating threaded connector coupled with the end of the tubing 106. The threaded connector 128 can be of a non-standard size as compared to other medical connectors, to prevent a medical practitioner from inadvertently attaching a standard luer connector (such as a connector from an intravenous line) thereto.

Alternatively, not illustrated, the connector 128 can be a standard tubing connector (such as a nipple connector) configured to sealingly receive the tubing thereover such that a separate mating connector on the end of the tubing 106 can be omitted.

The manifold 240 can have a separate port 260 which can be configured to receive a conduit or connector 262 of a pressure monitor. The pressure monitor can be supported by the control board 230 and can be configured to monitor a level of pressure in the fluid flow passageway. The pressure monitor can be configured to protect the motor 232 from exceeding a predefined threshold pressure. In some embodiments, the pressure monitor can be calibrated to not exceed 175+/−50 mmHg. In some embodiments, the pressure monitor can be calibrated to not exceed 235 mmHg. The pressure monitor can be configured to cut power to the motor if the pressure reading reaches a predetermined value, and be configured to resume when the pressure level drops below the predetermined value or a second predetermined value that can be higher or lower than the first predetermined value. Additionally, the pump assembly 104 can be programmed to prevent such over-pressurization. The pump assembly 104 can be configured such that the software provides the primary mechanism for preventing over-pressurization, and the pressure monitor can provide backup over-pressurization protection.

The pump 232 can have a layer of open foam or other material wrapped at least partially around an outside surface of the pump 232 to reduce the noise and vibration produced by the pump 232. All of these components can be supported within the first and second pump housing members 120a, 120b, which can be secured together with any suitable fasteners 270 (for example, a pair of screws). One or more labels 270 can be affixed to an outside surface of the housing 120. Additionally, in some embodiments, the pump 232 can have one or more weights, cushions, foam (such as a viscoelastic foam), plastic (such as ABS, polyurethane, urethane, or otherwise), or other pads, panels, sheets, or segments supported by the pump 232 or positioned adjacent to one or more outside surfaces of the pump. Some embodiments can have mass based or compliant damping materials. Such components or materials (not illustrated) can damp vibration and/or attenuate noise produced by the pump.

For example, one or more weights (made from steel, metal, or any other suitable material) can be supported or attached to an outside surface of the pump 232 or any other pump embodiment disclosed herein. The steel weights can weigh approximately 1.8 grams, 3.8 grams, or 5.8 grams, or between 1 gram and 10 grams or more, or between 1.5 grams and 6 grams. Two or more weights can be supported or attached to an outside surface of the pump 232 or any other pump embodiment disclosed herein. Two steel weights each weighing approximately 1.8 grams, 3.8 grams, or 5.8 grams, or between 1 gram and 10 grams or more, or between 1.5 grams and 6 grams, can be attached to an outside surface of the pump 232. Each of the two plates can be positioned on opposite sides of the motor 232, or otherwise. In some embodiments, four steel weights each weighing approximately 1.8 grams, 3.8 grams, or 5.8 grams, or between 1 gram and 10 grams or more, or between 1.5 grams and 6 grams, can be attached to an outside surface of the pump 232. The plates can be arranged such that two plates are positioned on each of two opposite sides of the motor 232, or otherwise. In some embodiments, weights can be positioned adjacent to three or more sides of the pump 232 including, for example and without limitation, the sides and top surfaces of the pump 232.

With reference to FIG. 4A, the battery cover 124 can have a latch or tab member 124a that can be configured to engage with mating feature on the housing 120 to inhibit the battery cover 124 from becoming inadvertently opened when in the closed position. Additionally, guides or protrusions 124b can be formed on the battery cover 124 to facilitate the ease with which the battery cover 124 can be opened and closed. The guides 124b can engage mating guides or channels 120c formed in the housing 120. The battery cover 124 can be configured to have a gripping surface, for single finger use. For example, without limitation, a plurality of depressions 124c can be formed on a surface of the battery cover 124 to enhance the grip between a user's finger or other object and the batter cover 124, to facilitate the opening and closing of the battery cover 124.

With reference to FIG. 4B, the battery cover 124 can support one or more battery contacts or terminals 125 thereon, configured to provide a connection between the two batteries. The battery cover 124 can further support one or more protrusions 124d adjacent to the battery contact 125. The one or more protrusions 124d can be sized and configured to prevent the negative side of a standard cylindrical battery from contacting the battery contact 125 adjacent to the one or more protrusions 124d, while permitting a positive side of such battery to contact the battery contact 125. With this configuration, the battery can generally only make contact with the contact 125 if the battery is inserted in the battery compartment 220 in the correct orientation, thereby providing polarity protection to the pump assembly 104.

With reference to FIGS. 4A and 4B, the housing 120 can have one or more tabs 121 and depressions or channels 123 configured to receive the tabs 121 to improve the connection between the two members 120a, 120b of the housing. The tabs 121 and depressions 123 can hold the edges of the housing 120 together better to improve the strength of the housing 120 and to make the connection tighter between the two members 120a, 120b of the housing. The control board 230 can be assembled to the housing 12 with similar features.

As described in U.S. patent application Ser. No. 13/092, 042, which disclosure is hereby incorporated by reference as if fully set forth herein, a lower surface of any of the wound dressing 102 embodiments disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

The perforations can be sized small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer helps hold the whole wound dressing together and helps to create an air tight seal around the absorbent pad in order to maintain negative pressure at the wound. The wound contact layer also acts as a carrier for an optional lower and upper adhesive layer (not shown). For example, a lower pressure sensitive adhesive can be provided on the underside surface 101 of the wound dressing whilst an upper pressure sensitive adhesive layer can be provided on the upper surface 103 of the wound contact layer. The pressure sensitive adhesive, which can be a silicone, hot melt, hydrocolloid or acrylic based adhesive or other such adhesives, can be formed on both sides or optionally on a selected one or none of the sides of the wound contact layer. When a lower pressure sensitive adhesive layer is utilized this helps adhere the wound dressing to the skin around a wound site.

As mentioned, any dressing embodiments for use in the dressing kits disclosed or incorporated by reference herein can have an adhesive covered bottom (e.g., wound contacting) surface. In some embodiments, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation may be a mixture of alkyl pendant siloxanes, which can be spread and cast as a two part mix with a catalyst such that a final polymerisation step takes place following casting or spreading. In some embodiments, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of some embodiments of such an arrangement can be between approximately 367 $gm^{-2}/24$ hrs to approximately 405 $gm^{-2}/24$ hrs, or a mean moisture vapour permeability of 382 $gm^{-2}/24$ hrs.

Some embodiments or arrangements of a silicone adhesive layer suitable for dressing embodiments disclosed herein can have a moisture vapour transmission rate between approximately 350 $gm^{-2}/24$ hrs and approximately 410 $gm^{-2}/24$ hrs. Aptly, the average moisture vapour permeability of some embodiments or arrangements of a silicone adhesive layer suitable for dressing embodiments disclosed herein can be approximately 380 gm$^{-2}$/24 hrs. Some of the dressing embodiments disclosed herein can have a Wacker silres PSA 45 pressure sensitive adhesive coated thereon.

Additionally, any of the dressing embodiments disclosed herein can have an anti-microbial agent or substance incorporated into the dressing or coated on one or more surfaces of the dressing. For example, without limitation, a wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 2008, which application is incorporated by reference herein as if made part of this disclosure, PHMB, chlorohexadine, peroxide, hypochloride, or other bleaches therein or thereon. Further, an absorbent layer of any dressing embodiments disclosed herein can have silver sulphur diazine or any of the previously mentioned substances or active agents therein or thereon. These may be used separately or together. These respectively can eliminate micro-organisms in the wound and micro-organisms in the absorption matrix. As a still further option, other active components, for example, pain suppressants such as ibuprofen or healing agents can be incorporated into the dressing. Also agents which enhance cell activity, such as growth factors or that inhibit enzymes, such as matrix metalloproteinase inhibitors, such as tissue inhibitors of metalloproteinase (TIMPS) or zinc chelators, can be incorporated into the dressing. Odor trapping elements such as activated carbon, cyclodextrine, zeolite or the like can also be included in the absorbent layer or other portions or components of the dressing, or above the filter layer.

A layer of porous material can be located above the wound contact layer. This porous layer, or transmission layer, allows transmission of fluid including liquid and gas away from a wound site into upper layers of the wound dressing. In particular, the transmission layer can ensure that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer can be formed of a material having a three dimensional structure. For example, a knitted or woven spacer fabric (for example Baltex 7970 weft knitted polyester) or a non-woven fabric can be used. Other materials can be utilized, and examples of such materials are described in U.S. patent application Ser. No. 13/092,042, which are hereby incorporated by reference and made part of this disclosure.

In some embodiments, the transmission layer can have a 3D polyester spacer fabric layer. This layer can have a top layer (that is to say, a layer distal from the wound-bed in use) which is a 84/144 textured polyester, and a bottom layer (that is to say, a layer which lies proximate to the wound bed in use) which can be a 100 denier flat polyester and a third layer formed sandwiched between these two layers which is a region defined by a knitted polyester viscose, cellulose or the like monofilament fiber. Other suitable materials and other linear mass densities of fiber can be used.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Again, as described in greater detail in U.S. patent application Ser. No. 13/092,042, a layer of absorbent material can be provided above the transmission layer. The absorbent material which can be a foam or non-woven natural or synthetic material and which can optionally include or be superabsorbent material forms a reservoir for fluid, particularly liquid, removed from the wound site and draws those fluids towards a cover layer. The material of the absorbent layer can prevent liquid collected in the wound dressing from flowing in a sloshing manner. The absorbent layer can also help distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer can be manufactured from ALLEVYN™ foam, Freudenberg 114-224-4 and/or Chem-Posite™ 11C-450, or any other suitable material.

In some embodiments, the absorbent layer can be a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing. The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimized for wound healing.

In some embodiments, the absorbent layer can be an airlaid material. Heat fusible fibers can optionally be used to assist in holding the structure of the pad together. It will be appreciated that rather than using super-absorbing particles or in addition to such use, super-absorbing fibers can be utilized according to some embodiments of the present invention. An example of a suitable material is the Product ChemPosite™ 11 C available from Emerging Technologies Inc (ETi) in the USA.

Optionally, the absorbent layer can include synthetic stable fibers and/or bi-component stable fibers and/or natural stable fibers and/or super-absorbent fibers. Fibers in the absorbent layer can be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer can comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer can have one or more through holes located so as to underlie the suction port.

The dressing 102 can have a gas impermeable, but moisture vapor permeable, cover layer extending across the width of the wound dressing. The cover layer, which can for example be a polyurethane film (for example, Elastollan SP9109) or any other suitable material having a pressure sensitive adhesive on one side, is substantially gas impermeable, thereby creating a substantially sealed enclosure over the wound. In this way an effective chamber is made between the cover layer and a wound site where a negative pressure can be established. The cover layer can be sealed to the wound contact layer in a border region around the circumference of the dressing, ensuring that no air is drawn in through the border area, for example via adhesive or welding techniques. The cover layer can protect the wound from external bacterial contamination (bacterial barrier) and allows liquid from wound exudates to be transferred through the layer and evaporated from the film outer surface. The cover layer can have a polyurethane film and an adhesive pattern spread onto the film. The polyurethane film is moisture vapor permeable and may be manufactured from a material that has an increased water transmission rate when wet.

An orifice can be provided in the cover film to allow a negative pressure to be applied to the dressing 102. As mentioned, in some embodiments, a suction port 108 can be sealed to the top of the cover film over the orifice, which can communicate negative pressure through the orifice. The port may be adhered and sealed to the cover film using an adhesive such as an acrylic, cyanoacrylate, epoxy, UV curable or hot melt adhesive. The port 108 can be formed from a soft polymer, for example a polyethylene, a polyvinyl chloride, a silicone or polyurethane having a hardness of 30 to 90 on the Shore A scale.

The dressing 102 can have a filter element that is impermeable to liquids, but permeable to gases. The filter element can act as a liquid barrier, to substantially prevent or inhibit liquids from escaping from the wound dressing, as well as an odor barrier. The filter element may also function as a bacterial barrier. In some embodiments, the pore size of the filter element can be approximately 0.2 μm. Suitable materials for the filter material of the filter element include 0.2 micron Gore™ expanded PTFE from the MMT range, PALL Versapore™ 200R, and Donaldson™ TX6628. The filter element thus enables gas to be exhausted through the orifice. Liquid, particulates and pathogens however are contained in the dressing. Other details regarding the filter are disclosed in U.S. patent application Ser. No. 13/092,042 and incorporated by reference herein.

The wound dressing 102 and its methods of manufacture and use as described herein may also incorporate features, configurations and materials described in the following patents and patent applications, each of which is incorporated by reference in their entireties herein as if made part of this disclosure: U.S. Pat. Nos. 7,524,315, 7,708,724, and 7,909,805; U.S. Patent Application Publication Nos. 2005/0261642, 2007/0167926, 2009/0012483, 2009/0254054, 2010/0160879, 2010/0160880, 2010/0174251, 2010/0274207, 2010/0298793, 2011/0009838, 2011/0028918, 2011/0054421, and 2011/0054423; as well as U.S. application Ser. No. 12/941,390, filed Nov. 8, 2010, Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure may be substituted, added or implemented into embodiments of the present application.

In operation, the wound dressing 102 is sealed over a wound site forming a wound cavity. The pump assembly 104 provides a source of a negative pressure to the dressing 102. Fluid is drawn towards the orifice through the wound dressing from a wound site below the wound contact layer. The fluid moves towards the orifice through the transmission layer. As the fluid is drawn through the transmission layer, wound exudate is absorbed into the absorbent layer.

The general shape of the wound dressing can be square, ovular, rectangular, or otherwise. The dressing can have rounded corner regions. It will be appreciated that wound dressings according to other embodiments of the present invention can be shaped differently such as square, circular or elliptical dressings, or the like.

The desired size of the wound dressing 102 can be selected based on the size and type of wound it will be used in. In some embodiments, the wound dressing 102 can measure between 20 and 40 cm on its long axis, and between 10 to 25 cm on its short axis. For example, dressings can be provided in sizes of approximately 10×20 cm, 10×30 cm, 10×40 cm, 15×20 cm, and 15×30 cm, as described above.

In some embodiments, the wound dressing 102 can be a square-shaped dressing with sides measuring between 15 and 25 cm (e.g., 15×15 cm, 20×20 cm and 25×25 cm). The absorbent layer can have a smaller area than the overall dressing, and in some embodiments may have a length and width that are both about 3 to 10 cm shorter, more preferably about 5 cm shorter, than that of the overall dressing 102. In some rectangular-shape embodiments, the absorbent layer may measure between approximately 10 and 35 cm on its long axis, and between 5 and 10 cm on its short axis. For example, absorbent layers can be provided in sizes of 5.6×15 cm or 5×10 cm (for 10×20 cm dressings), 5.6×25 cm or 5×20 cm (for 10×30 cm dressings), 5.6×35 cm or 5×30 cm (for 10×40 cm dressings), 10×15 cm (for 15×20 cm dressings), and 10×25 cm (for 15×30 cm dressings). In some square-shape embodiments, the absorbent layer may have sides that are between 10 and 20 cm in length (e.g., 10×10 cm for a 15×15 cm dressing, 15×15 cm for a 20×20 cm dressing, or 20×20 cm for a 25×25 cm dressing). The transmission layer can be of a smaller size than the absorbent layer, and in some embodiments can have a length and width that are both about 0.5 to 2 cm shorter, more preferably about 1 cm shorter, than that of the absorbent layer. In some rectangular-shape embodiments, the transmission layer may measure between 9 and 34 cm on its long axis and between 3 and 5 cm on its short axis. For example, transmission layers may be provided in sizes of 4.6×14 cm or 4×9 cm (for 10×20 cm dressings), 4.6×24 cm or 4×19 cm (for 10×30 cm dressings), 4.6×34 cm or 4×29 cm (for 10×40 cm dressings), 9×14 cm (for 15×20 cm dressings), and 9×24 cm (for 15×30 cm dressings). In some square-shape embodiments, the transmission layer may have sides that are between 9 and 19 cm in length (e.g., 9×9 cm for a 15×15 cm dressing, 14×14 cm for a 20×20 cm dressing, or 19×19 cm for a 25×25 cm dressing).

The dressing can contain anti-microbial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like may be included in the absorbent layer or as a still further layer above the filter layer.

Whilst some embodiments of the present invention have so far been described in which the transmission layer is formed as a 3D knit layer, e.g., two layers spaced apart by a monofilament layer, it will be appreciated that some embodiments of the present invention are not restricted to the use of such a material. In some embodiments, as an alternative to such a 3D knit material, one or more layers of a wide variety of materials could be utilized. In each case, according to embodiments of the present invention, the openings presented by layers of the transmission layer are wider and wider as one moves away from the side of the dressing which, in use will be located proximate to the wound. In some embodiments, the transmission layer may be provided by multiple layers of open celled foam. In some embodiments, the foam is reticulated open cell foam. The foam can be hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In some embodiments, two, three, four or more foam layers may be included. The foam layers may be integrally formed, for example, by selecting a foam having a large pore size and then repeatedly dipping this to a lesser and lesser extent into material which will clog the pores or alternatively, the transmission layer formed by the multiple foam layers may be provided by laminating different types of foam in a layered arrangement or by securing such layers of foam in place in a known manner.

Figure 7A:
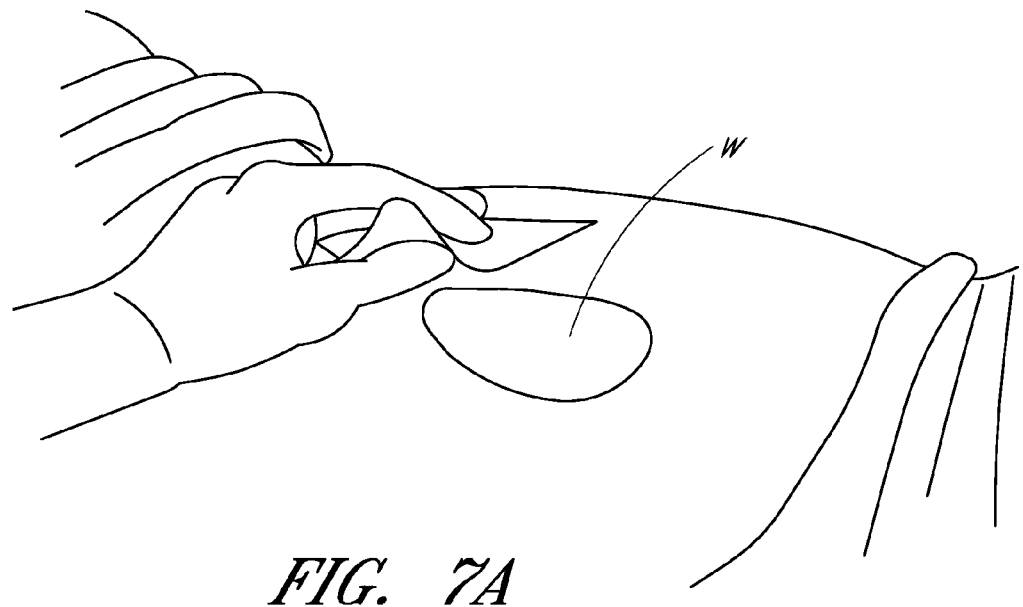
FIGS. 7A-7D illustrate the use of an embodiment of a TNP wound treatment system being used to treat a wound site on a patient.

FIGS. 7A-7D illustrate the use of an embodiment of a TNP wound treatment system being used to treat a wound site on a patient. FIG. 7A shows a wound site W being cleaned and prepared for treatment. Here, the healthy skin surrounding the wound site W is preferably cleaned and excess hair removed or shaved. The wound site W may also be irrigated with sterile saline solution if necessary. Optionally, a skin protectant may be applied to the skin surrounding the wound site W. If necessary, a wound packing material, such as foam or gauze, may be placed in the wound site W. This may be preferable if the wound site W is a deeper wound.

Figure 7B:
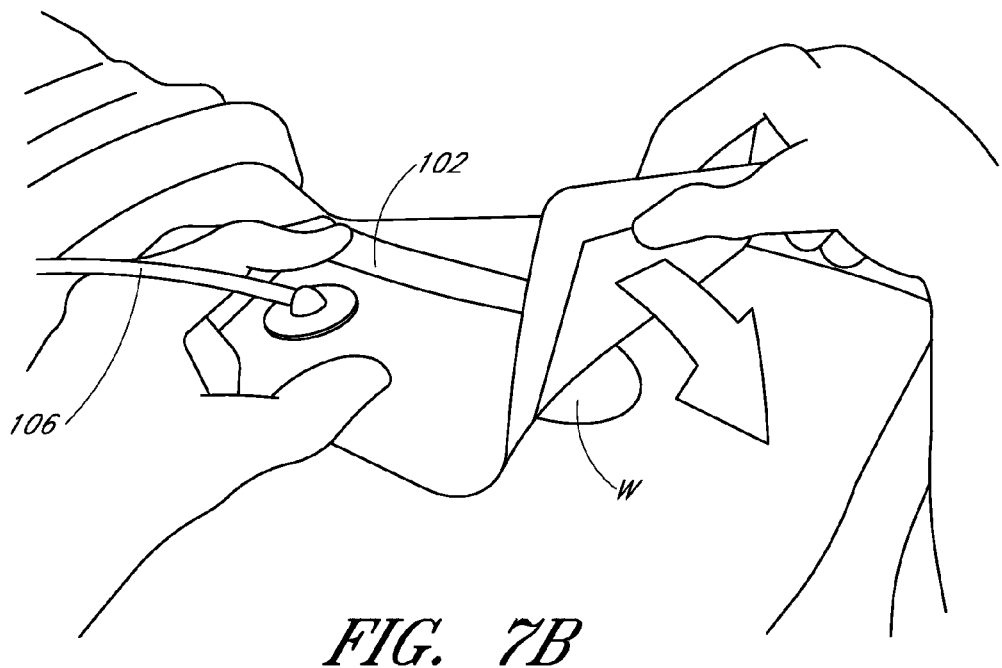

After the skin surrounding the wound site W has been prepared, the cover 151 can be removed from the first packaging element 150 to provide access to the components. The dressing 102 can be removed from the packaging 150 and, as illustrated in FIG. 7B, be positioned and placed over the wound site W. The wound dressing 102 can be placed with the wound contact layer of the dressing 102 over and/or in contact with the wound site W. In some embodiments, an adhesive layer can be provided on a lower surface of the wound contact layer, which may in some cases be protected by an optional release layer to be removed prior to placement of the wound dressing 102 over the wound site W. The dressing 102 can be positioned such that the port 108 is in a raised position with respect to the remainder of the dressing 102 so as to avoid fluid pooling around the port 108. In some embodiments, the dressing 102 is positioned so that the port 108 is not directly overlying the wound, and is level with or at a higher point than the wound. To help ensure adequate sealing for TNP, the edges of the dressing 102 can be smoothed over to avoid creases or folds. The dressing and the adhesive formed thereon can be configured such that the dressing can be lifted away from the skin or wound and repositioned to remove creases and folds, or to simply reposition the dressing over the wound, or for other reasons, without sacrificing the performance of the adhesive. The tubing 106 can be connected to the dressing 102 either before or after placement of the dressing 102 over the wound.

Figure 7C:
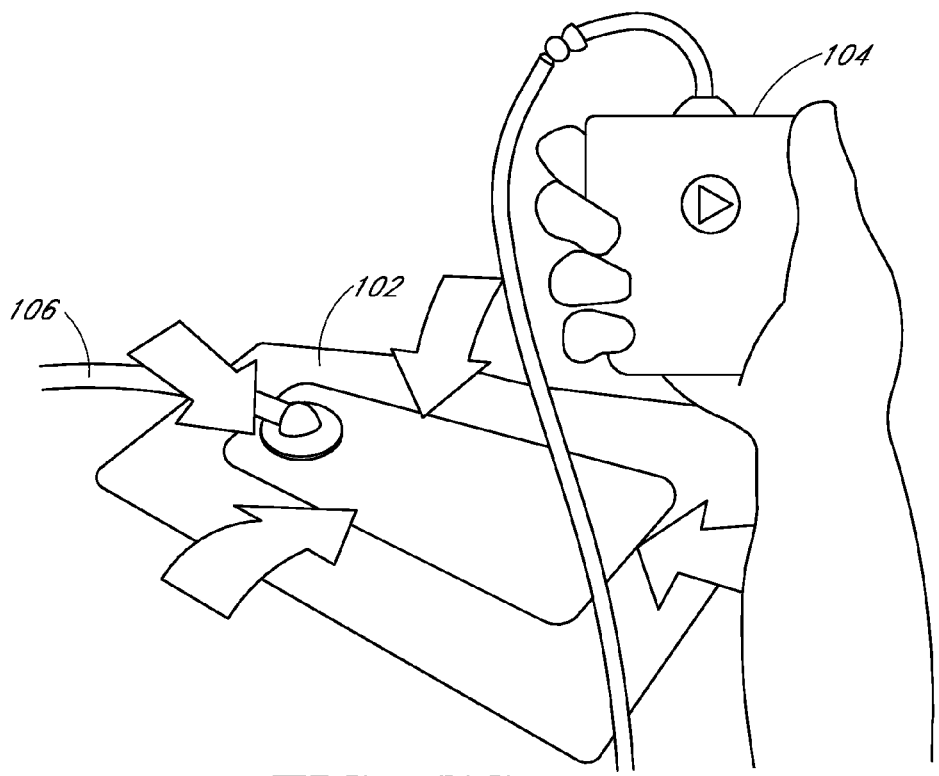

Thereafter, the pump assembly 104 can be removed from the packaging 150 and connected to the tubing 106, as illustrated in FIG. 7C. The batteries 142 can be removed from the packaging 150 and installed in the pump assembly 104 either before or after the pump is attached to the conduit 106. The pump assembly 104 can be configured to apply negative pressure to the wound site via the dressing 102, and typically through the tubing or conduit 106. In some embodiments, a connector may be used to join the conduit 106 to the dressing 102 and to the pump assembly 104. Upon the application of negative pressure with the pump assembly 104, the dressing 102 may in some embodiments partially collapse and present a wrinkled appearance as a result of the evacuation of some or all of the air underneath the dressing 102. In some embodiments, the pump assembly 104 may be configured to detect if any leaks are present in the dressing 102, such as at the interface between the dressing 102 and the skin surrounding the wound site W. Should a leak be found, such leak is preferably remedied prior to continuing treatment. The leak can be remedied by repositioning the dressing 102, smoothing out wrinkles or folds in the dressing, or by applying fixation strips 148 around the periphery of the dressing 102.

Figure 7D:
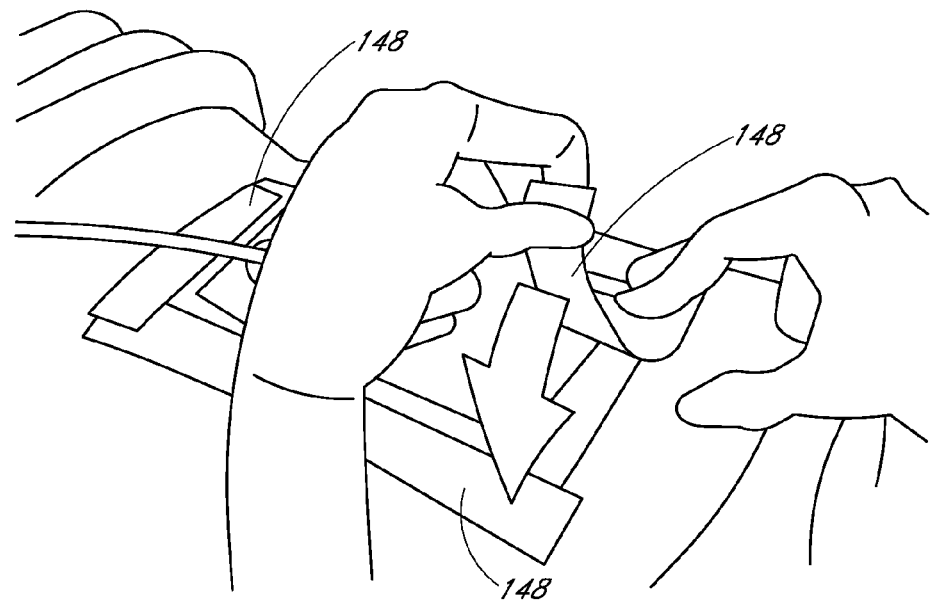
Figure 8A:
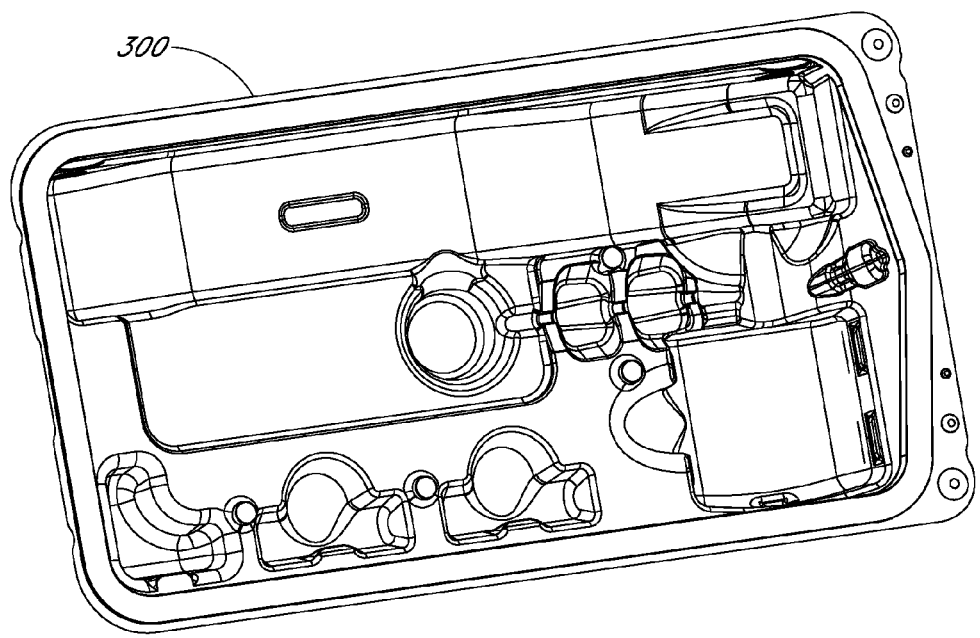
FIGS. 8A-20H are top isometric, bottom isometric, top plane, bottom plane, front, back, first side, and second side views, respectively, of embodiments of packaging elements that can be used with any of the embodiments of the wound dressing apparatuses disclosed herein, including a variety of differently sized wound dressing apparatuses.
Figure 8B:
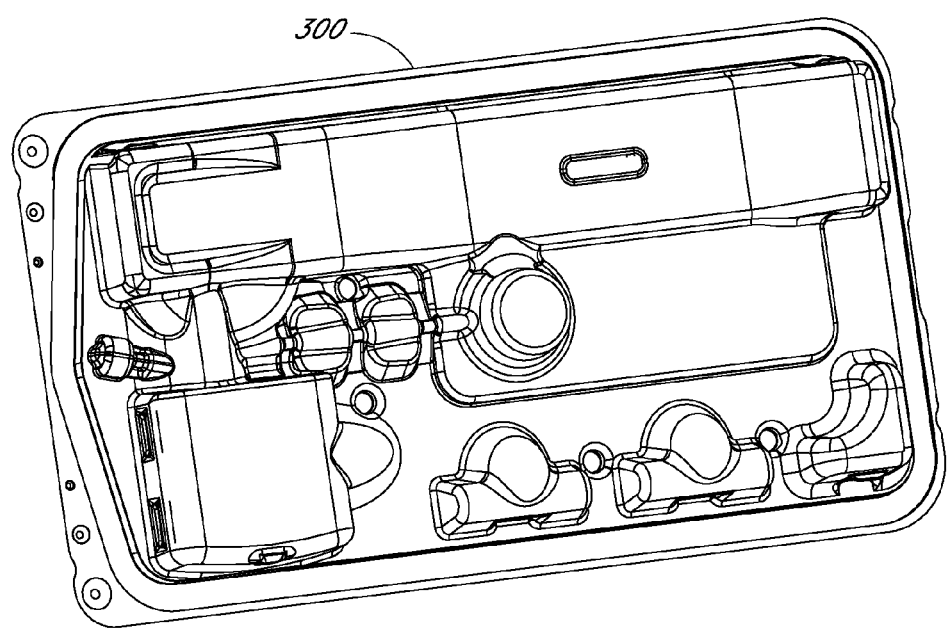
Figure 8C:
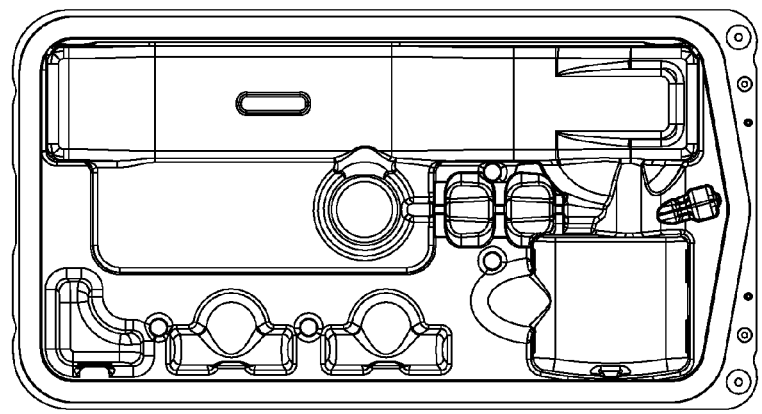
Figure 8D:
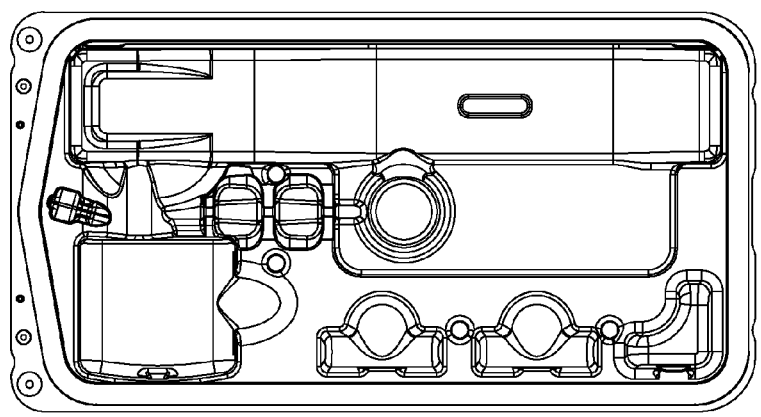
Figure 8E:
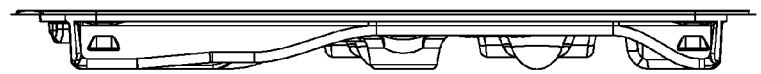
Figure 8F:
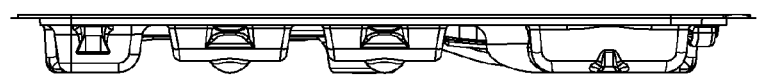
Figure 8G:
Figure 8H:
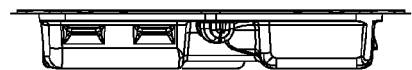
Figure 9A:
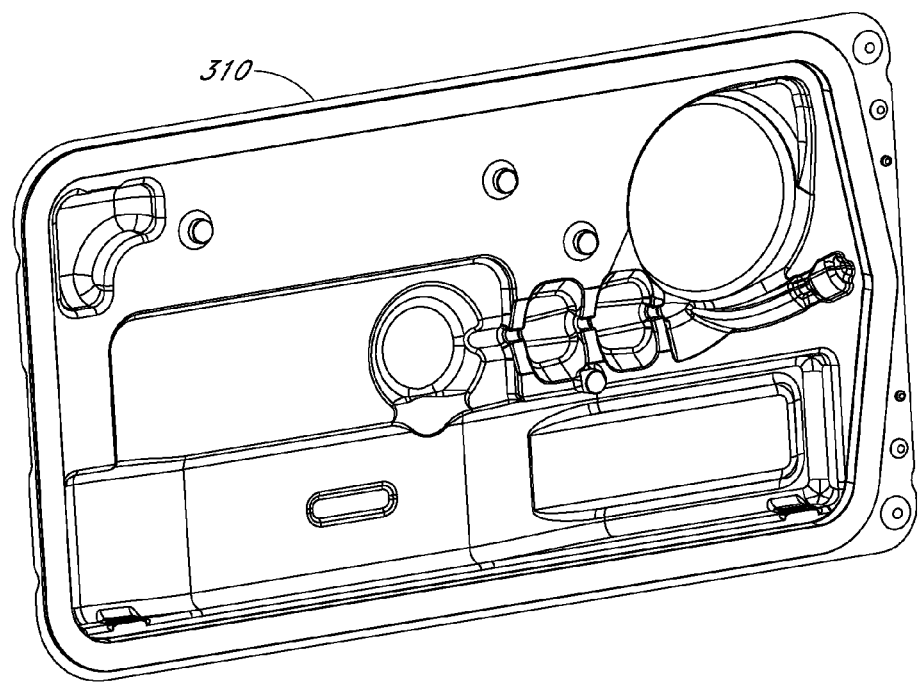
Figure 9B:
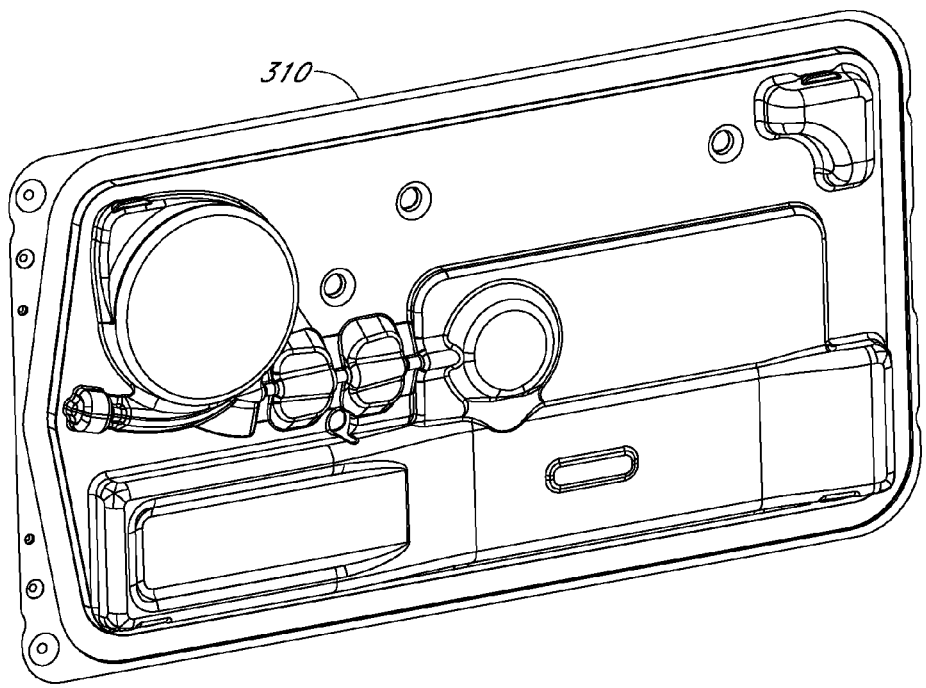
Figure 9C:
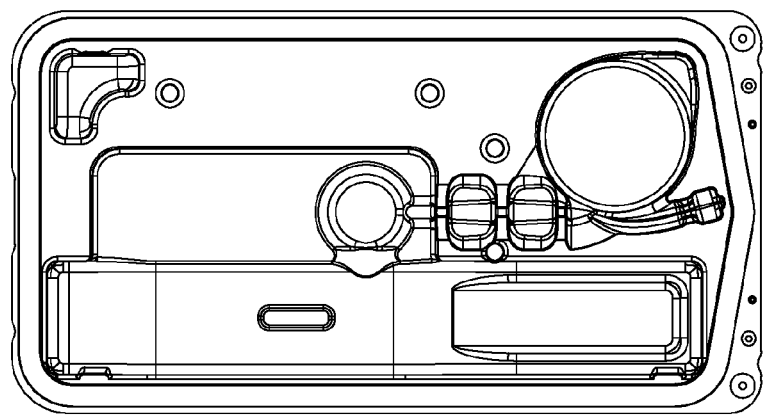
Figure 9D:
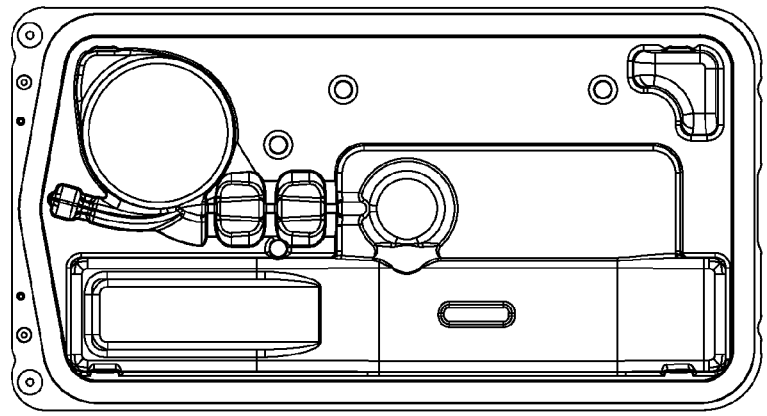
Figure 9E:
Figure 9F:
Figure 9G:
Figure 9H:
Figure 10A:
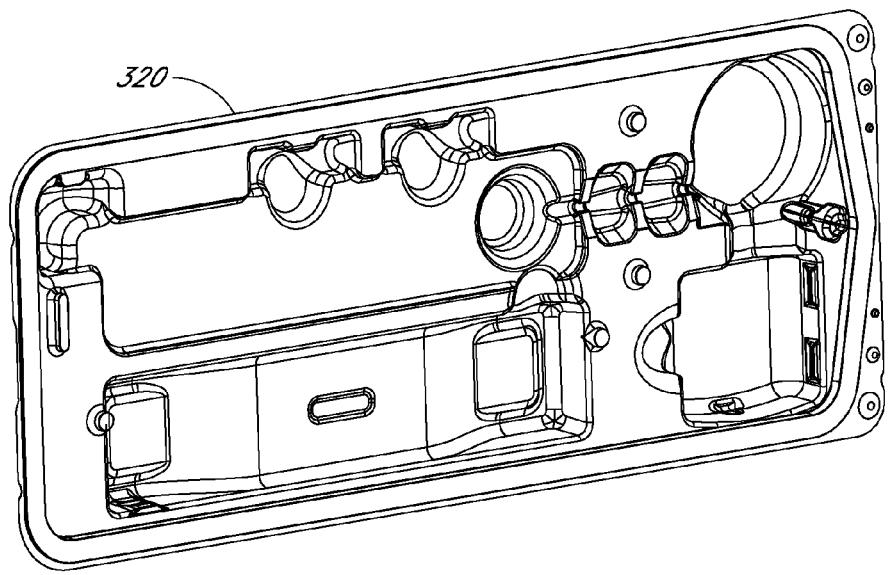
Figure 10B:
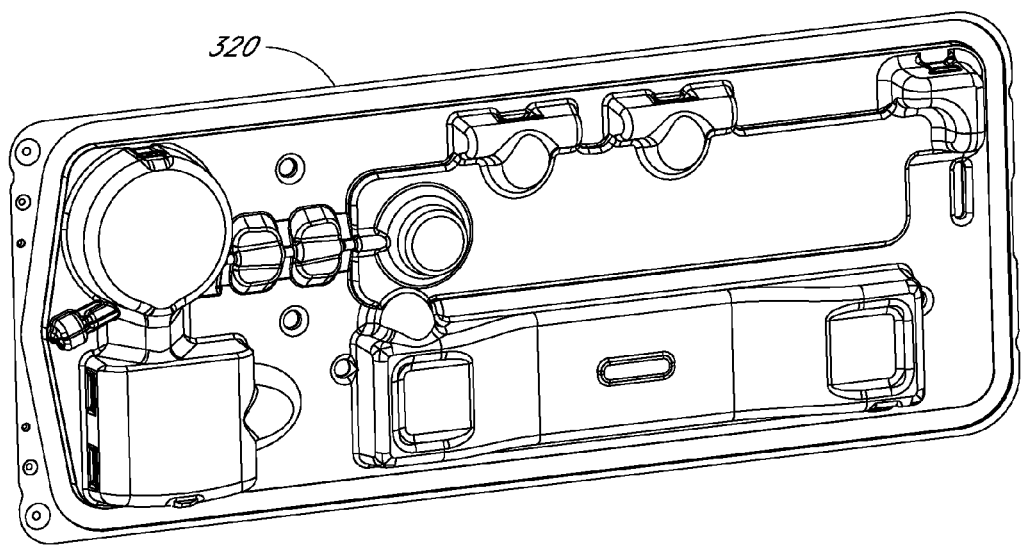
Figure 10C:
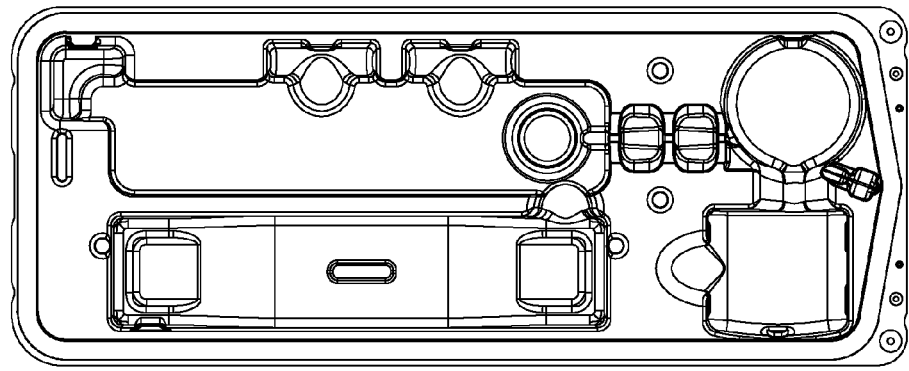
Figure 10D:
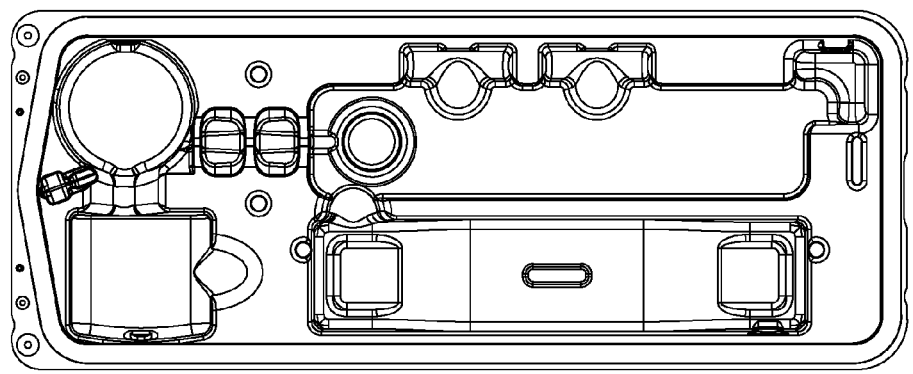
Figure 10E:
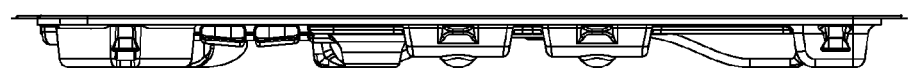
Figure 10F:
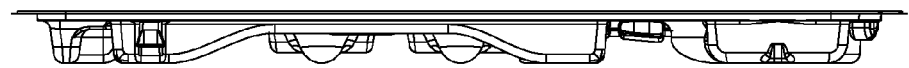
Figure 10G:
Figure 10H:
Figure 11A:
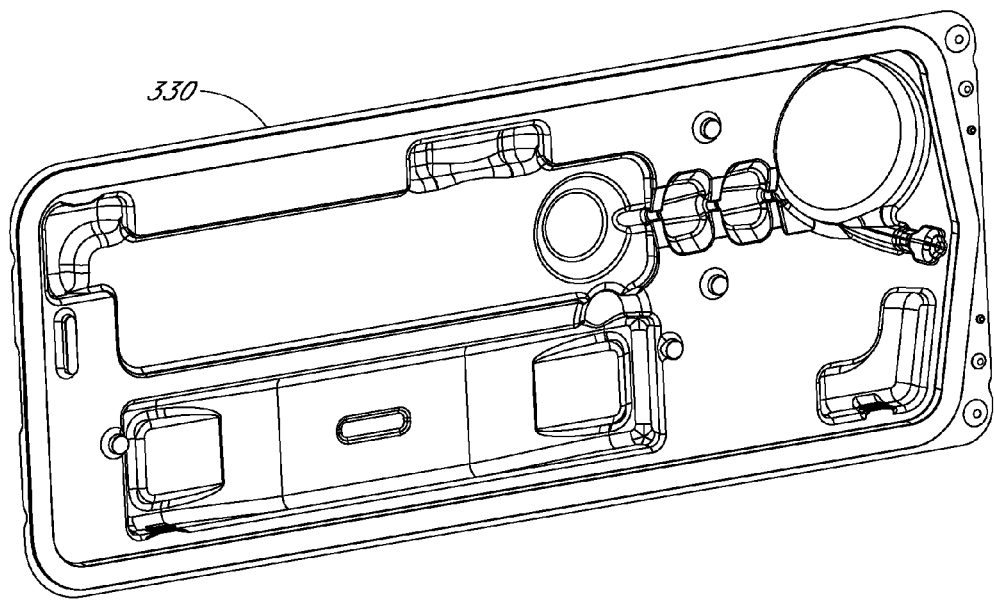
Figure 11B:
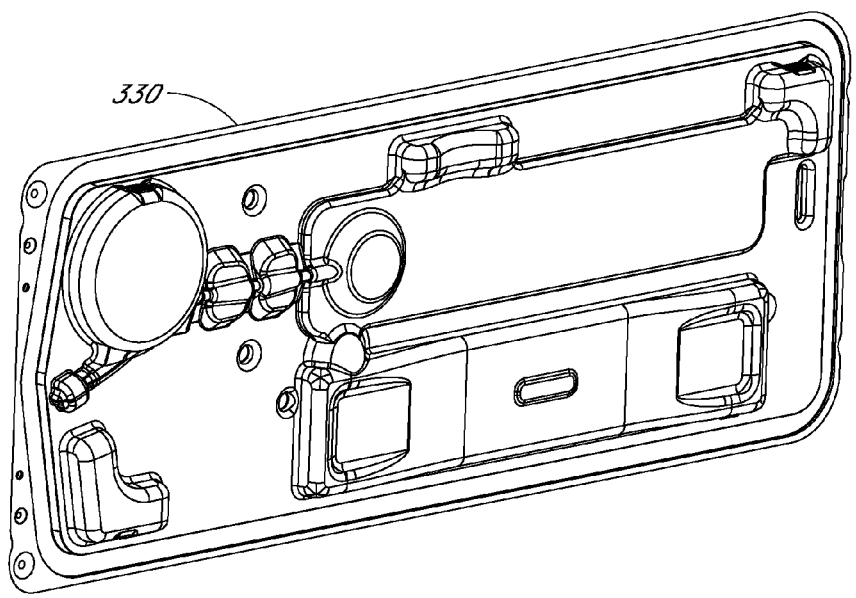
Figure 11C:
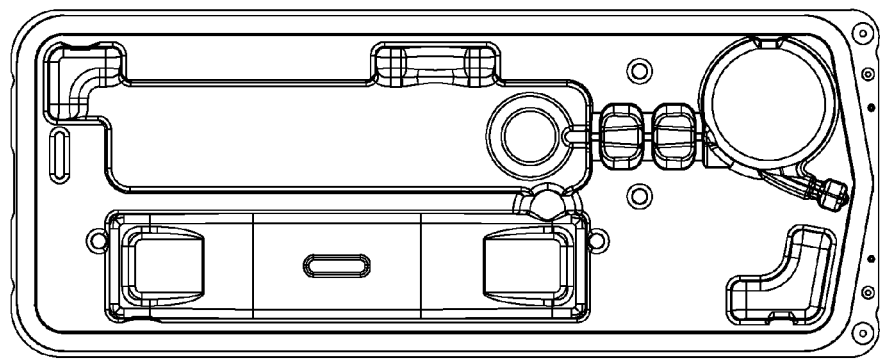
Figure 11D:
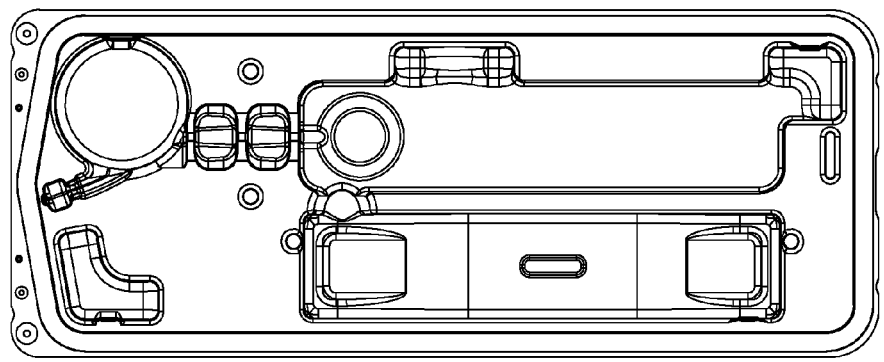
Figure 11E:
Figure 11F:
Figure 11G:
Figure 11H:
Figure 12A:
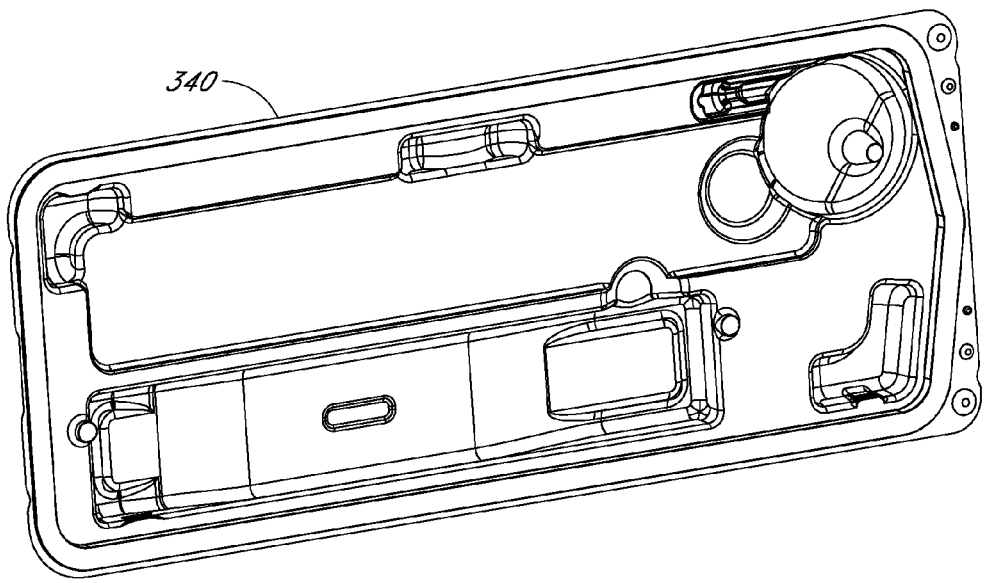
Figure 12B:
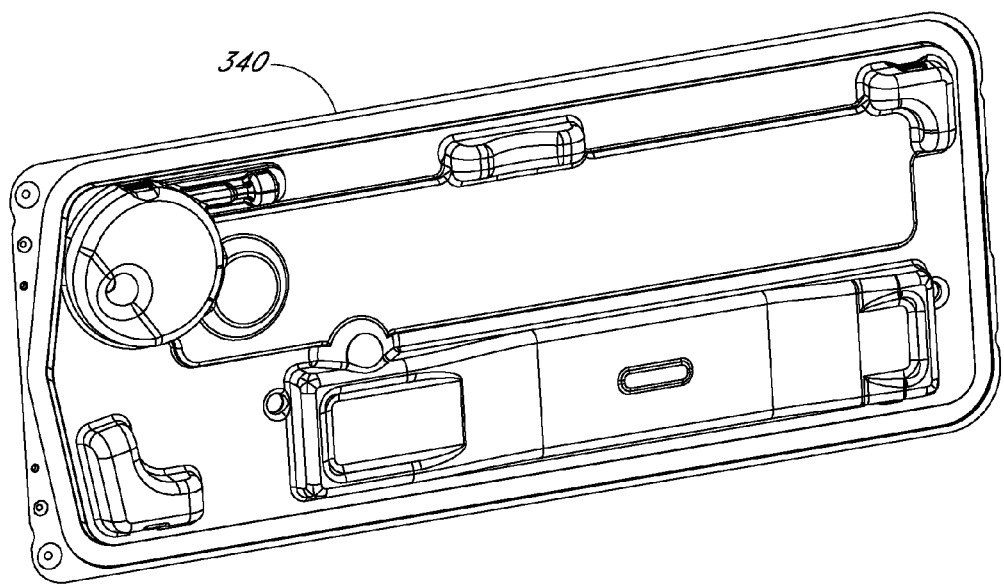
Figure 12C:
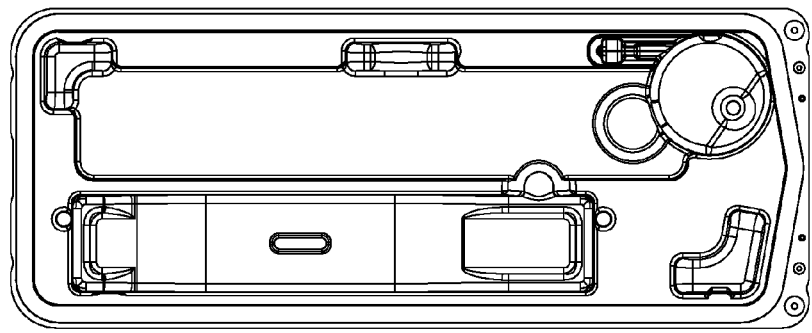
Figure 12D:
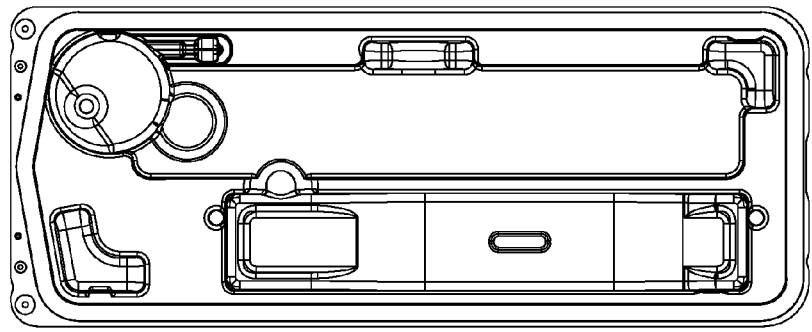
Figure 12E:
Figure 12F:
Figure 12G:
Figure 12H:
Figure 13A:
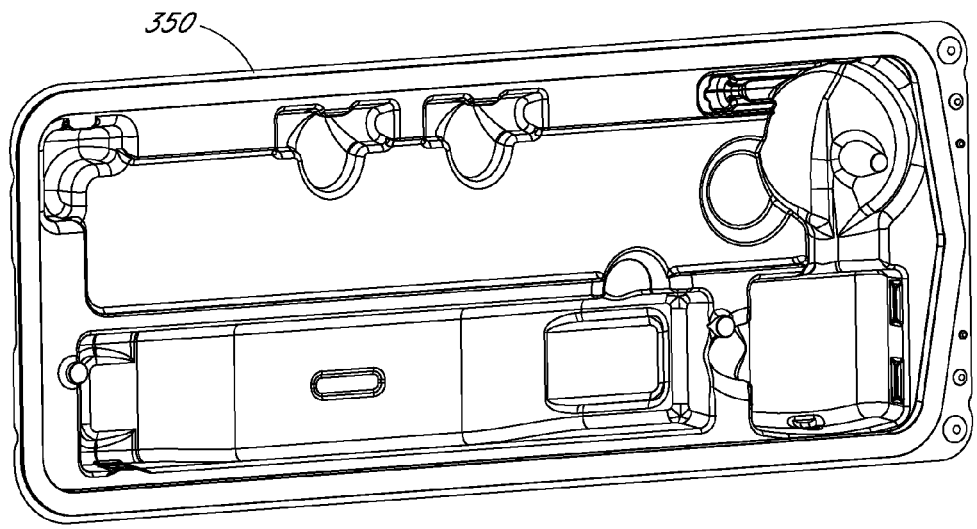
Figure 13B:
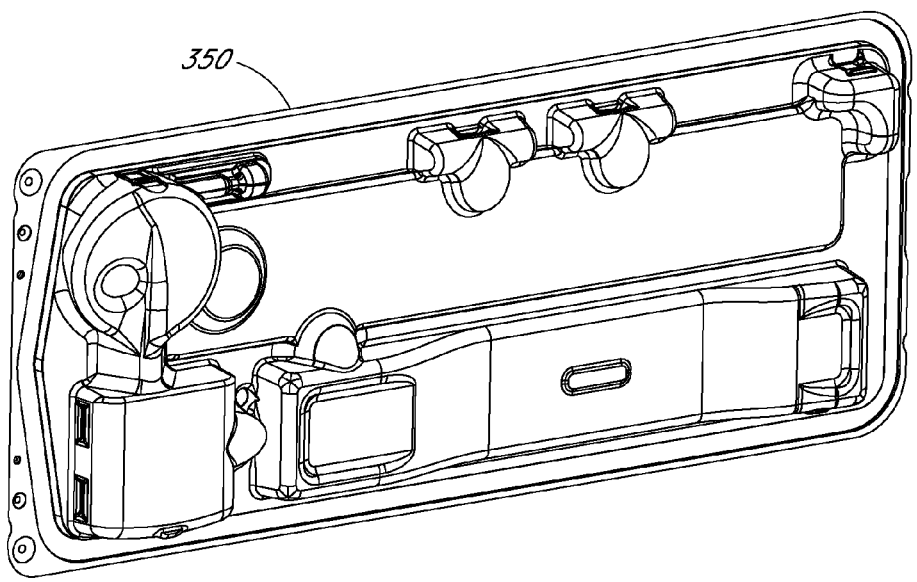
Figure 14A:
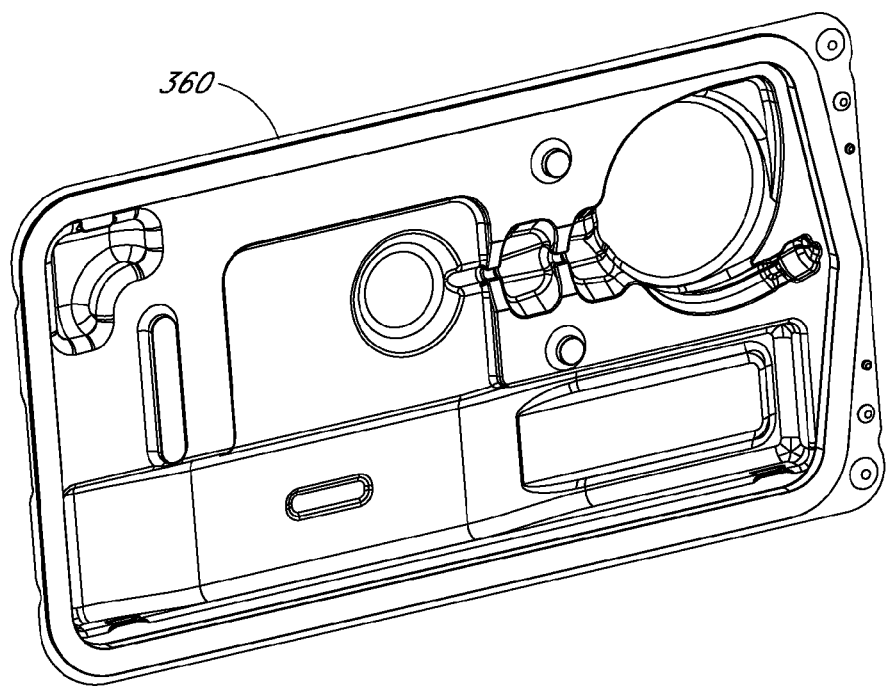
Figure 14B:
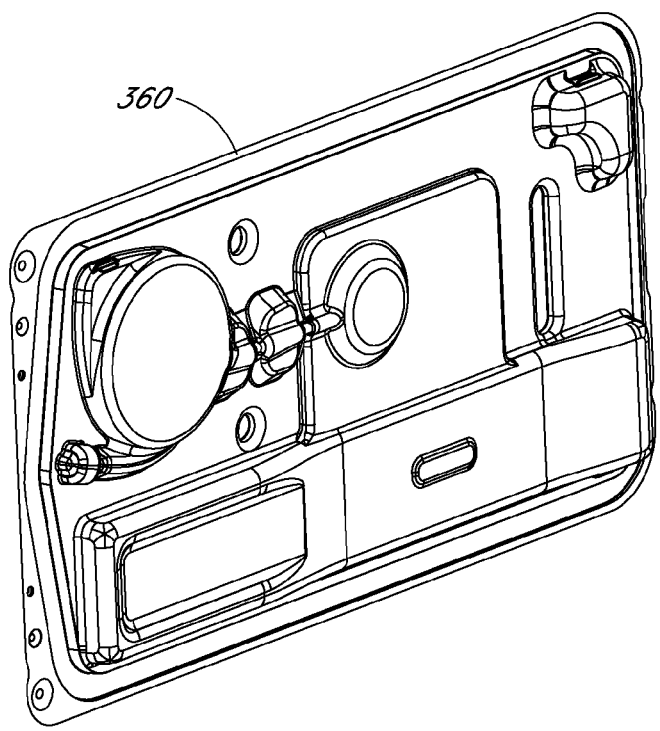
Figure 14C:
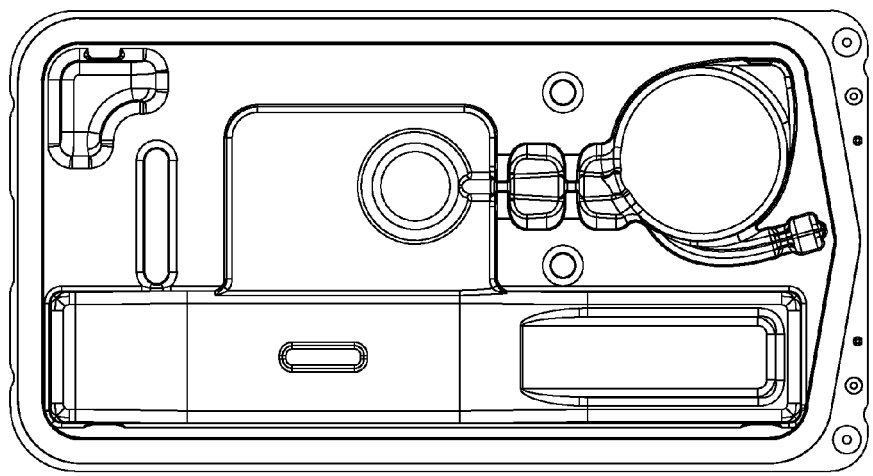
Figure 14D:
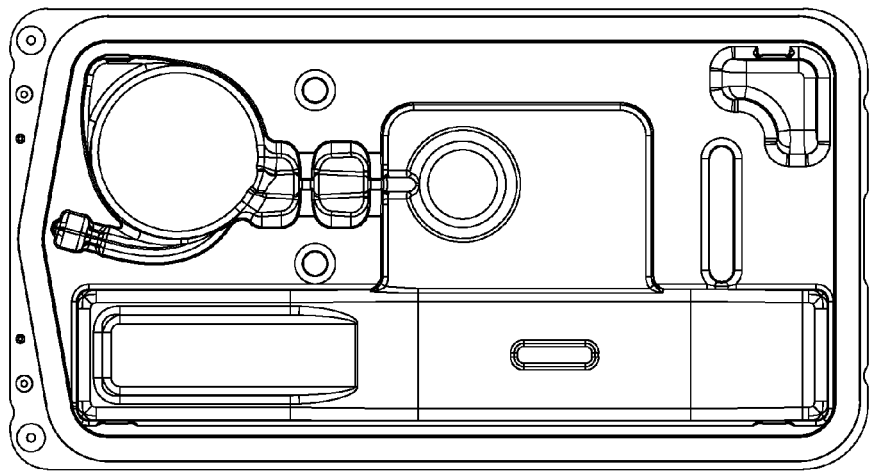
Figure 14E:
Figure 14F:
Figure 14G:
Figure 14H:
Figure 14I:
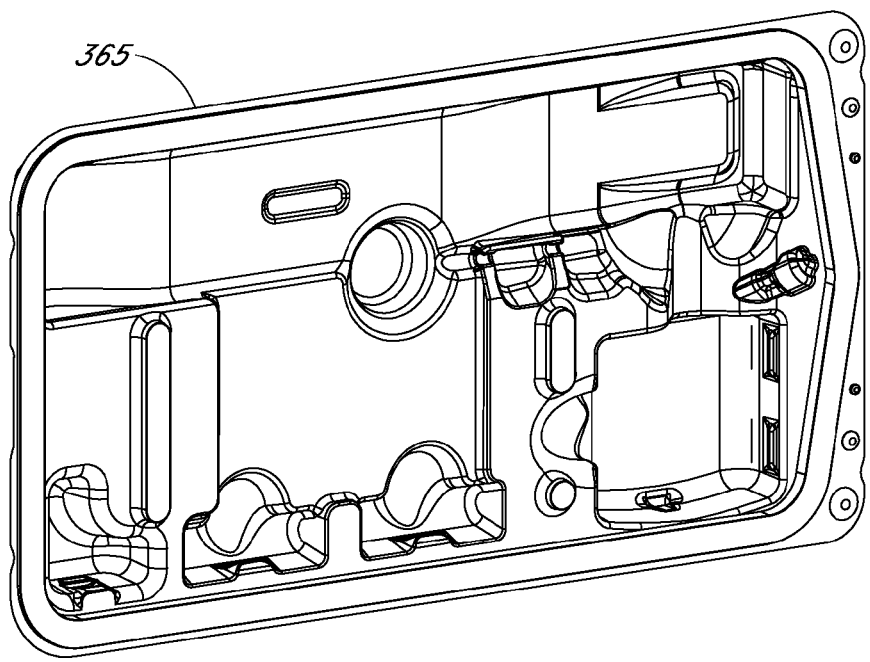
Figure 14J:
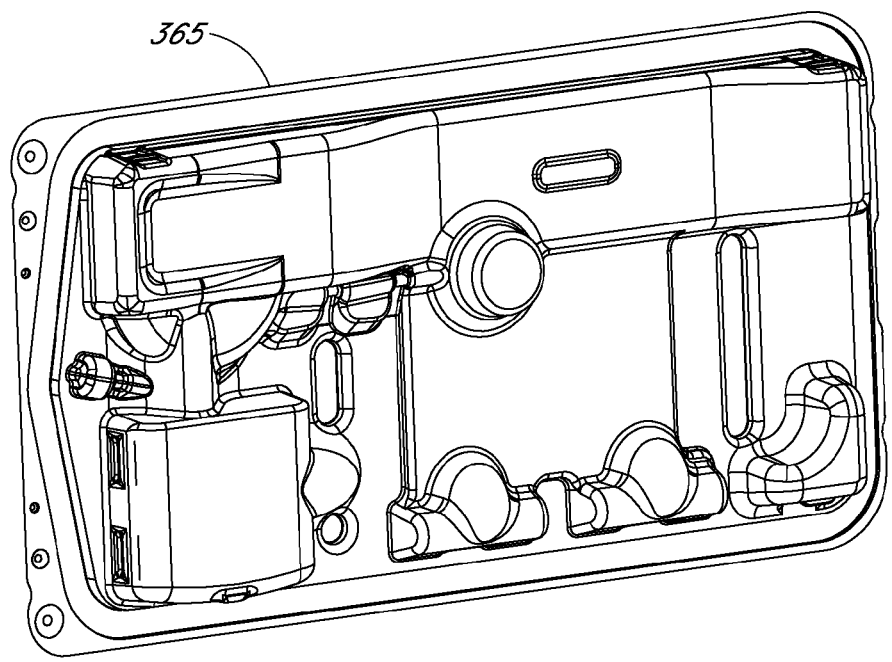
Figure 14K:
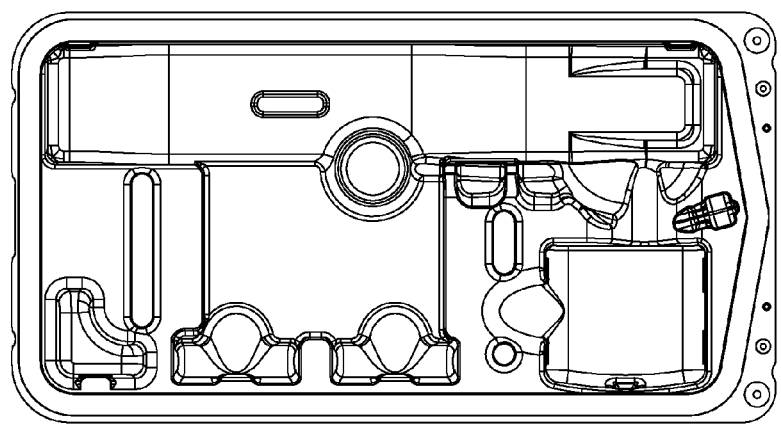
Figure 14L:
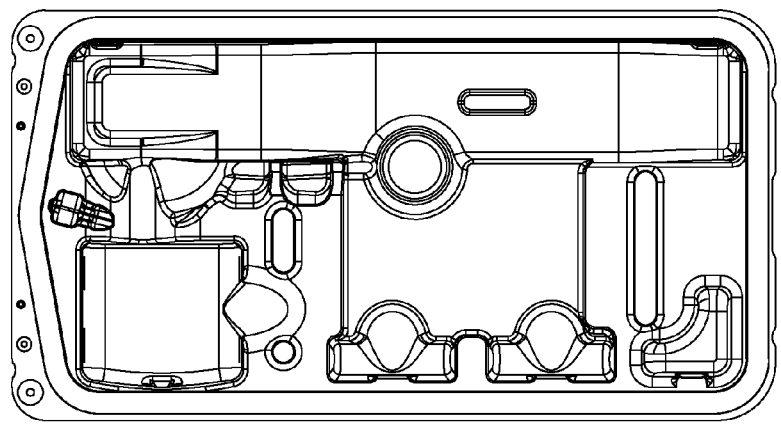
Figure 14M:
Figure 14N:
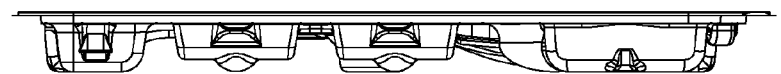
Figure 14O:
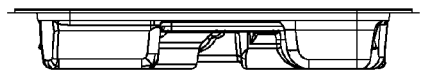
Figure 14P:
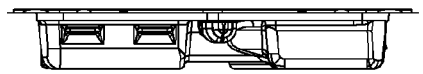
Figure 15A:
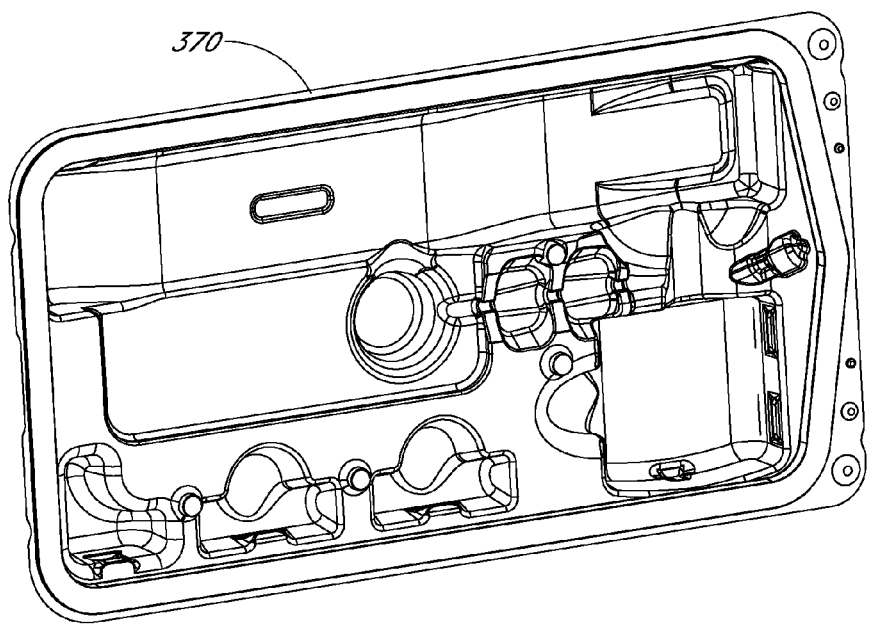
Figure 15B:
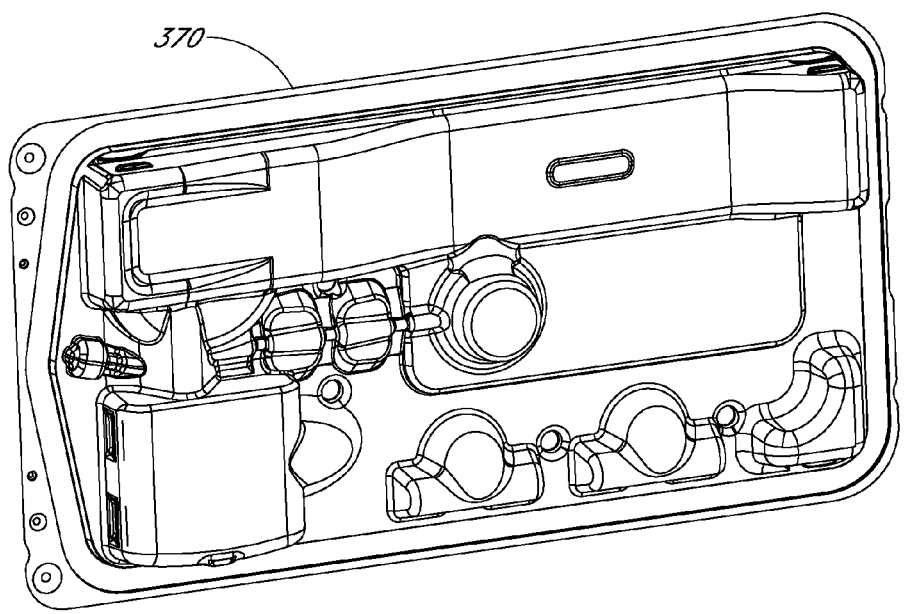
Figure 15C:
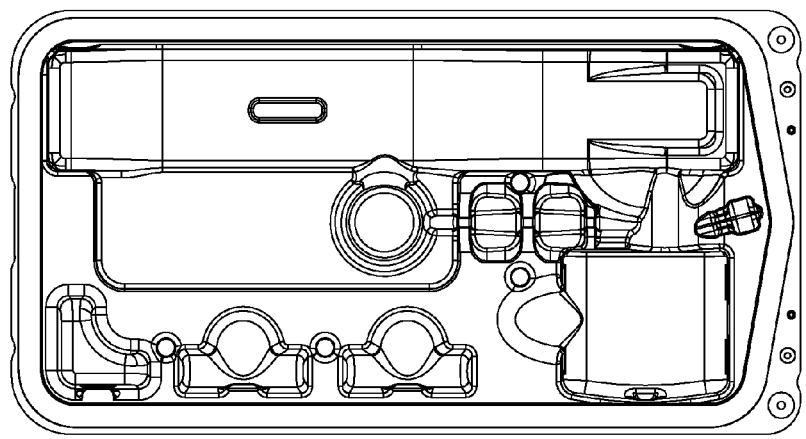
Figure 15D:
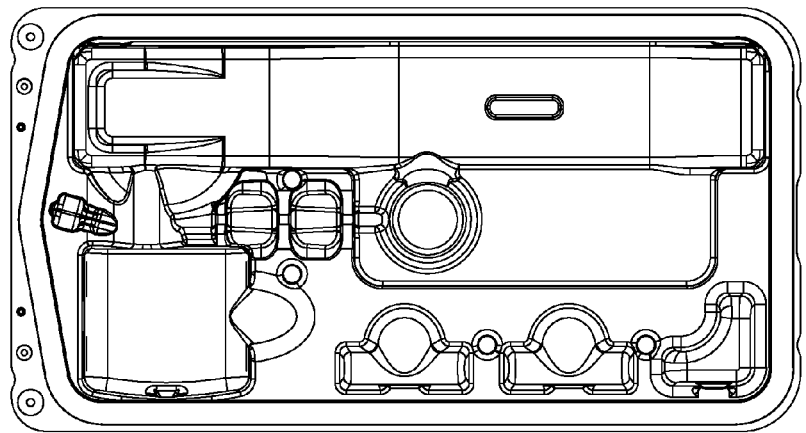
Figure 15E:
Figure 15F:
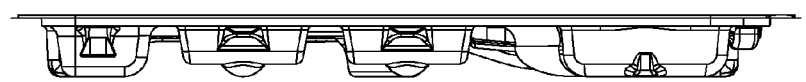
Figure 15G:
Figure 15H:
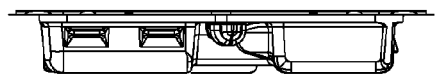
Figure 16A:
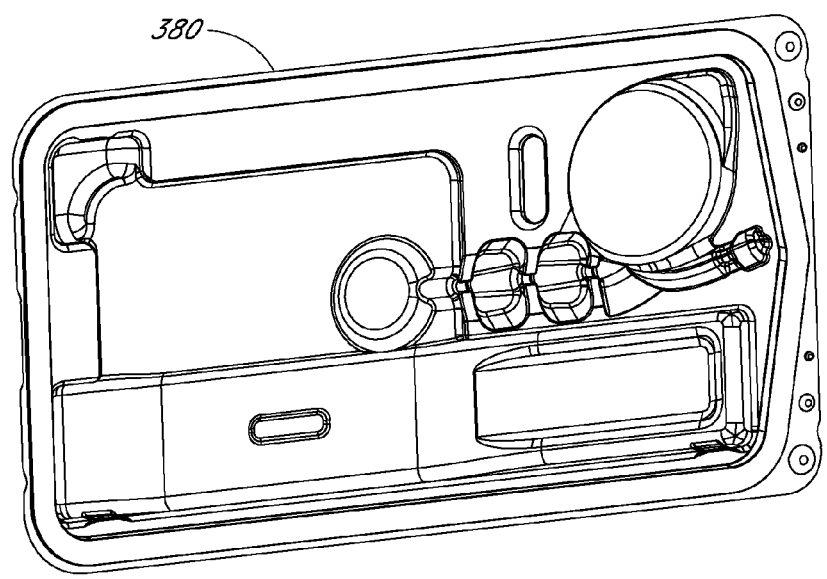
Figure 16B:
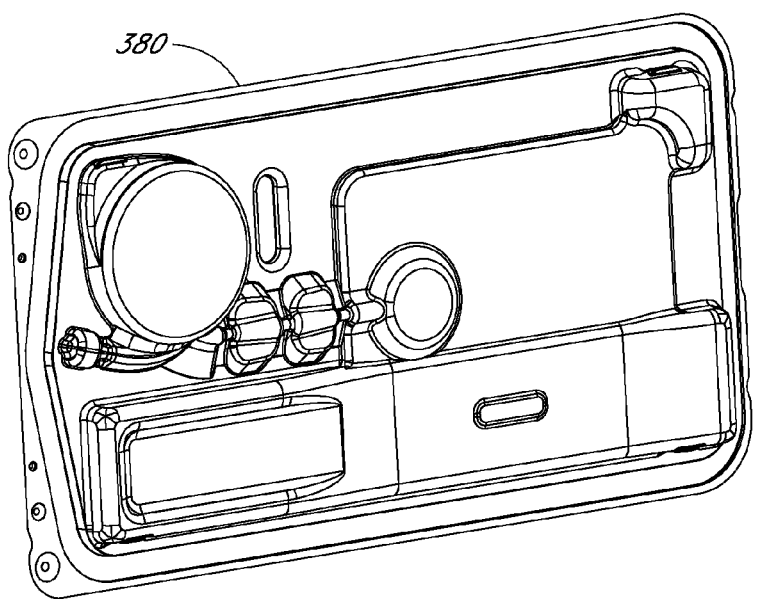
Figure 17A:
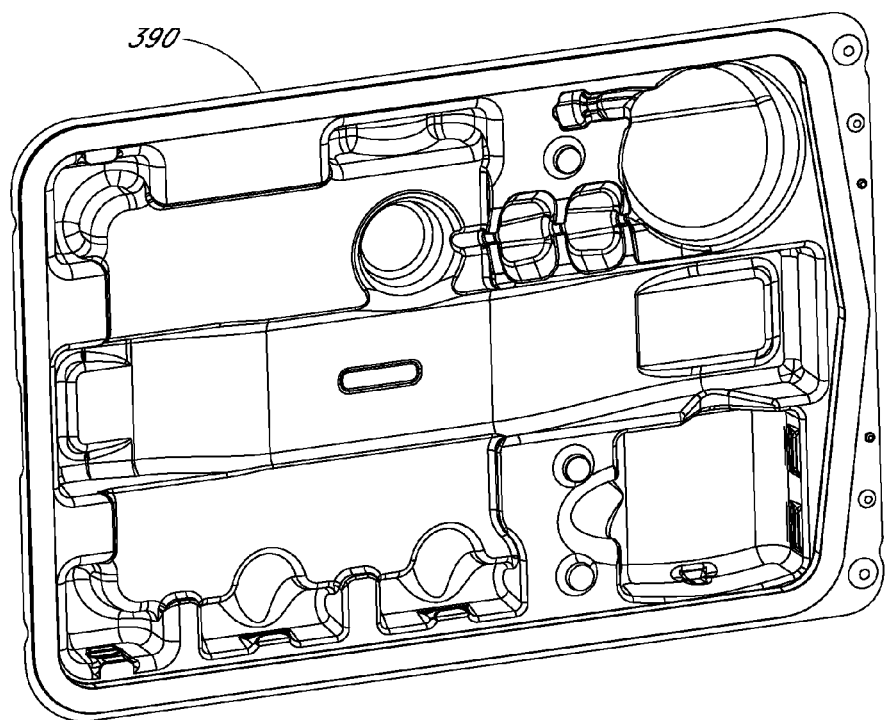
Figure 17B:
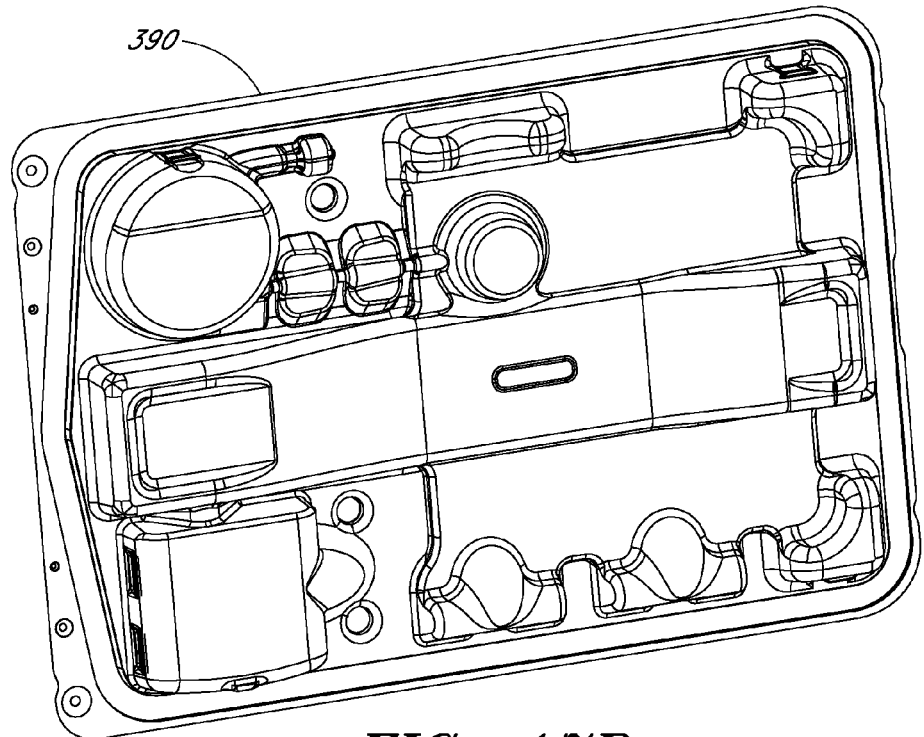
Figure 17C:
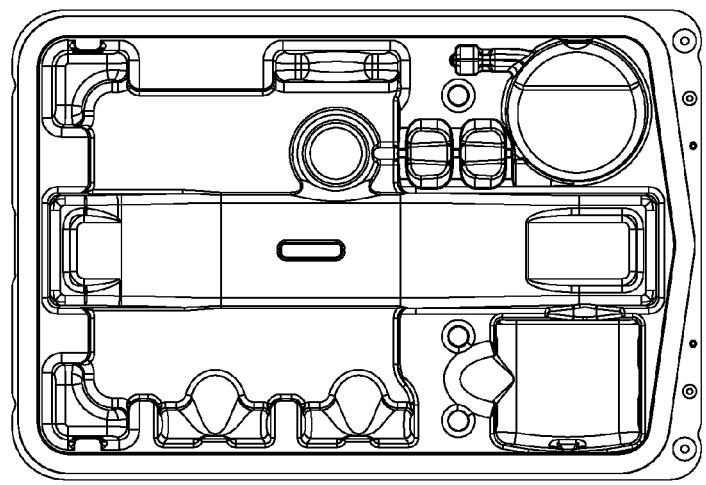
Figure 17D:
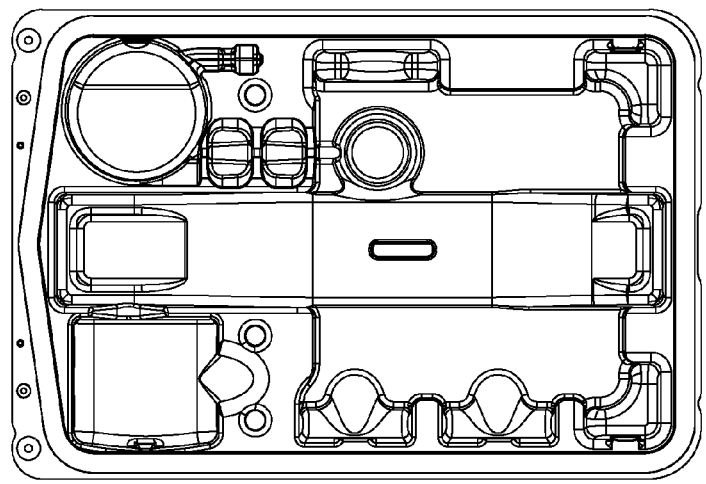
Figure 17E:
Figure 17F:
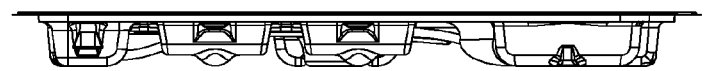
Figure 17G:
Figure 17H:
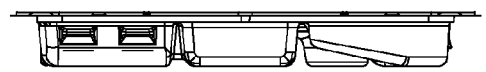
Figure 17I:
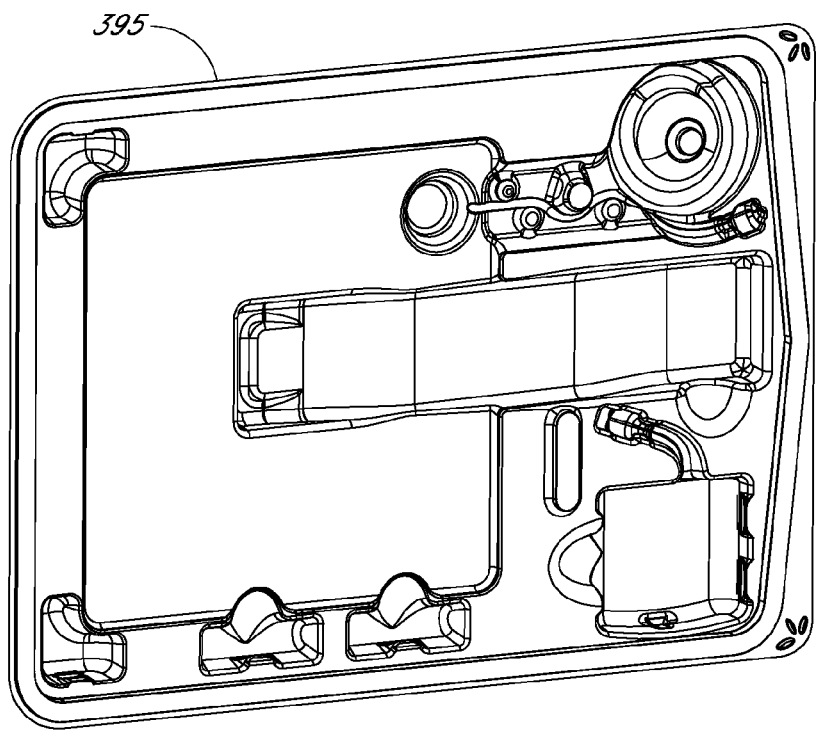
Figure 17J:
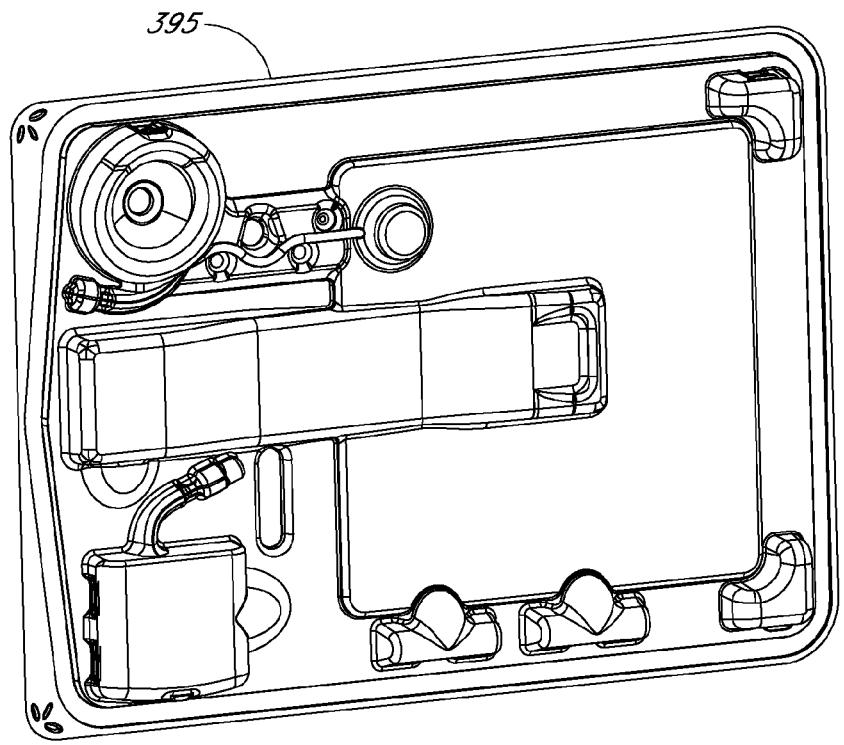
Figure 17K:
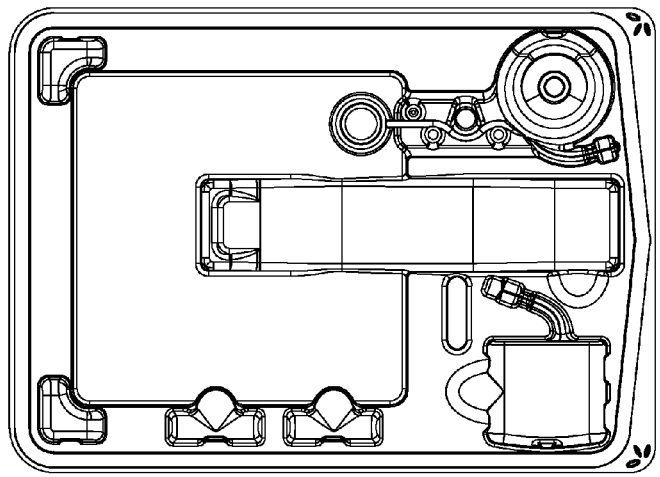
Figure 17L:
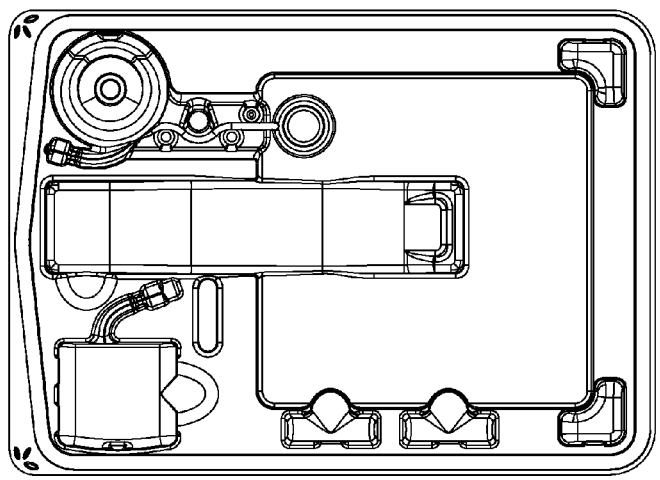
Figure 17M:
Figure 17N:
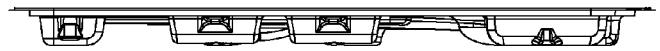
Figure 17O:
Figure 17P:
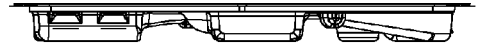
Figure 18A:
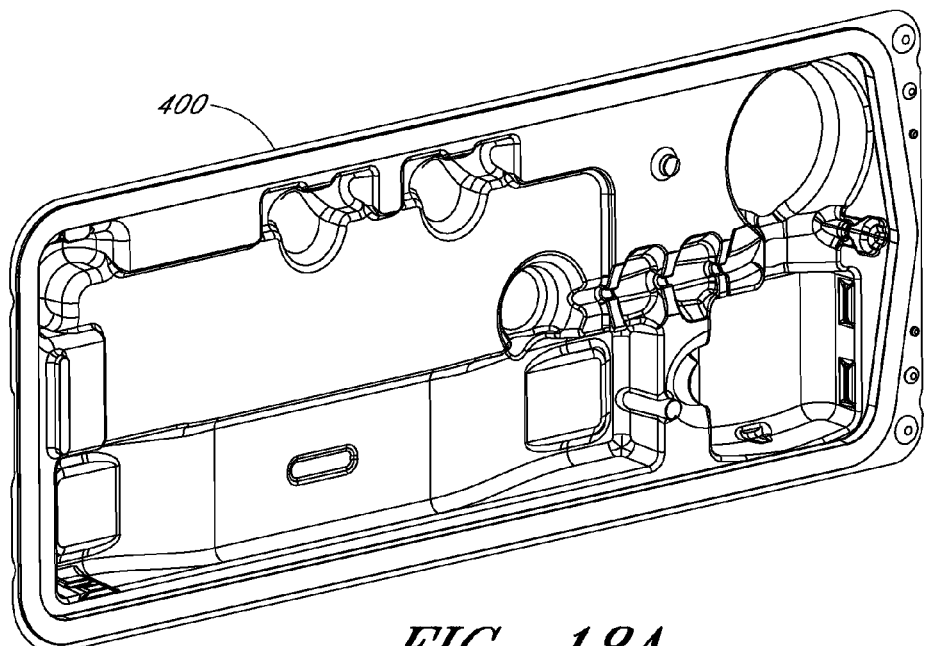
Figure 18B:
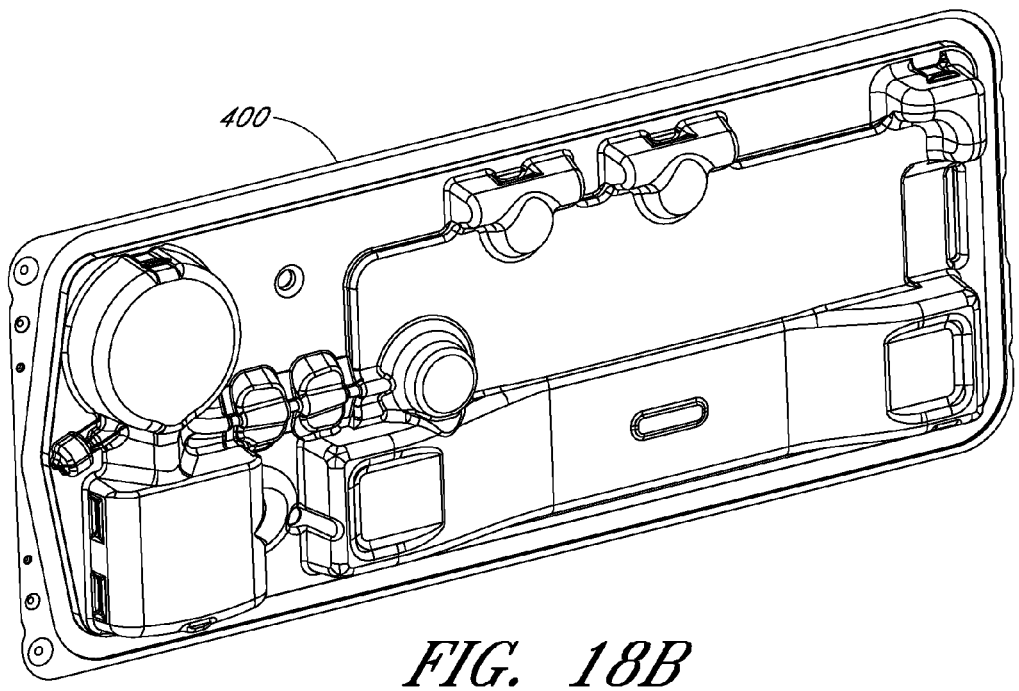
Figure 18C:
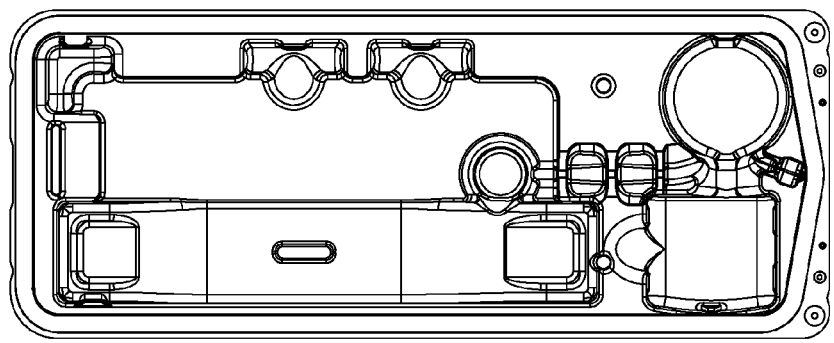
Figure 18D:
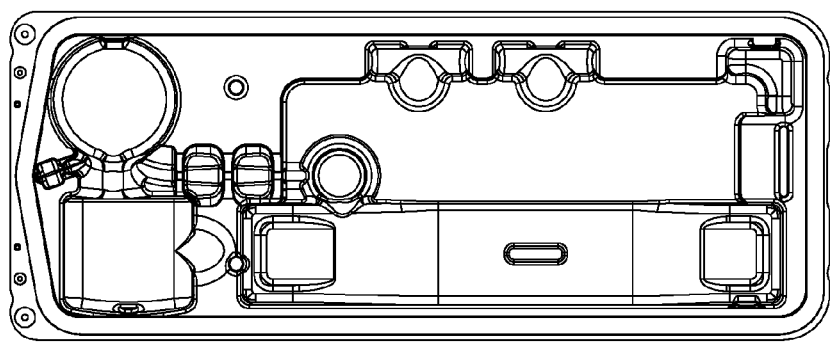
Figure 18E:
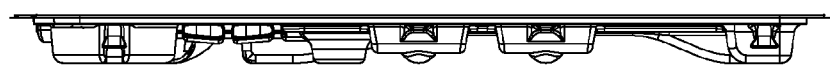
Figure 18F:
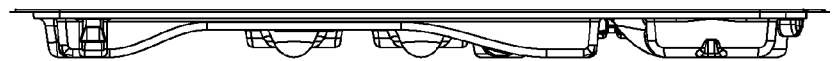
Figure 18G:
Figure 18H:
Figure 18I:
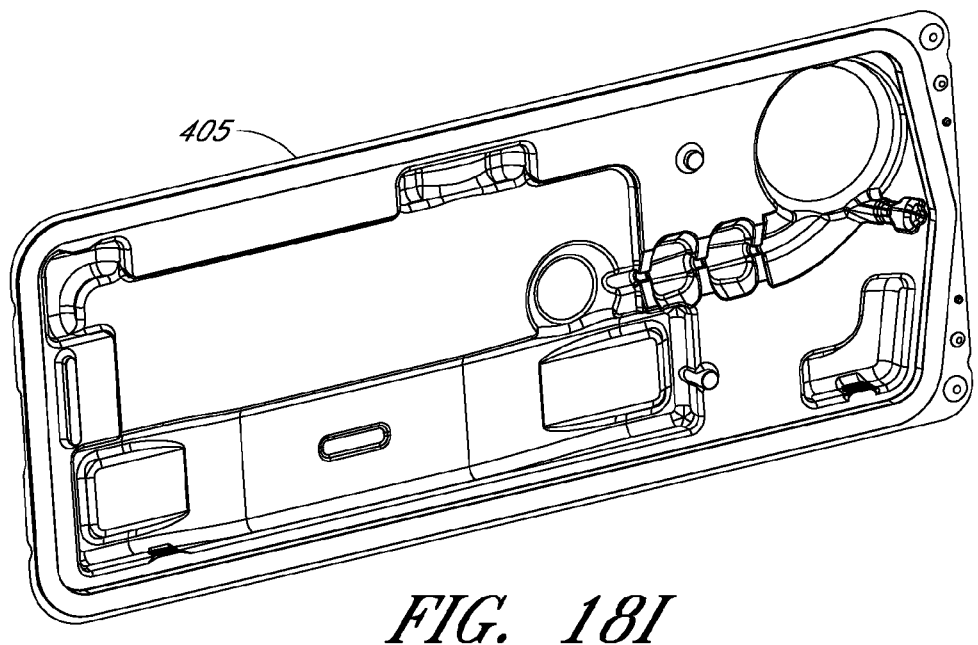
Figure 18J:
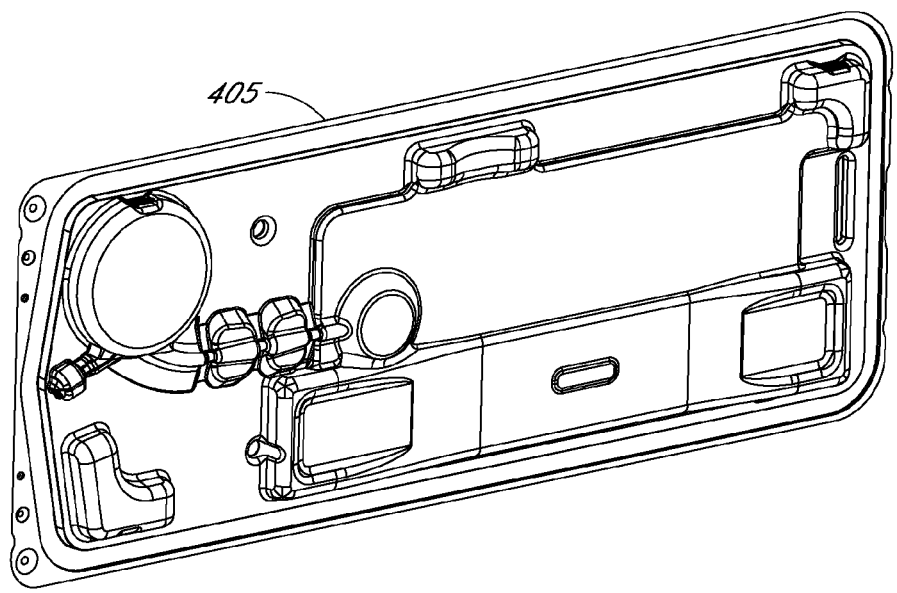
Figure 18K:
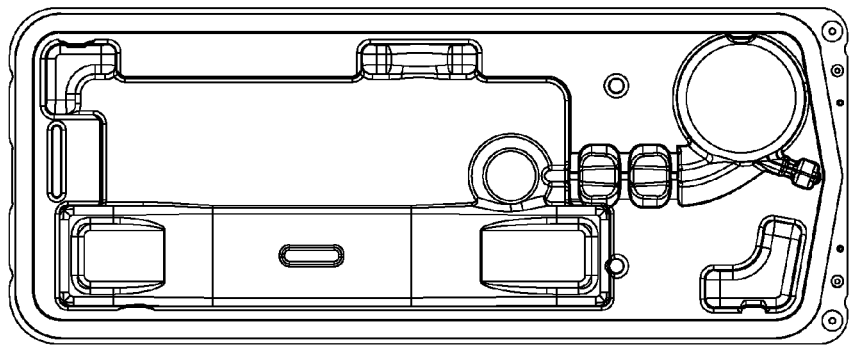
Figure 18L:
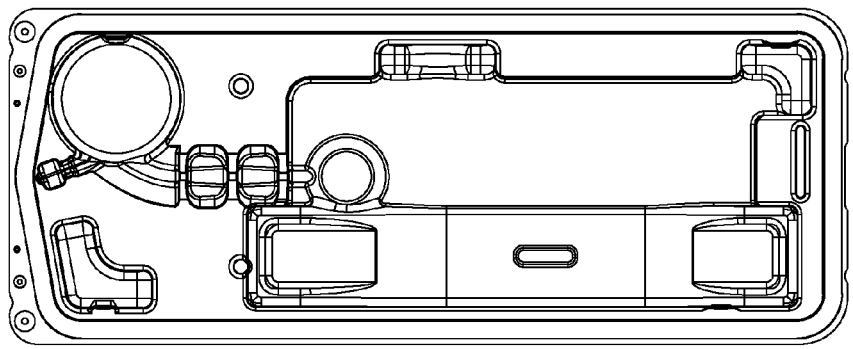
Figure 18M:
Figure 18N:
Figure 18O:
Figure 18P:
Figure 19A:
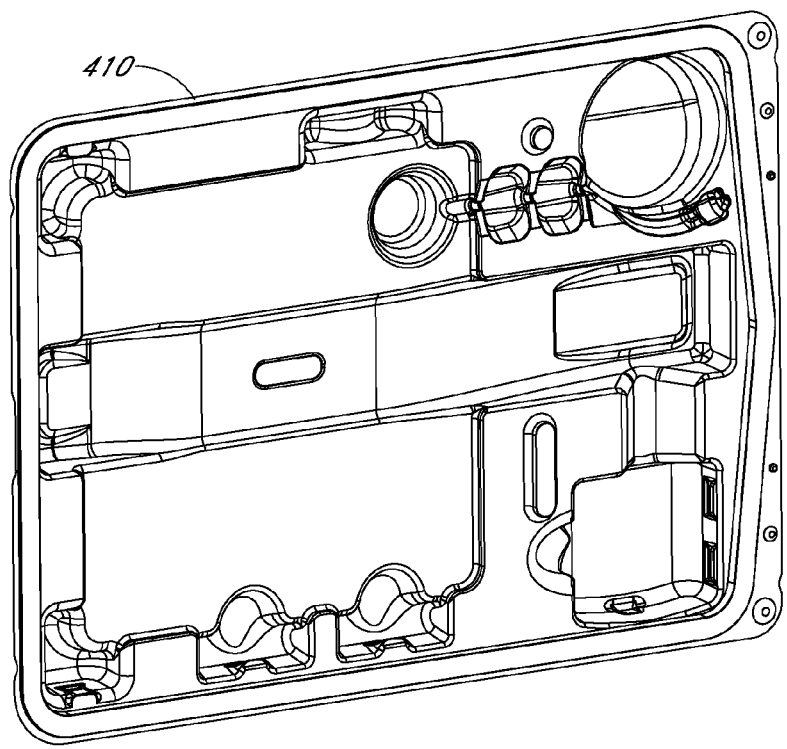
Figure 19B:
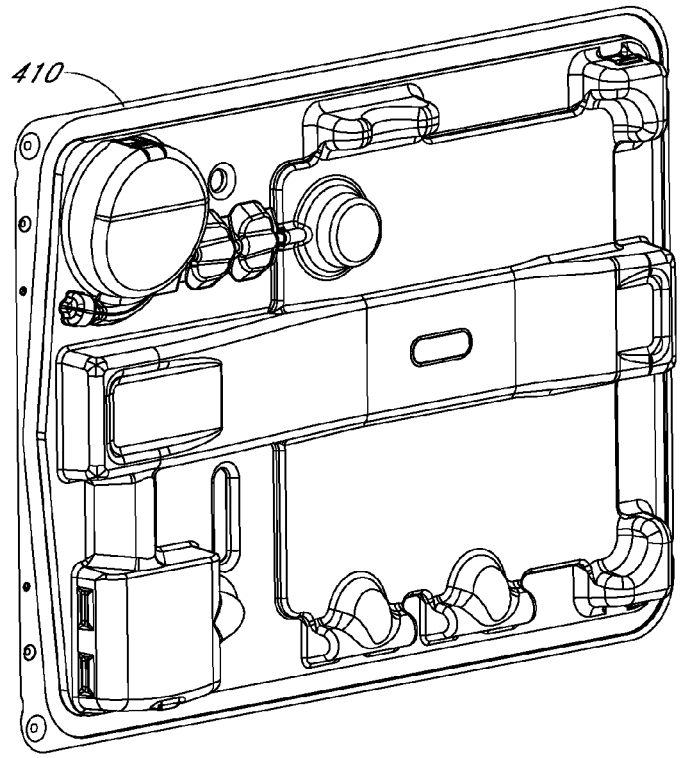
Figure 19C:
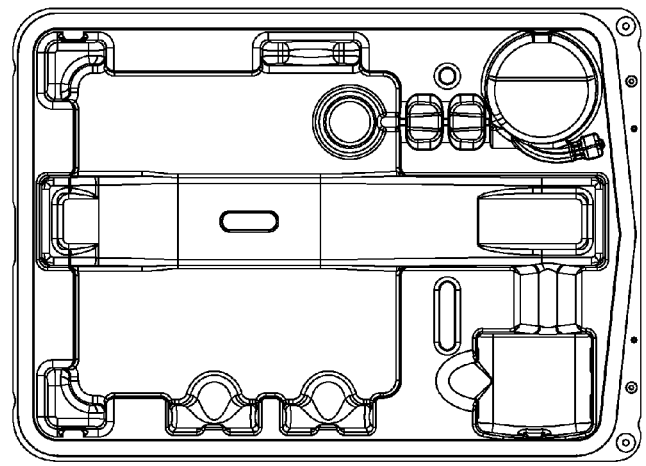
Figure 19D:
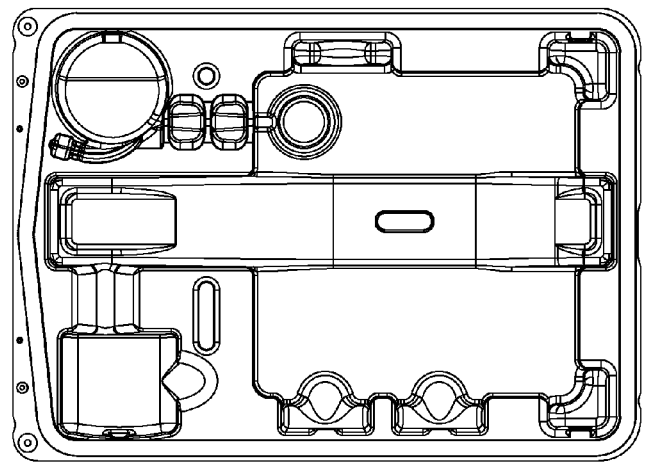
Figure 19E:
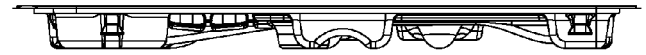
Figure 19F:
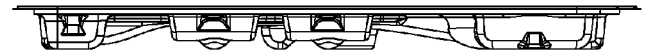
Figure 19G:
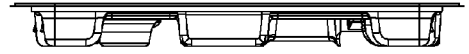
Figure 19H:
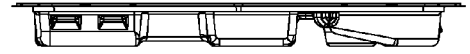
Figure 20A:
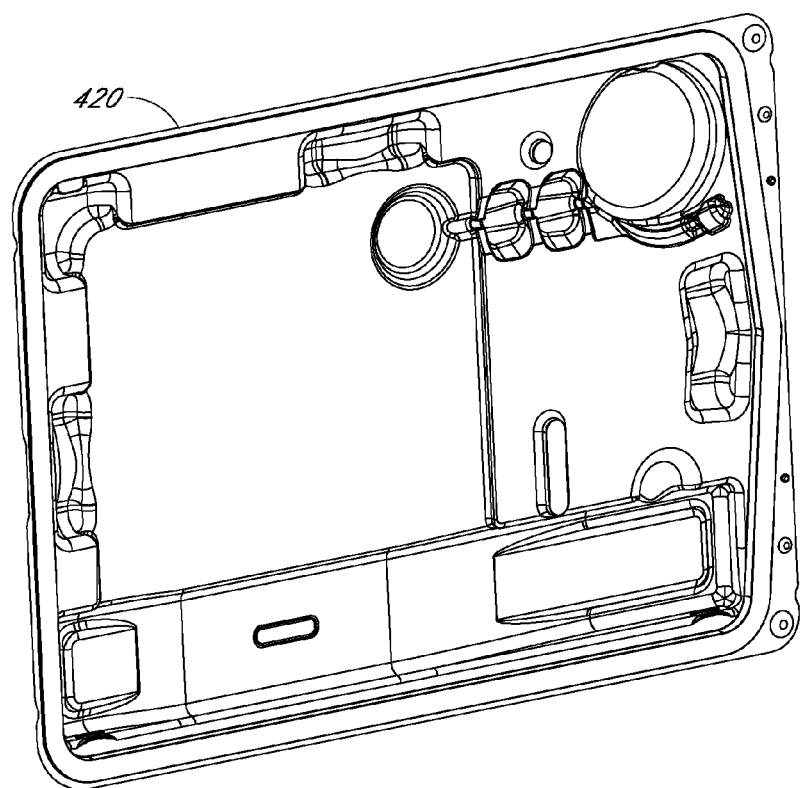
Figure 20B:
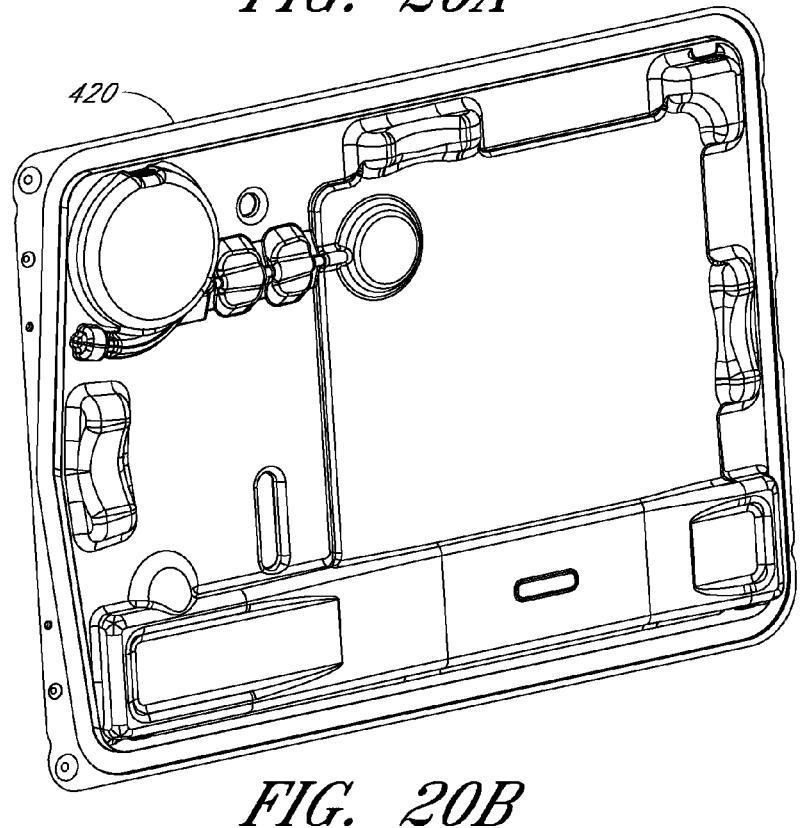
Figure 20C:
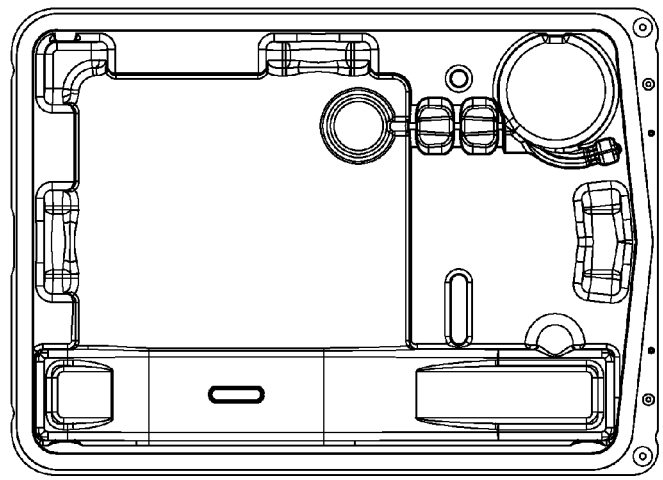
Figure 20D:
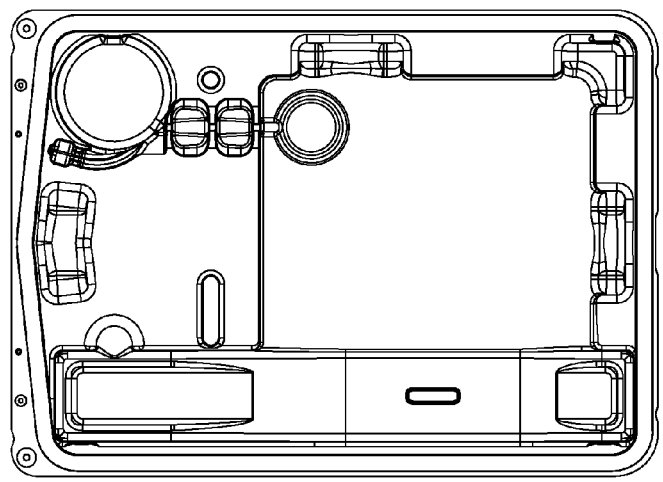
Figure 20E:
Figure 20F:
Figure 20G:
Figure 20H:

Turning to FIG. 7D, as mentioned, fixation strips 148 can be attached around the peripheral edges of the dressing 102 or otherwise. Such fixation strips 148 can be advantageous in some situations so as to provide additional sealing against the skin of the patient surrounding the wound site W. For example, the sealing or fixation strips 148 can provide additional sealing for when a patient is more mobile. In some cases, the fixation strips 148 may be used prior to activation of the pump assembly 104, particularly if the dressing 102 is placed over a difficult to reach or contoured area. In some embodiments, the dressing kit 100 can be provided with up to five sealing strips.

Treatment of the wound site W preferably continues until the wound has reached a desired level of healing. In some embodiments, it may be desirable to replace the dressing 102 after a certain time period has elapsed, or if the dressing is full of wound fluids. During such changes, the pump assembly 104 may be kept, with just the dressing 102 being changed.

FIGS. 8A-20H are top isometric, bottom isometric, top plane, bottom plane, front, back, first side, and second side views, respectively, of embodiments of packaging elements that can be used with any of the embodiments of the wound dressing apparatuses disclosed herein, including a variety of differently sized wound dressing apparatuses. Any of the embodiments of the packaging elements illustrated in FIGS. 8A-20H or otherwise disclosed in this application can have any of the same features, materials, or other details of any of the other packaging elements disclosed herein, including first packaging element 150 discussed above.

The packaging element 300 illustrated in FIGS. 8A-8H is configured to support a dressing that has an approximate 10 cm×20 cm size, and/or one or more of the other components of any TNP therapy kits disclosed herein. The packaging element 310 illustrated in FIGS. 9A-9H is configured to support a dressing that has an approximate 10 cm×20 cm size, and/or one or more of the other components of any TNP therapy kits disclosed herein. The packaging element 320 illustrated in FIGS. 10A-10H is configured to support a dressing that has an approximate 10 cm×30 cm size, and/or one or more of the other components of any TNP therapy kits disclosed herein. The packaging element 330 illustrated in FIGS. 11A-11H is configured to support a dressing that has an approximate 10 cm×30 cm size, and/or one or more of the other components of any TNP therapy kits disclosed herein. The packaging element 300 illustrated in FIGS. 12A-12H is configured to support a dressing that has an approximate 10 cm×40 cm size, and/or one or more of the other components of any TNP therapy kits disclosed herein. The packaging element 350 illustrated in FIGS. 13A-13H is configured to support a dressing that has an approximate 10 cm×40 cm size, and/or one or more of the other components of any TNP therapy kits disclosed herein. The packaging element 360 illustrated in FIGS. 14A-14H is configured to support a dressing that has an approximate 15 cm×15 cm size, and/or one or more of the other components of any TNP therapy kits disclosed herein. The packaging element 365 illustrated in FIGS. 14I-14P is configured to support a dressing that has an approximate 15 cm×15 cm size, and/or one or more of the other components of any TNP therapy kits disclosed herein.

The packaging element 370 illustrated in FIGS. 15A-15H is configured to support a dressing that has an approximate 15 cm×20 cm size, and/or one or more of the other components of any TNP therapy kits disclosed herein. The packaging element 380 illustrated in FIGS. 16A-16H is configured to support a dressing that has an approximate 15 cm×20 cm size, and/or one or more of the other components of any TNP therapy kits disclosed herein. The packaging element 390 illustrated in FIGS. 17A-17H is configured to support a dressing that has an approximate 20 cm×20 cm size, and/or one or more of the other components of any TNP therapy kits disclosed herein. The packaging element 395 illustrated in FIGS. 17I-17P is configured to support a dressing that has an approximate 20 cm×20 cm size, and/or one or more of the other components of any TNP therapy kits disclosed herein. The packaging element 400 illustrated in FIGS. 18A-18H is configured to support a dressing that has an approximate 15 cm×30 cm size, and/or one or more of the other components of any TNP therapy kits disclosed herein. The packaging element 405 illustrated in FIGS. 18I-18P is configured to support a dressing that has an approximate 15 cm×30 cm size, and/or one or more of the other components of any TNP therapy kits disclosed herein. The packaging element 410 illustrated in FIGS. 19A-19H is configured to support a dressing that has an approximate 25 cm×25 cm size, and/or one or more of the other components of any TNP therapy kits disclosed herein. The packaging element 420 illustrated in FIGS. 20A-20H is configured to support a dressing that has an approximate 25 cm×25 cm size, and/or one or more of the other components of any TNP therapy kits disclosed herein.

Figure 21:
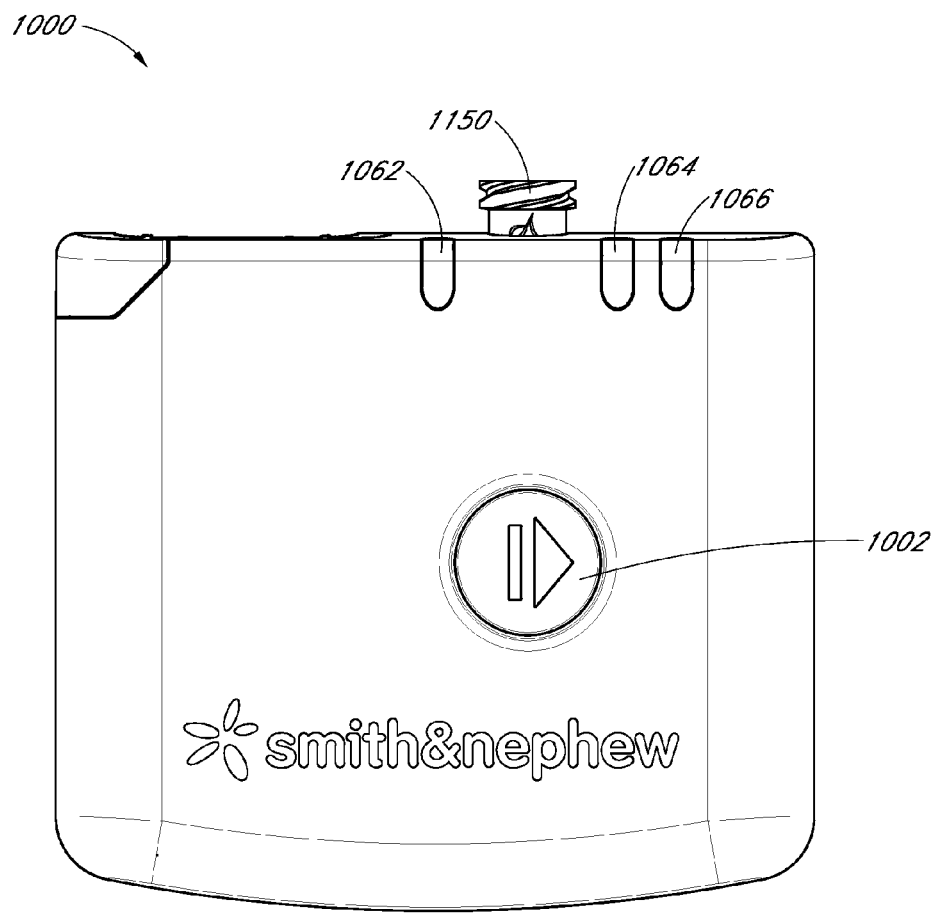
FIG. 21 illustrates a pump assembly according to some embodiments.

FIG. 21 illustrates a pump assembly 1000 according to some embodiments. Any of the embodiments of the pump assembly 1000 disclosed herein can have any of the same or similar components, features, materials, sizes, configurations, and other details of any other pump assembly embodiments disclosed or incorporated by reference herein, including the embodiment of the pump assembly 104 described above. Preferably, the pump assembly 1000 can be miniaturized and portable, although larger conventional portable or non-portable (e.g., wall suction) pumps can also be used. The pump assembly 1000 can include a switch or a button 1002, illustrated as a play/pause button located on the exterior of the housing of the pump assembly. As is explained below, the button 1002 can be configured to stop, pause, and/or restart therapy. Although illustrated as a press button 1002, other types of switches or buttons can be included, such as a touchpad, touch screen, keyboard, and so on.

The pump assembly can further include a connector 1050 (for connecting a conduit, e.g., conduit 106), and three LED indicators 1062, 1064, and 1066. As is illustrated, LED indicator 1062 (e.g., OK indicator) can be configured to indicate normal/abnormal operation of the system. For example, an active (e.g., lit) indicator 1062 can represent normal operation. LED indicator 1064 (e.g., dressing indicator) can be configured to indicate a leak in the system. For example, an active (e.g., lit) indicator 1064 can represent a leak. LED indicator 1066 (e.g., battery indicator) can be configured to indicate the remaining capacity or life of a power source (e.g., batteries). For example, an active (e.g., lit) indicator 1066 can represent a low capacity. In some embodiments, the indicators 1062, 1064, and 1066 can be of a different color, two different colors (e.g., two indicators can share the same color), or same color. Although the pump assembly preferably includes three LED indicators and a push play/pause button, other configurations, locations, and types of indicators, alarms, and switches can alternatively be used. In some embodiments, the pump assembly 1000 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., and/or combinations thereof.

Figure 22:
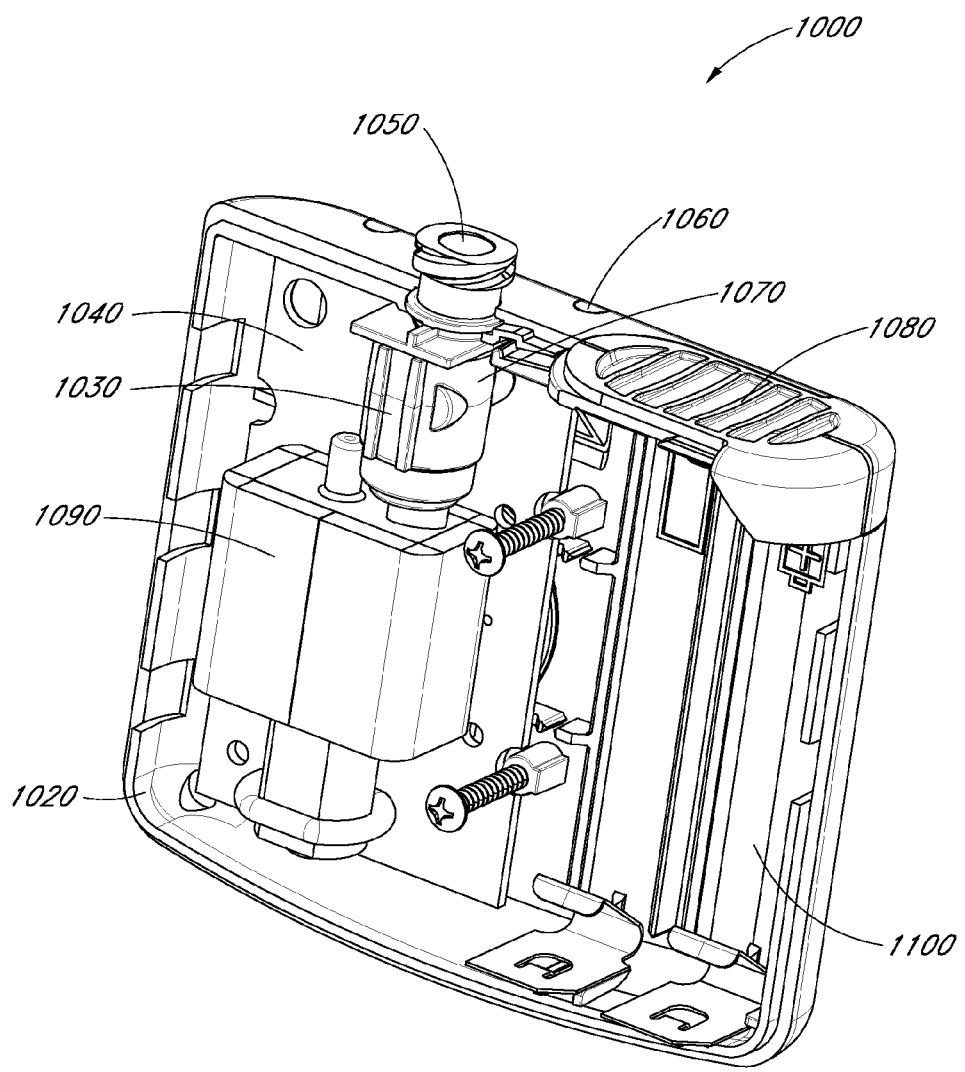
FIG. 22 illustrates a cross-sectional view showing the interior of a pump assembly according to some embodiments.

FIG. 22 illustrates a cross-sectional view showing the interior of the pump assembly 1000 according to some embodiments. As is illustrated, a housing 1020 can enclose the pump assembly. A one-way flow valve 1030 can be configured to maintain a level of negative pressure when the source of negative pressure is not active (e.g., prevent leaks) and prevent fluids and/or exudate aspirated or removed from the wound from entering the pump assembly via the connector 1050. A control board 1040, such as a printed circuit board assembly (PCBA), can be configured to mechanically support and electrically connect various electrical/electronic components, which are described below. The PCBA can be single-sided or double-sided. A negative pressure source 1090, such as pump, can aspirate fluid and/or exudate from a wound. In any of the embodiments disclosed herein, the negative pressure source 1090 can have any of the same components, features, limitations, or other details of any of other negative pressure source embodiment disclosed herein, including without limitation the pump 232 disclosed above. Various pumps can be used for the negative pressure source, including peristaltic pumps, piston pumps, rotary vane pumps, liquid ring pumps, scroll pumps, diaphragm pumps, piezoelectric pumps (e.g., a diaphragm pump operated by a piezoelectric transducer), etc. or combinations thereof. Although the pump assembly preferably includes a miniature, low noise, low power pump, any suitable pump can alternatively be used. The pump assembly 1000 includes indicators 1060 (e.g., LEDs), a pressure sensor 1070 for monitoring pressure in the system, such as pressure under the dressing, and a battery cover 1080 configured to provide access to a battery compartment 1100. Although the pump assembly is preferably powered by two standard, disposable alkaline batteries (e.g., 2 AA batteries), any type of power source, including rechargeable batteries and external power, can alternatively be used.

Figure 23:
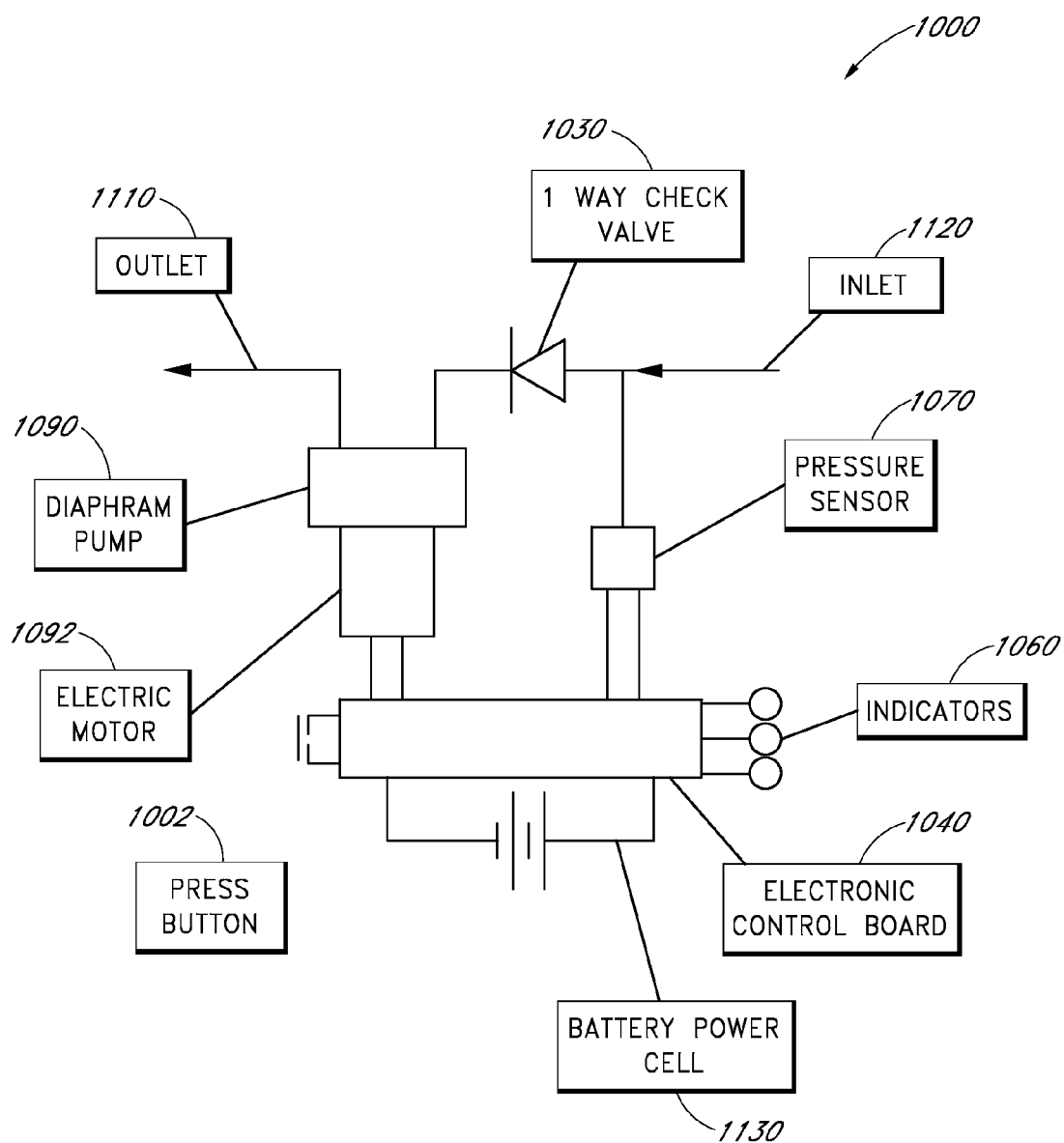
FIG. 23 illustrates a system schematic of a pump assembly according to some embodiments.

FIG. 23 illustrates a system schematic of the pump assembly 1000 according to some embodiments. The pump assembly includes a press button 1002, a control board 1040, and indicators 1060. The pump assembly 1000 can be powered by a battery cell 1130. The pump assembly also includes a pump 1090, such as a diaphragm pump powered by an electric motor 1092, and a pressure sensor 1070. An inlet 1120 can be configured to connect the pump assembly 1000 to a dressing, for example, via a conduit. The inlet 1120 can be connected to a one-way valve 1030, which can be configured to help maintain a level of negative pressure when the source of negative pressure is not active, avoid leaks, and prevent fluids and/or exudate aspirated or removed from the wound from entering the pump assembly 1000. The pump 1090 can also be connected to an outlet 1110. In some embodiments, the outlet 1110 can be configured to vent air to the atmosphere. In some embodiments, a filter (not shown) can be interposed between the outlet and the atmosphere. The filter can be a bacterial filter, odor filter, etc. or any combination thereof.

Figure 24:
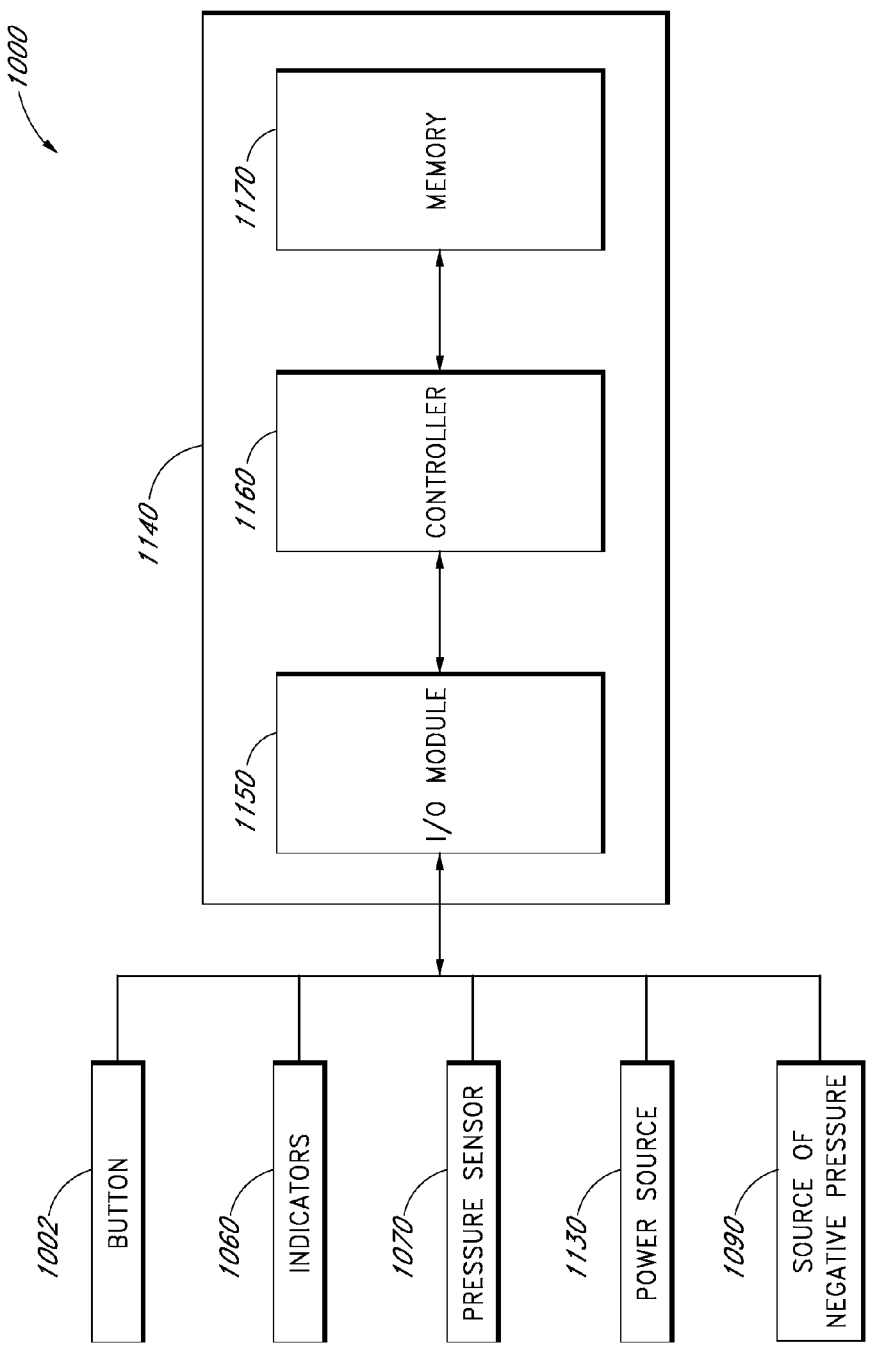
FIG. 24 illustrates an electrical component schematic of a pump assembly according to some embodiments.

FIG. 24 illustrates an electrical component schematic of the pump assembly 1000 according to some embodiments. Module 1140, which can be a control board (e.g., PCBA), can include an input/output (I/O) module 1150, controller 1160, and memory 1170. In some embodiments, module 1140 can include additional electric/electronic components, for example, fuse or fuses. The controller 1160 can be a microcontroller, processor, microprocessor, etc. or any combination thereof. For example, the controller 1160 can be of STM8L MCU family type from ST Microelectronics, such as STM8L 151G4U6, or of MC9S08QE4/8 series type from Freescale, such as MC9S08QE4CWJ. Preferably, the controller 1160 is a low power or ultra low power device, but other types of devices can alternatively be used. Memory 1170 can include one or more of volatile and/or nonvolatile memory modules, such as one or more of read-only memory (ROM), write once read many memory (WORM), random access memory (e.g., SRAM, DRAM. SDRAM, DDR, etc.), solid-state memory, flash memory, magnetic storage, etc. or any combination thereof. Memory 1170 can be configured to store program code or instructions (executed by the controller), system parameters, operational data, user data, etc. or any combination thereof.

The I/O module 1150 can be configured to function as an interface between the controller 1160 and other system components that provide and/or are responsive to electromagnetic signals. In other words, the I/O module 1150 can be configured to allow the controller 1160 to monitor the operation of the system and to control other components of the system. In some embodiments, as is illustrated, the I/O module 1150 can be in electromagnetic communication with a button 1002, indicators 1060, pressure sensor 1070, power source 1130, and source of negative pressure 1090. The I/O module can comprise an interface or multiple interfaces configured to communicate with various components. The interface can include standard and/or non-standard ports, such as serial ports, parallel ports, bus interfaces, etc. or any combination thereof.

Figure 25:
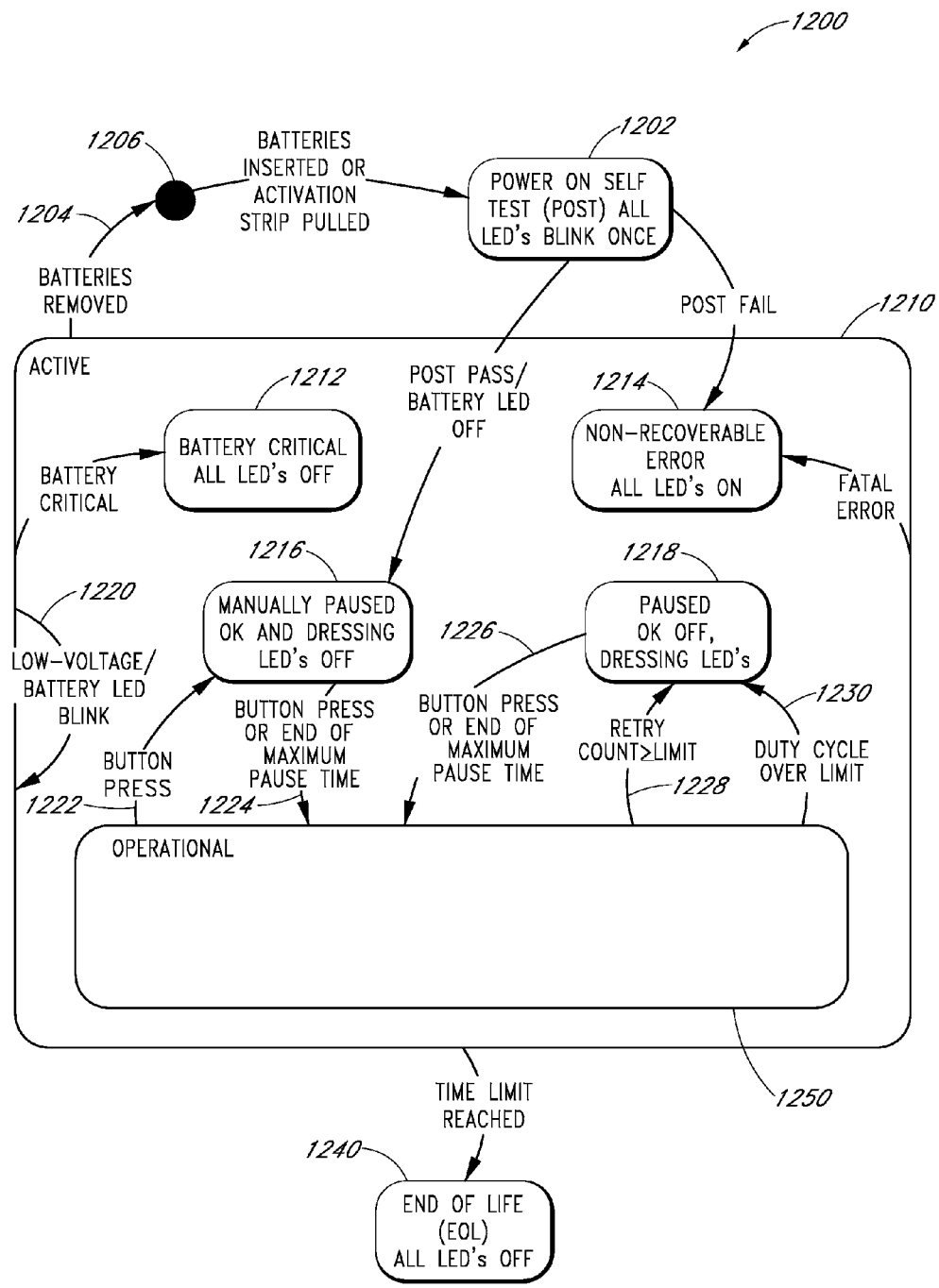
FIG. 25 illustrates a top level state diagram of operation of a pump assembly according to some embodiments.
Figure 26:
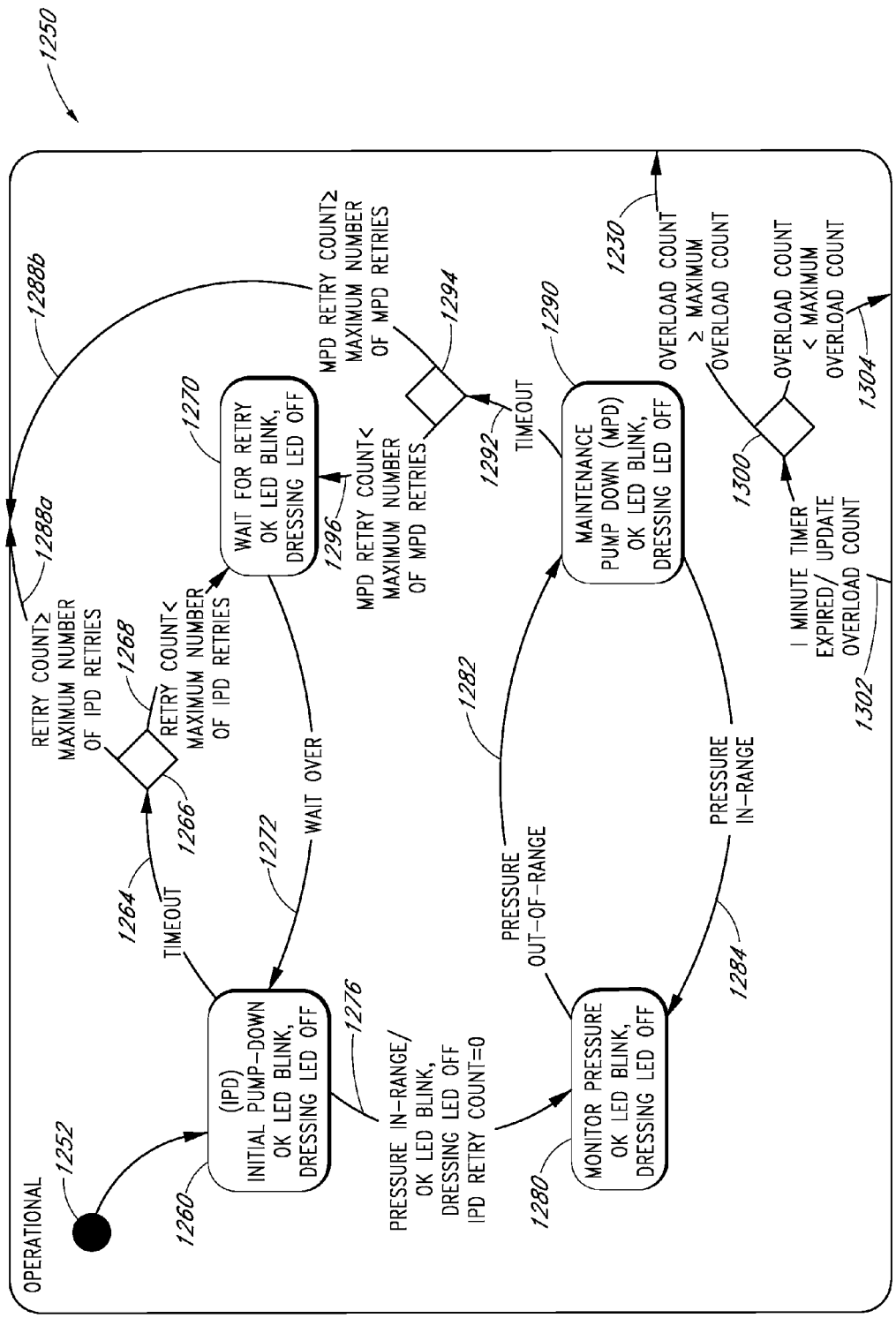
FIG. 26 illustrates an operational state diagram of operation of a pump assembly according to some embodiments.

In some embodiments, the pump assembly 1000 can be configured to control the operation of system. For example, the pump assembly 1000 can be configured to provide a suitable balance between uninterrupted delivery of therapy and/or avoidance of inconveniencing the user by, for example, frequently or needlessly pausing or suspending therapy and a desire to conserve power, limit noise and vibration generated by the negative pressure source, etc. FIG. 25 illustrates a top level state diagram 1200 of operation of the pump assembly according to some embodiments. In some embodiments, the controller 1140 can be configured to implement the flow of the state diagram 1200. As is illustrated in FIG. 25, the operation of the pump assembly can, in some embodiments, be grouped into four general state categories: inactive/initialization (states 1206 and 1202), active 1210, operational 1250, and end of life (state 1214). As is illustrated in FIGS. 25 and 26, state categories 1210 and 1250 each comprises multiple states and transitions between states.

In some embodiments, so long as the power source is not connected, removed (as is illustrated by the transition 1204), or the pump assembly has not been activated (e.g., by pulling an activation strip, triggering the switch, or the like), the pump assembly remains in state 1206. While remaining in this state, the pump assembly can remain inactive. When the power source is connected and/or the pump assembly has been activated for a first time, the pump assembly transitions to state 1202, where power on self test(s) (POST) can be performed. Power on self test(s) can include performing various checks to ensure proper functionality of the system, such as testing the memory 1170 (e.g., performing a check, such as a cyclic redundancy check, of the program code to determine its integrity, testing the random access memory, etc.), reading the pressure sensor 1070 to determine whether the pressure values are within suitable limits, reading the remaining capacity or life of the power source (e.g., battery voltage, current, etc.) to determine whether it is within suitable limits, testing the negative pressure source, and the like. As is illustrated, indicators 1060 (e.g., LEDs) can be configured to indicate to the user (e.g., by blinking or flashing once) that the pump assembly is undergoing POST test(s).

In some embodiments, if one or more of POST test(s) fail, the pump assembly can transition to non-recoverable error state 1214. While in this state, the pump assembly can deactivate therapy, and the indicators 1060 can be configured and indicate to the user that an error was encountered. In some embodiments, all indicators can be configured to remain active. Based on the severity of error, in some embodiments, the pump assembly can be configured to recover from the error and continue operation (or transition to the non-recoverable error state 1214). As is illustrated, the pump assembly can transition to state 1214 upon encountering a fatal error during operation. Fatal errors can include program memory errors, program code errors (e.g., encountering an invalid variable value), controller operation errors (e.g., watchdog timer expires without being reset by the controller 1160), component failure (e.g., inoperative negative pressure source, inoperative pressure sensor 1070, etc.), and any combination thereof.

When POST test(s) pass, in some embodiments, the pump assembly can transition to a manually paused state 1216. As is illustrated, this transition can be indicated to the user by deactivating one of indicators 1060 (e.g., battery indicator 1066). When the pump assembly transitions into and remains in the manually paused state 1216, the user can be provided an indication, such as by deactivating indicators 1062 (OK indicator) and 1064 (dressing indicator). In some embodiments, therapy can be suspended while the pump assembly remains in the manually paused state 1216. For example, the source of negative pressure (e.g., pump 1090) can be deactivated (or turned off). In some embodiments, indication can be provided by deactivating the source of negative pressure.

In some embodiments, the pump assembly can be configured to make a transition 1224 from the manually paused state 1216 to the operational state category 1250 (where the pump assembly is configured to deliver therapy) in response to receiving a signal from the switch. For example, the user can press a button to start, suspend, and/or restart therapy. In some embodiments, the pump assembly can be configured to monitor the duration of time the pump assembly remains in the manually paused state 1216. This can be accomplished, for example, by maintaining a timer (in firmware, software, hardware or any combination thereof), which can be reset and started when the pump assembly transitions into the manually paused state 1216. The pump assembly can be configured to automatically make the transition 1224 from the manually paused state 1216 to the operational state category 1250 when the time duration exceeds a threshold. In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump assembly nears the end of life (as is explained below), the threshold can be decreased. In some embodiments, the user can pause therapy by activating the switch (e.g., pressing the button), thereby causing the pump assembly to make a transition 1222 from the operational state category 1250 to the manually paused state 1216. In some embodiments, the pump assembly can be configured so that the user can only pause therapy, whereas disconnecting the power source (e.g., removing batteries) stops therapy.

In some embodiments, the pump assembly can be configured to include a paused state 1218. When the pump assembly transitions into and remains in the paused state 1218, the user can be provided an indication. For example, the pump assembly can be configured to deactivate the OK indicator 1062 and cause the dressing indicator 1064 to flash or blink. In some embodiments, therapy can be suspended while the pump assembly remains in the manually paused state 1216. For example, the source of negative pressure (e.g., pump 1090) can be deactivated (or turned off), which provides the indication to the user that the pump assembly is in the paused state 1218. As is explained below, in some embodiments, the pump assembly can be configured to transition from the operational state category 1250 into the paused state 1218 when a number of retry cycles exceeds a retry limit (transition 1228) or when duty cycle is determined to exceed a duty cycle limit (transition 1230). In some embodiments, transitions 1228 and 1230 can reflect the presence of a leak in the system.

In some embodiments, the pump assembly can be configured to make a transition 1226 from the paused state 1218 to the operational state category 1250 (where the pump assembly is configured to activate the pump to deliver therapy) in response to receiving a signal from the switch (e.g., the user pressing a button to restart therapy). In some embodiments, the pump assembly can be configured to monitor the duration of time the pump assembly remains in the paused state 1218. For example, this can be accomplished by maintaining a timer (in firmware, software, hardware or any combination thereof), which can be reset and started when the pump assembly transitions into the paused state 1218. The pump assembly can be configured to automatically make the transition 1226 from the paused state 1218 to the operational state category 1250 when the time duration exceeds a threshold. The threshold can be the same or different than the threshold of the manually paused state 1216 described above. In some embodiments, the threshold can be a preset value, such as between 1 minute or less and 1 hour or more. In some embodiments, the threshold can be set or changed by the user. In some embodiments, the threshold can be varied based on various operating conditions or on any combination thereof. For example, as the pump assembly nears the end of life (as is explained below), the threshold can be decreased.

In some embodiments, the pump assembly includes both the manually paused state 1216 and the paused state 1218 in order to differentiate between various causes for pausing therapy. Such ability to differentiate can allow the pump assembly to provide the user with an indication of a particular cause for pausing therapy (e.g., manually paused state 1216 and paused state 1218 can provide different indications). For example, therapy can be paused due to the user manually pressing the button, in which case the pump assembly can make the transition 1222 from the operational state category 1250 to the manually paused state 1216. As another example, therapy can be paused due to detecting a leak, in which case the pump assembly can make the transition 1228 and/or 1230 from the operational state category 1250 to the paused state 1218. In some embodiments, the pump assembly can be configured to include one state indicating a suspension or pause in the delivery of therapy or more than two such states.

In some embodiments, the pump assembly can be configured to monitor the remaining capacity or life of the power source (e.g., by periodically reading or sampling the battery voltage, current, etc.). The pump assembly can be configured to indicate to the user the remaining capacity. For example, if the power source is determined to have a normal remaining capacity (e.g., as a result of comparison to a threshold, such as 2.7V, 2.6V, 2.5V, etc.), the battery indicator 1066 can be deactivated. If the power source is determined to have low remaining capacity, the pump assembly can be configured to provide an indication to the user by, for example, causing the battery indicator 1066 to blink or flash, as is illustrated by the transition 1220. In some embodiments, the battery indicator 1066 can be configured to be blinking or flashing intermittently or continuously regardless of the state the pump assembly is in or only in particular states.

In some embodiments, when the remaining capacity of the power source is determined to be at or near a critical level (e.g., as a result of comparison to a threshold, such as 2.4V, 2.3V, 2.2V, etc.), the pump assembly can be configured to transition into a battery critical state 1212. In some embodiments, the pump assembly can be configured to remain in this state until the capacity of the power source is increased, such as by replacing or recharging the power source. The pump assembly can be configured to deactivate therapy while remaining in the battery critical state 1212. In addition, as is illustrated, the pump assembly can be configured to indicate to the user that the power source is at or near the critical level by, for example, deactivating all indicators.

In some embodiments, the pump assembly can be configured to provide therapy for a predetermined period of time, such as approximately 1 day, 2-10 days, etc. following a first activation. In some embodiments, such period of time can be a preset value, changed by the user, and/or varied based on various operating conditions or on any combination thereof. The pump assembly can be disposed upon the expiration of such period of time. In some embodiments, the first activation can be reflected by a transition into the active state category 1210, by pulling the activation strip (e.g., transition into state 1202), etc. Once the pump assembly has been activated, the pump assembly can be configured to monitor the duration it has remained active. In some embodiments, the pump assembly can be configured to monitor the cumulative duration of remaining in the active state category 1210. This can be accomplished, for example, by maintaining a timer (in firmware, software, hardware or any combination thereof), that reflects such duration.

When the duration reaches or exceeds a threshold (e.g., 7 days), the pump assembly can be configured to transition to an end of life (EOL) state 1240. The pump assembly can be configured to deactivate therapy while remaining in state 1240 and to indicate to the user that end of pump assembly' usable life has been reached. For example, the pump assembly can be configured to deactivate all indicators and/or deactivate the button. In some embodiments, when the pump assembly is disposable, transitioning to the end of life state 1240 means that the pump assembly can be disposed of. The pump assembly can be configured to disable reactivation of the pump assembly once the end of life has been reached. For example, the pump assembly can be configured to not allow reactivation even if the power source is disconnected and reconnected later, which can be accomplished by storing an indication, value, flag, etc. in the read only memory.

FIG. 26 illustrates the operational flow in state category 1250 of the pump assembly 1000 according to some embodiments. The pump assembly can be configured to deliver therapy, monitor leaks in the system, provide indication(s) to the user, and the like. As is explained below, in some embodiments, the pump assembly can be configured to deliver therapy by initially attempting to establish a first desired negative pressure level (e.g., negative pressure between −5 mmHg or less and −200 mmHg or more, such as −100 mmHg) under the dressing 1010. In some embodiments, the first desired negative pressure level can be a preset value, set or changed by the user, and/or varied based on various operating conditions or on any combination thereof. Once the first desired negative pressure level is established under the dressing 1010, the pump assembly can be configured to deactivate the source of negative pressure (e.g., pump). When negative pressure under the dressing 1010 decreases (i.e., gravitates toward standard atmospheric pressure) due to leaks in the system, the pump assembly can be configured to restore negative pressure under the dressing by activating the pump to establish a second desired negative pressure level under the dressing (e.g., negative pressure between −5 mmHg or less and −200 mmHg or more, such as −100 mmHg). In some embodiments, the second desired negative pressure level can be a preset value, set or changed by the user, and/or varied based on various operating conditions or on any combination thereof. In some embodiments, the first and second desired negative pressure levels can be the same. In some embodiments, the first and second desired negative pressure levels can be different, that is, the second negative pressure level can be less than the first negative pressure level or vice versa.

In some embodiments, the pump assembly can transition from the manually paused state 1216 and/or paused state 1218 to state 1252. As is explained above, this transition can be caused by the user pressing the button to start/restart therapy and/or upon expiration of duration of time, such as 1 hour. The pump assembly can be configured to immediately transition to an initial pump down (IPD) state 1260, where the pump can be activated to establish the first desired negative pressure level under the dressing 1010. In some embodiments, the pump can be activated if the pressure level under the dressing is above (less than) the first desired negative pressure level. Activating the source of negative pressure to establish the first desired negative pressure level under the dressing 1010 can be referred to herein as the "initial pump down." The pump assembly can be configured to indicate to the user that it is performing the initial pump down by, for example, causing the OK indicator 1062 to blink or flash and deactivating the dressing indicator 1064. In some embodiments, the indication can be provided by, for example, activating the source of negative pressure. The pump assembly can be configured to measure the level of pressure under the dressing 1010 by reading or sampling the sensor 1070.

In some embodiments, the pump assembly can be configured to monitor the duration of time the pump assembly remains in the IPD state 1260. This can be accomplished, for example, by maintaining a timer (in firmware, software, hardware or any combination thereof), which can be reset and started when the pump assembly transitions into the IPD state 1260. In some embodiments, in order to conserve power, limit the noise and/or vibration generated by the pump, etc., the pump assembly can be configured to suspend the initial pump down operation for a period of time and, later, retry the initial pump down. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, when the duration of time for remaining in the IPD state 1260 equals or exceeds a threshold (e.g., 30 seconds), the pump assembly can be configured to make the transition 1264 to state 1266. In some embodiments, the threshold can be a preset value, such as between 5 seconds or lower and 5 minutes or higher. In some embodiments, the threshold can be set or changed by the user. In some embodiments, the threshold can be varied based on various operating conditions or on any combination thereof. In some embodiments, the pump assembly can be configured to deactivate the pump when making the transition 1264. The pump assembly can be configured to monitor a number attempts (e.g., by maintaining a counter which can be reset in state 1252 and updated in wait state 1270) made to establish the first desired negative pressure under the dressing 1010. In some embodiments, the pump assembly can be configured to provide a limited or maximum number of IPD retry attempts in order, for example, to conserve power. Preferably, the pump assembly can be configured to provide a limited number of consecutive IPD retry attempts, although the pump assembly can be configured to provide a limited number of non-consecutive IPD retry attempts or a mix of consecutive and non-consecutive IPD retry attempts. The threshold for IPD retry attempts can be 1, 2, 3, 4, 5, and so on. In some embodiments, the threshold can be a preset value. In some embodiments, the threshold can be set or changed by the user. In some embodiments, the threshold can be varied based on various operating conditions or on any combination thereof.

In some embodiments, the pump assembly can be configured to determine in state 1266 whether the number of IPD retry attempts made is equal to or exceeds the threshold (e.g., 1 retry attempt). In case the number of IPD retry attempts made is equal or exceeds the threshold, the pump assembly can be configured to make the transition 1228a to the paused state 1218, where therapy is paused or suspended as is described above. Otherwise, the pump assembly can be configured to make the transition 1268 to the wait state 1270. In some embodiments, the pump assembly can be configured to deactivate the source of negative pressure in state 1266, which can provide an indication to the user that the pump assembly transitioned to state 1266.

In some embodiments, the pump assembly can be configured to deactivate the pump in the wait state 1270, thereby pausing therapy for a period of time (e.g., between 1 second or less and 1 minute or more, such as 15 seconds). This can be accomplished, for example, by maintaining a timer (in firmware, software, hardware or any combination thereof), which can be reset and started when the pump assembly transitions into the wait state 1270. This period of time in the wait state 1270 can be preset or variable (e.g., automatically or by the user). In some embodiments, the period of time can be varied based on various operating conditions or on any combination thereof. The period of time the pump assembly remains in the wait state 1270 can be decreased or increased (e.g., multiplied by a factor between 0.1 or less and 4.0 or more, such as 2), on each transition into the wait state 1270. The period of time can be decreased or increased on each successive transition into the wait state 1270. The period of time can be decreased or increased until it equals or passes a threshold (e.g., between 1 second or less and 5 minutes or more, such as 4 minutes). In addition, the period of time can be reset to an initial value upon transition to a monitor pressure state 1280, transition to the manually paused state 1216, transition to the paused state 1218, etc.

In some embodiments, the pump assembly can be configured to indicate to the user that the pump assembly is in the wait state 1270. For example, the pump assembly can be configured to cause the OK indicator 1062 to flash or blink and deactivate the dressing indicator 1064. In some embodiments, deactivating the pump can provide indication that the pump assembly is in the wait state 1270. Upon expiration of the period of time in the wait state, the pump assembly can be configured to make the transition 1272 from the wait state 1270 to the IPD state 1260, where the pump assembly can attempt to establish the first desired negative pressure level under the dressing 1010. In some embodiments, the pump assembly can be configured to ensure that the negative pressure level under the dressing remains above a certain safety level. For example, the pump assembly can be configured to maintain the negative pressure level under the dressing 1010 above a safety level between −150 mmHg or less and −250 mmHg or more, such as −225 mmHg.

In some embodiments, when the first desired negative pressure level under the dressing 1010 has been established, the pump assembly can be configured to make the transition 1276 to a monitor state 1280. The pump assembly can be configured to reset the number of IPD retry attempts when making the transition 1276. The pump assembly can be configured to indicate the transition to the monitor state 1280 to the user by, for example, causing the OK indicator 1062 to blink or flash and deactivating the dressing indicator 1064. While remaining in the monitor state 1280, the pump assembly can be configured to deactivate the pump (which can provide an indication to the user that the pump assembly is in the monitor state 1280) and periodically or continuously monitor the level of pressure under the dressing 1010. The pump assembly can be configured to measure the level of pressure under the dressing 1010 by reading or sampling the sensor 1070.

In some embodiments, the pump assembly can be configured to determine whether, for example, due to leaks in the system, the level of negative pressure under the dressing 1010 decreases to reach and/or pass (e.g., become less than) a threshold. The threshold can be selected from the range between −10 mmHg or less and −100 mmHg or more, such as −60 mmHg. In some embodiments, the threshold can be a preset value, set or changed by the user, and/or varied based on various operating conditions or on any combination thereof. If the threshold is determined to be reached or passed, the pump assembly can be configured to restore the level of negative pressure under the dressing 1010. In some embodiments, the pump assembly can be configured to reestablish the first desired negative pressure level or establish another, different negative pressure level. This can be accomplished by making the transition 1282 to a maintenance pump down (MPD) state 1290.

In some embodiments, the pump assembly can be configured to activate the pump to establish the desired level of negative pressure under the dressing 1010 (e.g., the first desired level) while the pump assembly remains in the MPD state 1290. The pump assembly can be configured to provide an indication to the user, for example, by causing the OK indicator 1062 to blink or flash and deactivating the dressing indicator 1064. In some embodiments, the pump assembly activating the source of negative pressure can provide an indication to the user that the pump assembly transitioned to state 1290. In some embodiments, the pump assembly can be configured to generate less noise and vibration when the pump is activated in the MPD state 1290 than when the pump is activated in the IPD state 1264. For example, the difference in the noise level can be between 1 dB or less and 30 dB or more, such as approximately 7 dB, approximately 20 dB, etc. As another example, the difference in the noise level can be between 30 dB or less to 80 dB or more, such as approximately 45 dB, approximately 50 dB, approximately 65 dB, etc.

In some embodiments, the pump assembly can be configured to monitor the duration of time it remains in the MPD state 1290. This can be accomplished, for example, by maintaining a timer (in firmware, software, hardware or any combination thereof), which can be reset and started when the pump assembly makes the transition 1282 into the MPD state 1290. In some embodiments, in order to conserve power, limit the noise and/or vibration generated by the pump, etc., the pump assembly can be configured to suspend the maintenance pump down operation for a period of time and, later, retry the initial pump down and/or maintenance pump down. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, when the duration of time in the MPD state 1290 equals or exceeds a threshold (e.g., a value between 5 seconds or lower and 5 minutes or higher, such as 10 seconds) and the pressure level under the dressing 1010 has not reached the desired negative pressure level, the pump assembly can be configured to make the transition 1292 to state 1294. The threshold can be a preset value, set or changed by the user, and/or varied based on various operating conditions or on any combination thereof. In some embodiments, the pump assembly can be configured to deactivate the pump when making the transition 1292, which can provide an indication to the user that the pump assembly is making the transition. The pump assembly can be configured to monitor a number of MPD attempts (e.g., by maintaining a counter which can be reset in the state 1252 and/or when making the transition 1228b and updated when making the transition 1296) made to establish the desired negative pressure under the dressing 1010. In some embodiments, the pump assembly can be configured to provide a limited or maximum number of MPD retry attempts (e.g., to conserve power). Preferably, the pump assembly can be configured to provide a limited number of consecutive MPD retry attempts, although the pump assembly can be configured to provide a limited number of non-consecutive MPD retry attempts or a mix of consecutive and non-consecutive retry attempts. The threshold for MPD retry attempts can be 1, 2, 3, 4, 5, and so on. In some embodiments, the threshold can be a preset value, set or changed by the user, and/or varied based on various operating conditions or on any combination thereof. The pump assembly can be configured to set the number of IPD and MPD retry attempts to the same or different value. The pump assembly can be configured to determine in state 1294 whether the number of MPD retry attempts made is equal to or exceeds the threshold (e.g., 3 retry attempts). In case the number of MPD retry attempts made is equal or exceeds the threshold, the pump assembly can be configured to make the transition 1228b to the paused state 1218, where therapy is paused or suspended as is described above. Otherwise, the pump assembly can be configured to make the transition 1296 to the wait state 1270, where therapy is paused or suspended as is described above. Alternatively, the pump assembly can be configured to make the transition to the IPD state 1260 or MPD state 1290.

In some embodiments, the pump assembly can be configured to make the transition 1284 to the monitor state 1280 if the level of pressure under the dressing reaches or exceeds (e.g., become greater than) the desired negative pressure level. The pump assembly can also be configured to reset the number of MPD retry attempts when making the transition 1284.

In some embodiments, the pump assembly can be configured to monitor the duty cycle of the source of negative pressure (e.g., pump). The pump assembly can be configured to monitor the duty cycle periodically and/or continuously. Duty cycle measurements can reflect various operating conditions of the system, such as presence and/or severity of leaks, rate of flow of fluid (e.g., air, liquid and/or solid exudate, etc.) aspirated from wound, and so on. For example, duty cycle measurements can indicate presence of a high leak, and the pump assembly can be configured to indicate this condition and/or temporarily suspend or pause operation of the pump in order to conserve power. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, the pump assembly can be configured to periodically monitor the duty cycle, such as once between every 10 seconds or less and 5 minutes or more. In some embodiments, the pump assembly can be configured to monitor the duty cycle once per minute. This can be accomplished by maintaining a timer (in firmware, software, hardware or any combination thereof), which can be set to expire every minute (e.g., as is indicated by an interrupt or via polling) and can be restarted (e.g., by clearing an interrupt). In some embodiments, the time interval for measuring the duty cycle can be a preset value, set or changed by the user, and/or varied based on various operating conditions or on any combination thereof. In some embodiments, the pump assembly can be configured to monitor the duty cycle when the pump assembly is in the operational state category 1250 (i.e., any of states 1260, 1266, 1270, 1280, 1290, 1294 and/or any transitions between any of the states), as the pump assembly is configured to activate the pump in this state category. In some embodiments, the pump assembly can be configured to monitor the duty cycle when the pump assembly is in a particular state and/or state transition or subset of states and/or state transitions of the operational state category 1250. In some embodiments, the pump assembly can be configured to monitor the duty cycle when the pump assembly is in a particular state and/or state transition, subset of states and/or state transitions, or all states and/or state transitions of the active state category 1210 or any combination of any states and/or state transitions disclosed herein. As is illustrated in FIG. 26, the pump assembly can make the transition 1302 from any of states 1260, 1266, 1270, 1280, 1290, 1294 and/or transitions between any of the states to state 1300, where the pump assembly determines the duty cycle of the pump during the elapsed minute. The duty cycle can be determined according to the equation:

$$DC=t/T, \quad (2)$$

where DC is the duty cycle, t is the duration that the source of negative pressure is active, and T is the total time under consideration. In case of monitoring the duty cycle once per minute (i.e., T=60 seconds), the duty cycle can be expressed (e.g., in percent) as:

$$DC=(\text{Pump run time during the elapsed minute}/60) \\ *100\% \quad (3)$$

In order to determine the duty cycle, the pump assembly can be configured to monitor the duration of time that the pump has been active (e.g., the pump run time) and/or inactive.

In some embodiments, the pump assembly can be configured to compare the determined duty cycle to a duty cycle threshold, which can be selected from the range between 1% or less and 50% or more. The comparison can, for example, indicate presence of a leak in the system. In other words, if the pump is remains active over a period of time so that the duty cycle threshold is reached or exceeded, the pump may be working hard to overcome the leak. In such cases, the pump assembly can be configured to suspend or pause the delivery of therapy. The pump assembly can be configured to provide an indication to the user that the pump is working hard (e.g., duty cycle exceeds the duty cycle threshold) by, for example, deactivating the source of negative pressure. In some embodiments, the duty cycle threshold can be a preset value, set or changed by the user, and/or varied based on various operating conditions or on any combination thereof. As is illustrated in FIG. 26, the pump assembly can be configured to compare the determined duty cycle to the duty cycle threshold (e.g., 9%). The pump assembly can be configured to monitor the number of duty cycles that exceed the threshold by, for example, maintaining and updating an overload counter, which can be reset when the pump assembly transitions from state 1252 to the IPD state 1260.

In some embodiments, the pump assembly can be configured to update the overload counter in state 1300. If the determined duty cycle does not exceed the duty cycle threshold, the pump assembly can decrement the overload counter. In some embodiments, the minimum value of overload counter can be set to zero, that is the overload counter cannot become negative. Conversely, if the determined duty cycle is equal to or exceeds the duty cycle threshold, the pump assembly can increment the overload counter.

In some embodiments, the pump assembly can be configured to monitor a total or aggregate number of duty cycles that equal to or exceed the duty cycle threshold. This approach can help to smooth or average the duty cycle variation in order to, for example, prevent one or several erratic cycles that may be caused by a transient leak from interrupting therapy. In some embodiments, the pump assembly can be configured to monitor consecutive or non-consecutive duty cycles exceeding the duty cycle threshold. In some embodiments, the threshold can be a preset value, set or changed by the user, and/or varied based on various operating conditions or on any combination thereof. If the number of duty cycles that exceed the duty cycle threshold is determined to exceed an overload threshold (e.g., a number between 1 and 60 or more, such as 30), the pump assembly can be configured to make the transition 1230 to the paused state 1216, where therapy is suspended or paused as is described above. In some embodiments, the pump assembly can be configured to deactivate the source of negative pressure, which can provide an indication to the user that the pump is working hard (e.g., duty cycle exceeds the overload threshold). If the number of duty cycles that exceed the duty cycle threshold is not determined to exceed the overload threshold, the pump assembly can be configured to make the transition 1304 and remain in the operational state category 1250. In some embodiments, the pump assembly can be configured to return to the same state and/or transition between states from which the pump assembly made the transition 1302. In some embodiments, the pump assembly can be configured to transition to a different state and/or transition between states.

In some embodiments the pump assembly is further configured to suspend or pause therapy if the user presses the button 1002 while the pump assembly is in the operational state category 1250. In some embodiments, the pump assembly can be configured to transition to the manually paused state 1216.

Figure 27:
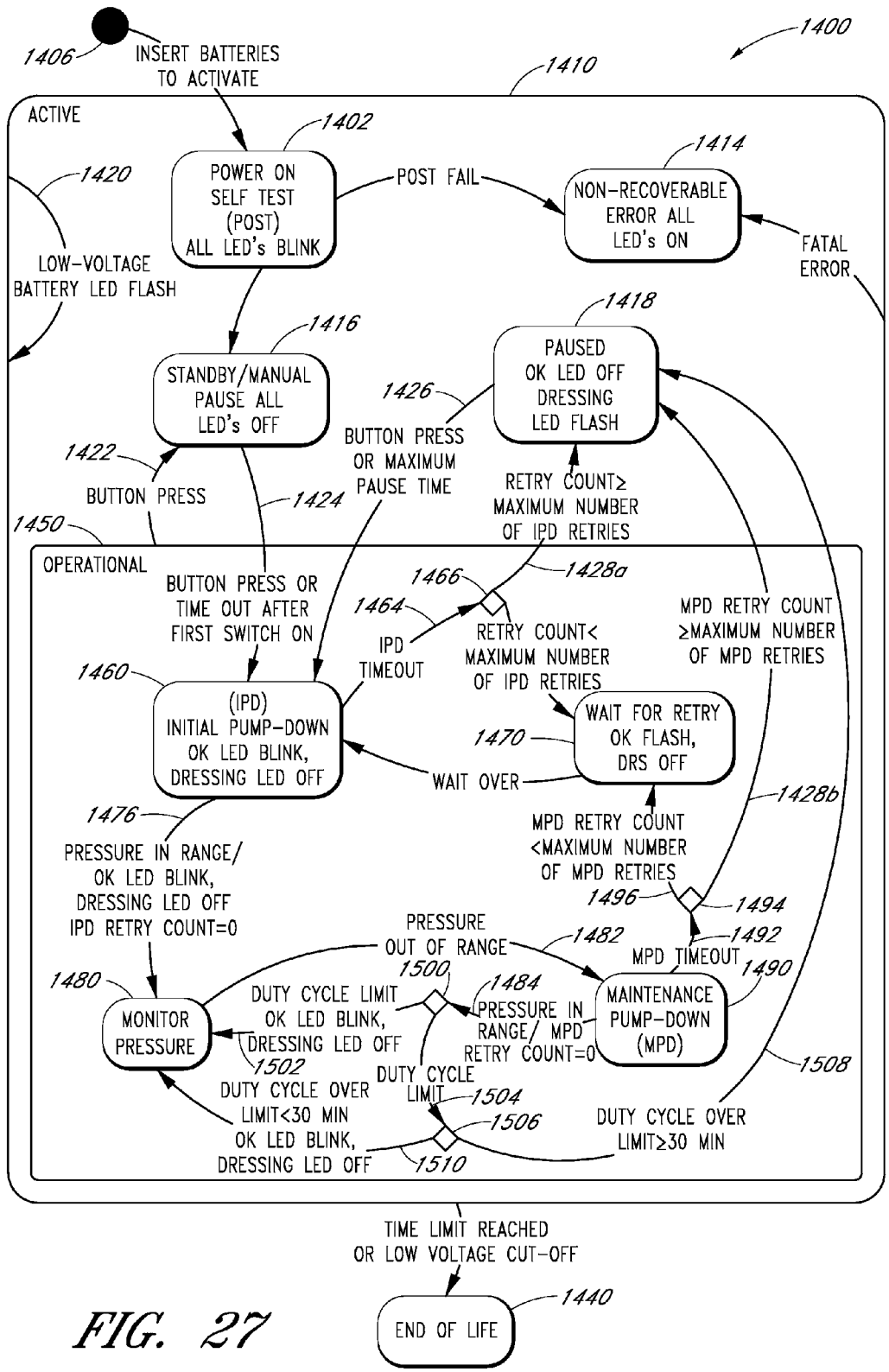
FIG. 27 illustrates another state diagram of operation of a pump assembly according to some embodiments.

FIG. 27 illustrates another state diagram of operation of the pump assembly 1000 according to some embodiments. In some embodiments, the controller 1140 can be configured to implement the flow of the state diagram 1400. In some embodiments, the flow 1400 can be largely similar to the flow illustrated in FIGS. 25-26. State 1402 corresponds to state 1202, state 1406 corresponds to state 1260, state category 1410 corresponds to state category 1210, state 1414 corresponds to state 1214, state 1416 corresponds to state 1216, state 1418 corresponds to state 1218, transition 1420 corresponds to transition 1220, transition 1422 corresponds to transition 1222, transition 1424 corresponds to the transition 1224, transition 1426 corresponds to transition 1226, and state 1440 corresponds to state 1240. In addition, state category 1450 corresponds to state category 1250, state 1460 corresponds to state 1260, transition 1464 corresponds to transition 1264, state 1466 corresponds to transition 1266, transition 1468 corresponds to transition 1268, transition 1428*a* corresponds to transition 1228*a*, state 1470 corresponds to state 1270, and transition 1472 corresponds to transition 1272. Further, transition 1476 corresponds to transition 1276, state 1480 corresponds to state 1280, transition 1482 corresponds to transition 1282, state 1490 corresponds to state 1290, transition 1492 corresponds to transition 1292, state 1494 corresponds to state 1294, transition 1496 corresponds to transition 1296, and transition 1428*b* corresponds to transition 1228*b*.

In some embodiments, the pump assembly can be configured to monitor the duty cycle after a desired negative pressure level is established under the dressing 1010 in the MPD state 1490. In some embodiments, the pump assembly can also take into account the duration of time that the pump has been active while the pump assembly remains in the IPD state 1460. As is illustrated, the device can be configured to make the transition 1484 from the MPD state 1490. Transition 1484 can be similar to the transition 1284, but instead of transitioning directly to the IPD state 1480, the pump assembly can be configured to monitor the duty cycle in state 1500. In some embodiments, the pump assembly can be configured to monitor the duty cycle during a cumulative period of time that the pump assembly has remained in the monitor state 1480 and MPD state 1490. In some embodiments, the pump assembly can be configured to monitor the duty cycle over the cumulative period of time during the immediately preceding or previous monitor and MPD cycles. For example, immediately before transitioning to state 1500 the pump assembly could have remained in the MPD state 1490 for time duration X (during which the pump was active). In addition, assuming that immediately before transitioning to the MPD state 1490, the pump assembly remained in the monitor state 1480 for a time duration Y (during which the pump was not active), the duty cycle (DC) can be expressed (e.g., in percent) as:

$$DC=100\%*[X/(X+Y)]. \quad (4)$$

In order to determine the duty cycle, the pump assembly can be configured to monitor the duration of time that the pump has been active and/or inactive.

In some embodiments, the pump assembly can be configured to compare the determined duty cycle to a duty cycle threshold (e.g., 9%), as is described above. In some embodiments, the threshold can be a preset value, set or changed by the user, and/or varied based on various operating conditions or on any combination thereof. If the duty cycle is determined to be below the threshold, the pump assembly can be configured to make the transition 1502 to the monitor state 1480. Conversely, if the duty cycle is determined to be equal to or exceed the threshold, the pump assembly can be configured to make the transition 1504 to state 1506. In some embodiments, the pump assembly can provide an indication that the duty cycle exceeds the threshold by, for example, deactivating the pump.

In some embodiments, the pump assembly can be configured to monitor a total or aggregate time over which the duty cycle is equal to or exceeds the threshold. This approach can help to smooth or average the duty cycle variation in order to, for example, prevent one or several erratic cycles that may be caused by a transient leak from interrupting therapy. Monitoring can be accomplished by maintaining a timer (in firmware, software, hardware or any combination thereof), which can be restarted (e.g., on the transition 1476) and updated (e.g., in state 1506). In some embodiments, the pump assembly can be configured to determine whether the duty cycle equals to or exceeds the threshold over a certain aggregate period of time, which can be compared to an aggregate duration threshold. The threshold can be selected from a range between 5 minutes or less and 2 hours or more, such as 30 minutes. In some embodiments, the threshold can be a preset value, set or changed by the user, and/or varied based on various operating conditions or on any combination thereof.

If the aggregate period of time equals to or exceeds the threshold, the pump assembly can be configured to make the transition 1508 to the paused state 1418, where the pump assembly can be configured to suspend or pause the delivery of therapy. In some embodiments, the pump assembly can indicate this transition to the user by, for example, deactivating the pump. Conversely, if the aggregate period of time is determined to be less than the threshold, the pump assembly can be configured to make the transition 1510 to the monitor state 1480. The pump assembly can be configured to indicate the transition 1510 to the user by, for example, causing the OK indicator 1062 to blink or flash and deactivating the dressing indicator 1064.

Figure 28:
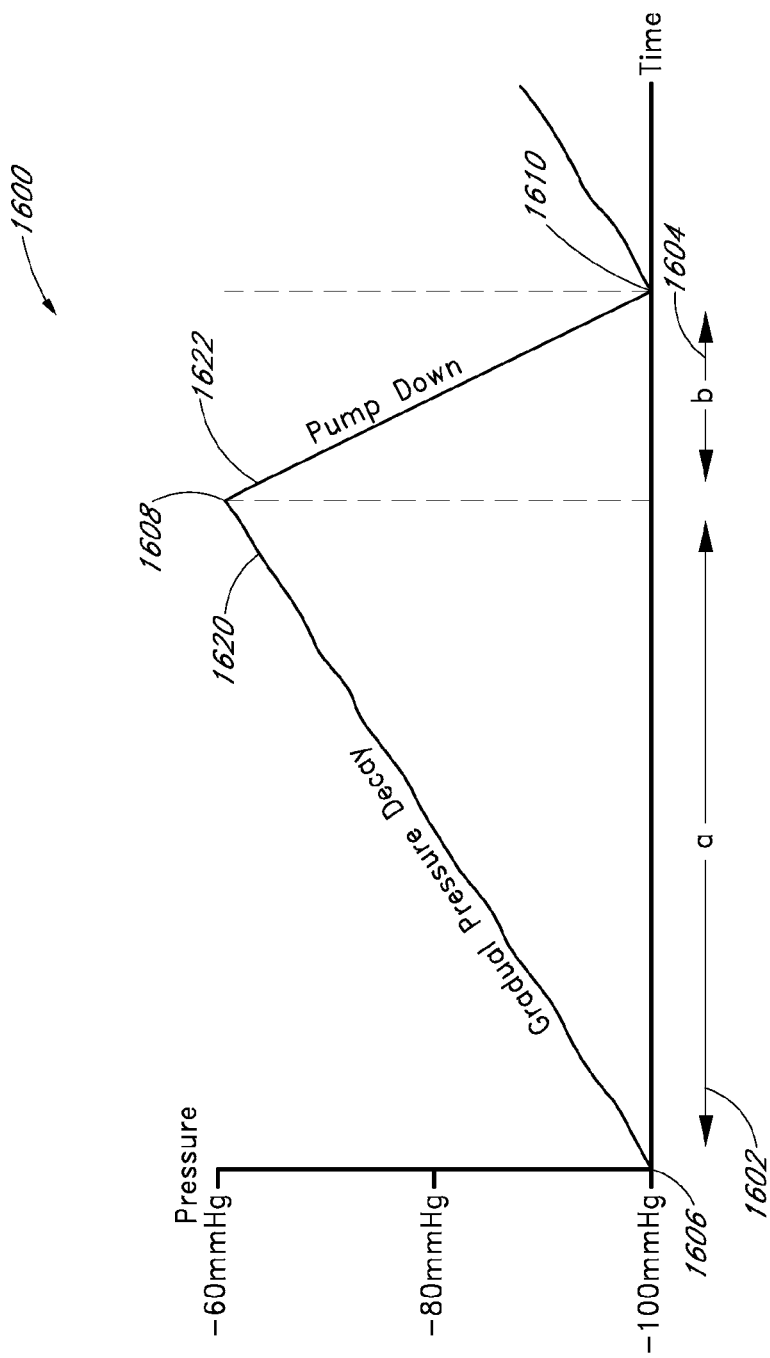
FIG. 28 illustrates a graph depicting a duty cycle determination for a pump assembly according to some embodiments.

FIG. 28 illustrates a graph 1600 depicting a duty cycle determination for the pump assembly 1000 according to some embodiments. The x-axis represents time and the y-axis represents pressure. In some embodiments, the pump assembly can be configured to establish a negative pressure level of −100 mmHg under the dressing 1010, as is represented by position 1606. For example, this can be performed during the initial pump down in state 1260. The pump assembly can be configured to monitor the level of negative pressure under the dressing 1010. For example, this can be performed in the monitor state 1280. As is illustrated, the pump assembly can monitor pressure over the period of time a, as represented by interval 1602. The level of negative pressure under the dressing 1010 can decay over time (e.g., due to leaks in the system), as is illustrated by line 1620.

In some embodiments, the pump assembly can be configured to restore or reestablish the negative pressure level under the dressing 1010 when that pressure decays to reach or pass a threshold of approximately −70 mmHg, as is represented by position 1608. In some embodiments, the pump assembly can be configured to activate the pump, as is illustrated by line 1622. For example, this can be performed by transitioning to the maintenance pump down state 1290. As is illustrated, the pump assembly can activate the pump for a time duration b (1604) until the negative pressure level of −100 mmHg is reestablished under the dressing 1010. The pump assembly can be configured to deactivate the pump when the level of pressure under the dressing 1010 reaches −100 mmHg at position 1610. For example, this can be performed by transition to the monitor state 1280. The duty cycle (DC) over the period illustrated in 1600 (i.e., a+b) can be expressed (e.g., in percent) as:

$$DC = 100\% * [b/(a+b)]. \quad (5)$$

Figure 29:
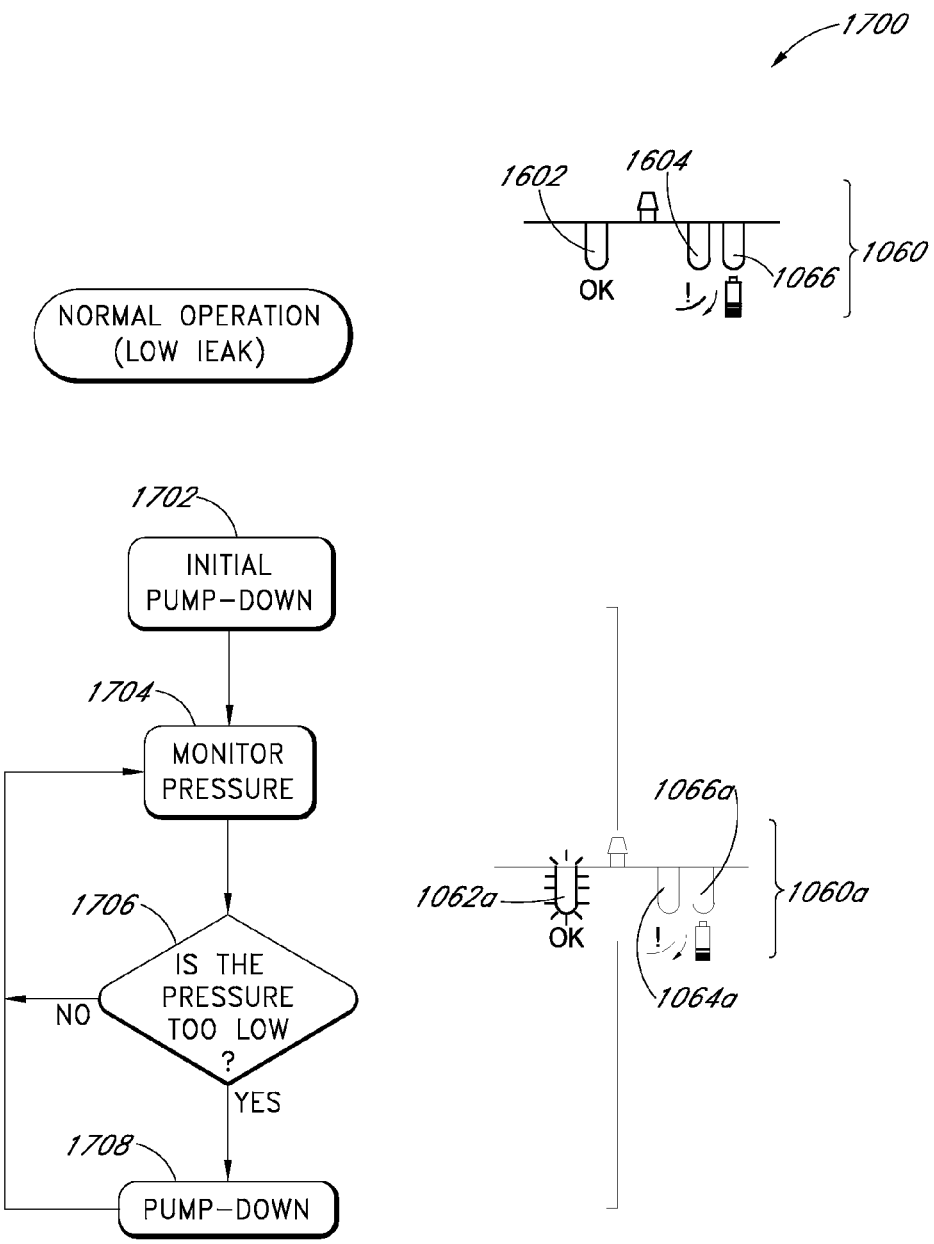
FIG. 29 illustrates operation of a pump assembly in presence of a low leak according to some embodiments.

FIG. 29 illustrates a non-limiting example of a normal (e.g., no leak or low leak) operation 1700 of some embodiments of the pump assembly 1000. The pump assembly can be configured to establish a desired level of negative pressure under the dressing 1010, as is illustrated in box 1702. The pump assembly can be configured such that, if the level of pressure under the dressing 1010 rises above a desired level (e.g., first set point value, such as −70 mmHg), the source of negative pressure (e.g., a pump) will be activated and will start operating to reduce the level of pressure under the dressing 1010 to the desired value. For example, the desired value can be approximately within the interval between the first and second set point value or approximately the second set point value (e.g., −100 mmHg). In some embodiments, this can be accomplished in the initial pump down state 1260.

In some embodiments, when the level of pressure under the dressing 1010 reaches the desired value, the pump assembly can be configured to deactivate the pump and monitor the level of pressure under the dressing, as is illustrated in box 1704. For example, this can be accomplished in the monitor state 1280. The pump assembly can be configured to periodically or continuously monitor the level of pressure under the dressing 1010 by, for example, reading or sampling the sensor 1070. Based on the monitored pressure, the pump assembly can determine in box 1706 whether the pump needs to be activated or restarted to reestablish the desired level of negative pressure under the dressing 1010. If the monitored pressure is determined to be low (e.g., less than or less than or equal to the first set point value), the pump assembly can be configured to activate the pump, as is illustrated in box 1708. For example, this can be accomplished by transitioning to the MPD state 1290. Conversely, if the monitored level of pressure is not determined to be low (e.g., greater than or greater than or equal to the first set point value), the pump assembly can be configured to continue monitoring the level of pressure under the dressing 1010. During this operational flow, the pump assembly can be configured to indicate to the user that it is operating normally. As is illustrated in 1060a, the pump assembly can activate or cause to blink or flash the OK indicator 1062, which is depicted as 1062a. In addition, the pump assembly can deactivate the dressing indicator 1064 and the battery indicator 1066, which are depicted as 1064a and 1066a respectively.

Figure 30:
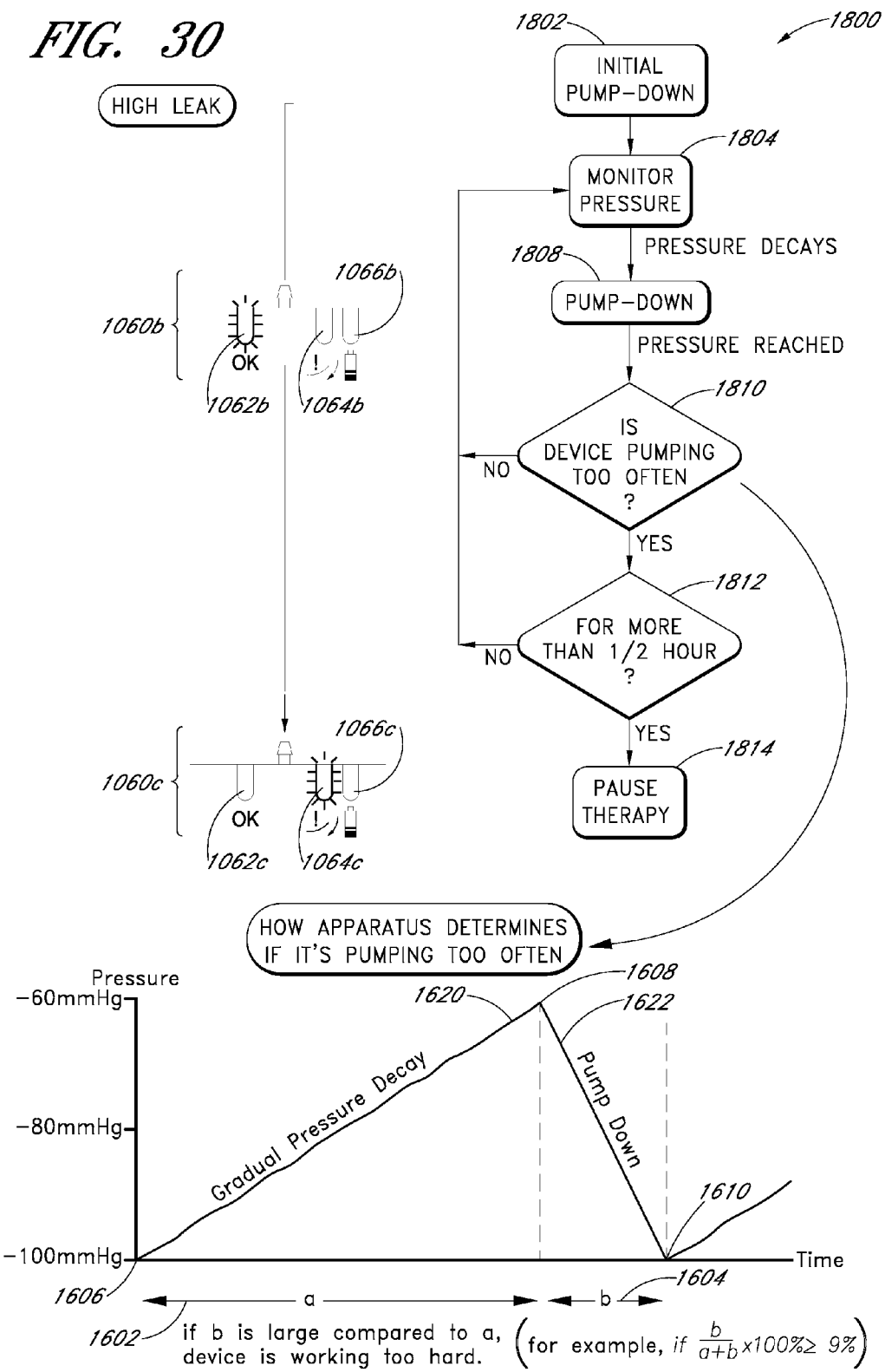
FIG. 30 illustrates operation of a pump assembly in presence of a high leak according to some embodiments.

FIG. 30 illustrates a non-limiting example of operation 1800 of some embodiments of the pump assembly 1000 in presence of a high leak. As is described above in connection with FIG. 29, the pump assembly can be configured to establish a desired level of negative pressure under the dressing 1010, as is illustrated in box 1802. In some embodiments, when the level of pressure under the dressing 1010 reaches the desired value, the pump assembly can be configured to deactivate the pump and monitor the level of pressure under the dressing, as is illustrated in box 1804. The pump assembly can be configured to periodically or continuously monitor the level of pressure under the dressing 1010 by, for example, reading or sampling the sensor 1070. Based on the monitored level of pressure, the pump assembly can determine whether the pump needs to be activated or restarted to reestablish the desired level of negative pressure under the dressing 1010. If the monitored level of pressure is determined to be low (e.g., less than or less than or equal to the first set point value), the pump assembly can be configured to activate the pump, as is illustrated in box 1808. Once the desired level of pressure has been reestablished under the dressing 1010, the pump assembly can recommence monitoring the level of negative pressure under the dressing (e.g., transition to the monitor state 1280).

In some embodiments, due to presence of a leak or leaks in the system, the pump assembly 1010 can be configured to carry out multiple cycles of monitoring and reactivating the pump. During this operational flow, the pump assembly can be configured to indicate to the user that the pump assembly is operating normally. As is illustrated in 1060b, the pump assembly can activate or cause to blink or flash the OK indicator 1062, which is depicted as 1062b. In addition, the pump assembly can deactivate the dressing indicator 1064 and the battery indicator 1066, which are depicted as 1064b and 1066b respectively. The pump assembly can be configured to continuously or periodically determine whether the pump is pumping too often, as is illustrated in box 1810. As is illustrated, in some embodiments, the pump assembly can be configured to use the duty cycle as a proxy for determining whether the pump is pumping too often. For example, the pump assembly can be configured to determine whether the pump is "working hard," that is determine whether the pump is on for more than a threshold duration, such as 9% of the total therapy time. In other words, the pump assembly can be configured to determine whether the duty cycle of the pump reaches or exceeds the duty cycle threshold.

In some embodiments, the pump assembly can be configured to suspend or pause operation of the pump if the pump is determined to be working hard over a duration of time (e.g., the pump is on for more than about 2 hours a day, or is on for more than a predetermined amount of time), even if the desired level of negative pressure (e.g., second set point value) has been established. As is illustrated in box 1812, the pump assembly can be configured to determine whether the pump is working hard for a duration of 30 minutes or more. For example, the pump assembly can be configured to determine whether duty cycle (or cycles) monitored over the past 30 minutes exceed the duty cycle threshold. For example, the pump assembly can determine whether the pump has been on for about 2 minutes and 42 seconds or longer over the last 30 minutes, which corresponds to 9% duty cycle threshold.

In some embodiments, the pump assembly can be configured to pause or suspend therapy if the pump is determined to be working hard, as is illustrated in box 1814. The pump assembly can be further configured to turn a "Leak alarm" indicator on. As is illustrated in 1060c, the pump assembly can activate or cause to blink or flash the dressing indicator 1064, which is depicted as 1064b, and deactivate the OK indicator 1062 and the battery indicator 1066, which are depicted as 1062c and 1066c respectively. To restart the therapy, the user may need to straighten the dressing, to fix the leak, and/or to activate the pump once again. In some embodiments, the pump can be activated again by pressing the start or operating button on the pump, because of a timeout, etc.

In the case of a leak or leaks being present in the dressing, in some embodiments, the pump assembly 1000 can be programmed or otherwise configured to suspend or pause therapy if the second set point value is not reached after a predetermined amount of operating time of the pump. For example, in some embodiments, if the pump has been running continuously for X minutes and the second set point pressure value has not been reached, the pump assembly can activate an alarm which can comprise an LED indicator, a "leak detected" LED indicator 1064, or other alarm, and pause the therapy. In some embodiments, the predetermined amount of time can be approximately 5% of the total planned duration of the negative pressure therapy for the system, or from approximately 3% or less to approximately 15% or more of the total planned duration of the negative pressure therapy for the system. In some embodiments, the predetermined amount of time can be approximately 9 minutes, or from approximately 4 minutes or less to approximately 40 minutes or more, or from approximately 6 minutes to approximately 10 minutes.

Figure 31:
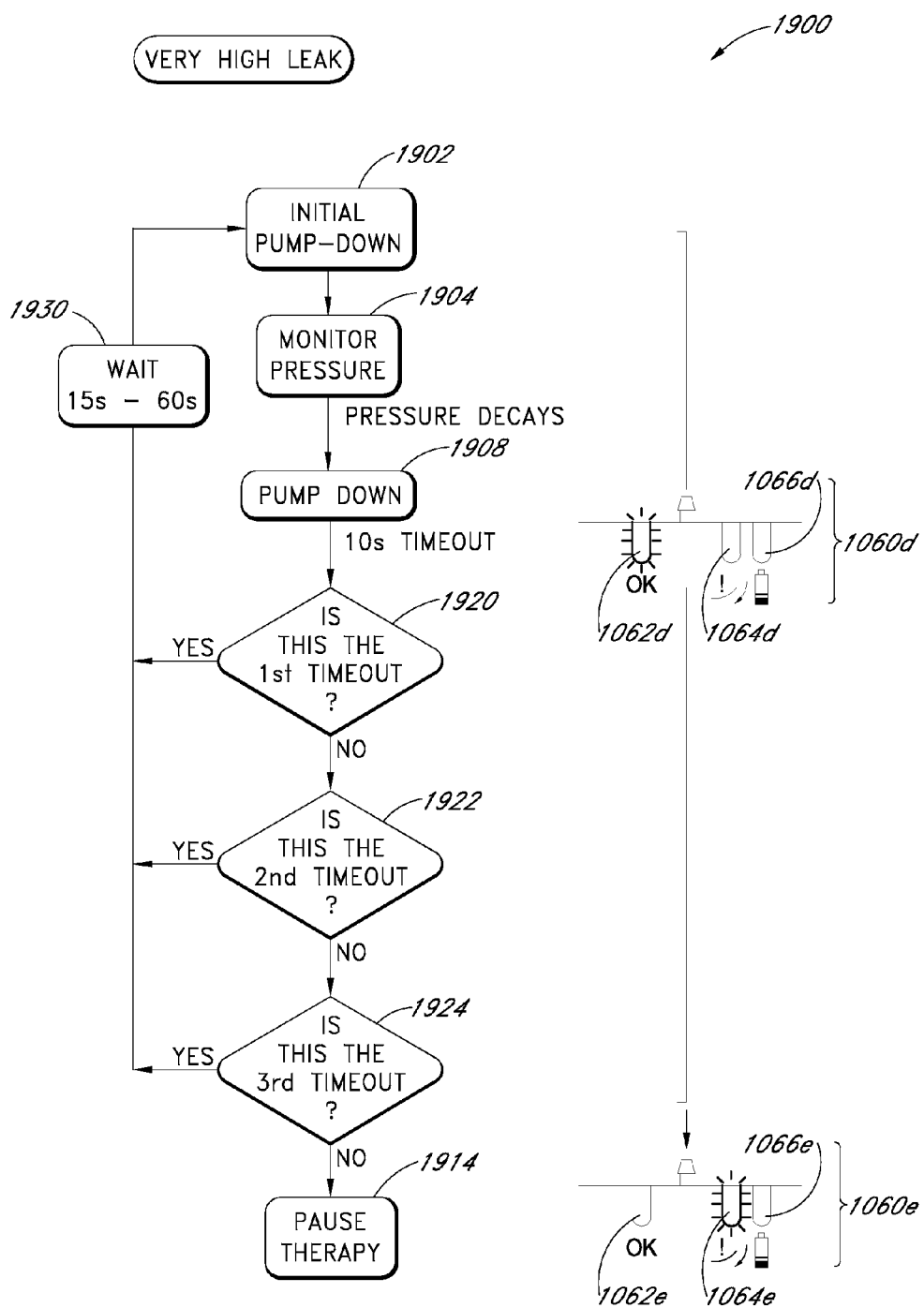
FIG. 31 illustrates operation of a pump assembly in presence of a very high leak according to some embodiments.

FIG. 31 illustrates a non-limiting example of operation 1900 of some embodiments of the pump assembly 1000 in presence of a very high leak. As is described above in connection with FIG. 29, the pump assembly can be configured to establish a desired level of negative pressure under the dressing 1010, as is illustrated in box 1902. In some embodiments, when the level of pressure under the dressing 1010 reaches the desired value, the pump assembly can be configured to deactivate the pump and monitor the level of pressure under the dressing, as is illustrated in box 1904. The pump assembly can be configured to periodically or continuously monitor the level of pressure under the dressing 1010 by, for example, reading or sampling the sensor 1070. Based on the monitored level of pressure, the pump assembly can determine whether the pump needs to be activated or restarted to reestablish the desired level of negative pressure under the dressing 1010. If the monitored level of pressure is determined to be low (e.g., less than or less than or equal to the first set point value), the pump assembly can be configured to activate the pump, as is illustrated in box 1908. During this operational flow, the pump assembly can be configured to indicate to the user that the pump assembly is operating normally. As is illustrated in 1060d, the pump assembly can activate or cause to blink or flash the OK indicator 1062, which is depicted as 1062d. In addition, the pump assembly can deactivate the dressing indicator 1064 and the battery indicator 1066, which are depicted as 1064d and 1066d respectively.

In some embodiments, due to a leak or leaks (e.g., a leak that has a relatively very high flow rate), the pump assembly may not be able to reach a desired negative pressure level and/or the second set point value under the dressing 1010. If after a predetermined amount of operating time, the desired negative pressure level is not reached under the dressing, the pump assembly can be configured to suspend or pause the pump, as is illustrated in box 1914. For example, this can be accomplished by transitioning to the wait state 1270. In some embodiments, the predetermined amount of pump operating time can be 10 seconds (as is illustrated in FIG. 31). In some embodiments, the predetermined amount of pump operating time can be from approximately 5 seconds or less to approximately 60 seconds or more.

In some embodiments, the pump assembly can be configured to provide a limited number of retry cycles before pausing or suspending therapy. As illustrated in boxes 1920, 1922, and 1924, the pump assembly can be configured to go through three retry cycles before suspending or pausing therapy (1914) and/or activating an alarm, such as the "Leak alarm." Some embodiments of the pump assembly can go through two retry cycles, four retry cycles, etc. before pausing therapy and/or activating an alarm. As is illustrated in 1060e, the pump assembly can activate or cause to blink or flash the dressing indicator 1064, which is depicted as 1064e, and deactivate the OK indicator 1062 and the battery indicator 1066, which are depicted as 1062e and 1066e respectively.

Figure 32:
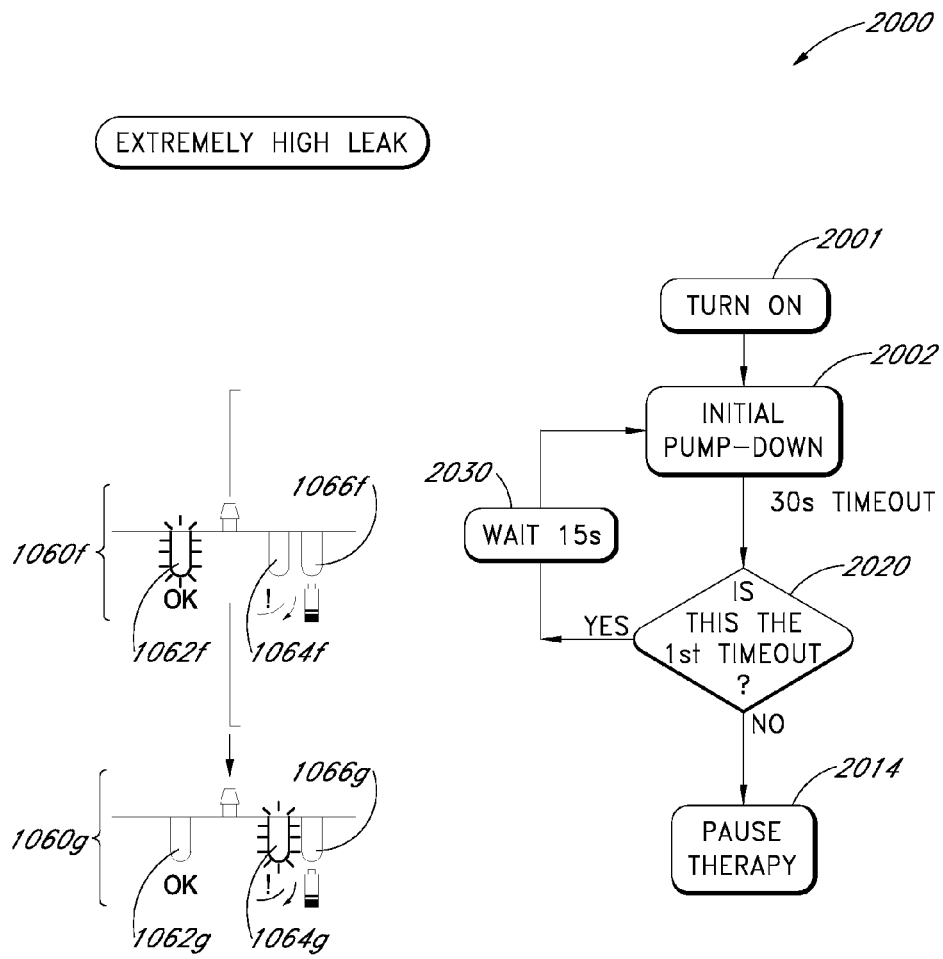
FIG. 32 illustrates operation of a pump assembly in presence of an extremely high leak according to some embodiments.

FIG. 32 illustrates a non-limiting example of operation 2000 of some embodiments of the pump assembly 1000 in presence of an extremely high leak. The pump assembly can be configured to quickly go into a therapy pause or suspend mode to avoid wasting the batteries trying to cope with a high flow rate leak. As is illustrated in box 2001, the pump assembly can be turned on, which can be accomplished, for example, by transitioning into the operational state category 1250. As is described above in connection with FIG. 29, the pump assembly can be configured to establish a desired level of negative pressure under the dressing 1010, as is illustrated in box 2002.

In some embodiments, if the leak is extremely high, such as when the pump is turned on but not yet connected to the dressing or not properly connected to the dressing, the pump assembly can be configured to operate for a predetermined amount of time while attempting to draw the pressure under the dressing 1010 to a desired negative pressure level. (e.g., approximately the second set point value or a value within the interval between the first and second set point values). The pump assembly can be configured to suspend or pause therapy upon expiration of the predetermined amount of time. For example, this can be accomplished by transitioning to the wait state 1270. As is illustrated, the pump assembly can be configured to operate the pump for 30 seconds. If during this period of time the pressure under the dressing 1010 has not been drawn to the desired negative pressure, the pump assembly can go into a timeout mode 2020 for another predetermined amount of time (e.g., for 15 seconds, as illustrated in FIG. 32). During this operational flow, the pump assembly can be configured to indicate to the user that the pump assembly is operating normally. As is illustrated in 1060*f*, the pump assembly can activate or cause to blink or flash the OK indicator 1062, which is depicted as 1062*f*. In addition, the pump assembly can deactivate the dressing indicator 1064 and the battery indicator 1066, which are depicted as 1064*f* and 1066*f* respectively.

In some embodiments, the pump assembly can be configured to provide a limited number of retry cycles for establishing the desired level of negative pressure under the dressing 1010. As is illustrated, after the first trial (or any number of additional trials), the pump assembly can be configured to establish or reestablish the desired negative pressure level under the dressing, as is illustrated in box 2002. In some embodiments, as is illustrated in box 2014, if the pump assembly operates for another predetermined amount of time without drawing the pressure under the dressing 1010 to the desired level (e.g., approximately the second set point value or to a value within the interval between the first and second set point values) after a first attempt, the pump assembly can be configured to suspend or pause therapy without retrying the pump down. The pump assembly can be configured to remain in the suspended or paused state until the pump assembly is reactivated (e.g., due to a timeout, due to the user pressing the button, etc.) The pump assembly can be configured to activate an alarm in this state. During this operational flow, the pump assembly can be configured to indicate to the user that a leak or leaks are present. As is illustrated in 1060*g*, the pump assembly can activate or cause to blink or flash the dressing indicator 1064, which is depicted as 1064*g*, and deactivate the OK indicator 1062 and the battery indicator 1066, which are depicted as 1062*g* and 1066*g* respectively.

Throughout the description and claims of this specification, the words "comprise" and "contain" and variations of the words, for example "comprising" and "comprises", mean "including but not limited to", and is they are not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise. Further, in some embodiments, the term approximately is meant to refer to values within 10% of the stated values, unless otherwise stated herein.

Any value of a threshold, limit, duration, timeout, retry count, etc. provided herein is not intended to be absolute and, thereby, can be approximate. In addition, any threshold, limit, duration, timeout, retry count, etc. provided herein can be fixed or varied either automatically or by the user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value.

Features, integers, characteristics, compounds, chemical moieties or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Accordingly, the scope of the present disclosure is intended to be defined only by reference to the appended claims. The accompanying claims and their equivalents are intended to cover such forms or modifications as would fall within the scope and spirit of the protection. For example, the various components illustrated in the figures may be implemented as software and/or firmware on a processor, controller, ASIC, FPGA, and/or dedicated hardware. Furthermore, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. An apparatus for applying negative pressure to a wound, comprising:
    a dressing configured to be placed over a wound and to create a substantially fluid impermeable seal over the wound;
    a negative pressure pump disposed in a housing, the pump configured to be coupled to the dressing placed over the wound;
    an interface positioned on an outer surface of the housing, the interface configured to cause the pump to operate and configured to cause the pump to pause operation for a period of time; and
    a controller coupled to the interface, the controller configured to:
        activate the pump in response to a first signal from the interface causing the pump to operate;
        monitor a duty cycle of the pump, compare the monitored duty cycle of the pump to a duty cycle threshold, and pause operation of the pump for the period of time in response to determining that the duty cycle of the pump exceeds the duty cycle threshold as a result of one or more leaks in the seal over the wound;
        pause operation of the pump in response to a second signal from the interface causing the pump to pause operation for the period of time;
        restart the pump upon expiration of the period of time; and
        reset the monitored duty cycle of the pump in response to pausing or restarting the pump.

2. The apparatus of claim 1, wherein the period of time is variable.

3. The apparatus of claim 1, wherein the pump comprises a miniature pump.

4. The apparatus of claim 1, wherein the pump comprises one of: a miniature diaphragm pump operated by a motor and a miniature diaphragm pump operated by a piezoelectric transducer.

5. The apparatus of claim 1, wherein the pump comprises one of: a miniature piston pump and a miniature diaphragm pump.

6. The apparatus of claim 1, further comprising an indicator configured to provide a first indication when the pump is running and a second indication when the pump is paused, wherein the second indication is different from the first indication.

7. The apparatus of claim 6, wherein the indication comprises at least one of: a visual indication and an audible indication.

8. The apparatus of claim 1, wherein the controller is further configured to:
monitor the duty cycle of the pump over a duration of time, update an aggregate duty cycle of the pump over a plurality of durations of time in response to the comparison of the monitored duty cycle of the pump to the duty cycle threshold, and pause operation of the pump for the period of time in response to determining that the aggregate duty cycle of the pump exceeds an aggregate duty cycle threshold; and
reset the aggregate duty cycle of the pump in response to pausing or restarting the pump.

9. The apparatus of claim 8, wherein the aggregate duty cycle of the pump comprises a counter, and the controller is further configured to:
increment the counter when the monitored duty cycle exceeds the duty cycle threshold; and
decrement the counter when the monitored duty cycle measurement does not exceed the duty cycle threshold.

10. The apparatus of claim 9, wherein the controller is further configured to:
compare the counter with the aggregate duty cycle threshold at the end of each duration of time.

11. A method of operating a negative pressure pump, comprising:
in response to receiving a first signal from an interface of the pump, activating the pump to deliver negative pressure to a dressing positioned over a wound;
monitoring a duty cycle of the pump, comparing the monitored duty cycle to a duty cycle threshold, and pausing the pump for the period of time in response to determining that the duty cycle of the pump exceeds the duty cycle threshold as a result of one or more leaks in a seal over the wound;
restarting the pump upon expiration of the period of time; and
resetting the monitored duty cycle of the pump in response to pausing or restarting the pump.

12. The method of claim 11, wherein the period of time is variable.

13. The method of claim 11, wherein the pump comprises a miniature pump.

14. The method of claim 11, further comprising providing a first indication when the pump is running and providing a second indication when the pump is paused, wherein the second indication is different from the first indication.

15. The method of claim 14, wherein the indication comprises at least one of: a visual indication and an audible indication.

16. The method of claim 11, further comprising:
monitoring the duty cycle of the pump over a duration of time, updating an aggregate duty cycle of the pump over a plurality of durations of time in response to the comparison of the monitored duty cycle of the pump to the duty cycle threshold, and pausing operation of the pump for the period of time in response to determining that the aggregate duty cycle of the pump exceeds an aggregate duty cycle threshold; and
resetting the aggregate duty cycle of the pump in response to pausing or restarting the pump.

17. The method of claim 16, wherein the aggregate duty cycle of the pump comprises a counter, the method further comprising:
incrementing the counter when the monitored duty cycle measurement the duty cycle threshold; and
decrementing the counter when the monitored duty cycle measurement does not exceed the duty cycle threshold.

18. The method of claim 17, further comprising:
comparing the counter with the aggregate duty cycle threshold at the end of each duration of time.

19. The method of claim 11, further comprising pausing the pump for a period of time in response to receiving a second signal from the interface.

20. The method of claim 12, further comprising determining a remaining capacity of a power source of the pump, and varying the period of time based at least in part on the remaining capacity of the power source.

21. The apparatus of claim 2, further comprising a power source, wherein the controller is further configured to determine a remaining capacity of the power source, and vary the period of time based at least in part on the remaining capacity of the power source.

* * * * *

UNITED STATES PATENT AND TRADEMARK OFFICE
CERTIFICATE OF CORRECTION

| | | |
|---|---|---|
| PATENT NO. | : 8,951,235 B2 | Page 1 of 1 |
| APPLICATION NO. | : 13/403715 | |
| DATED | : February 10, 2015 | |
| INVENTOR(S) | : Julie Allen | |

It is certified that error appears in the above-identified patent and that said Letters Patent is hereby corrected as shown below:

Title page (item 63, Related U.S. Application Data) at line 2, Change "and" to --which is--.

Drawings

Sheet 46 of 55 (Reference Numeral 1090, FIG. 23) at line 1, Change "DIAPHRAM" to --DIAPHRAGM--.

Specification

In column 1 at line 12, Change "PCT/GB 2011/051745," to --PCT/GB2011/051745,--.

In column 4 at lines 19-20, Change "durations" to --durations.--.

In column 7 at line 16 (approx.), Change "that" to --than--.

In column 10 at line 59, Change "X %)," to --X%),--.

In column 16 at line 38, Change "mBar A" to --mBarA--.

In column 19 at line 29, Change "and or" to --and/or--.

In column 23 at line 15, Change "chlorohexadine," to --chlorhexidine,--.

In column 23 at line 16, Change "hypochloride," to --hypochlorite,--.

In column 23 at line 30, Change "cyclodextrine," to --cyclodextrin,--.

In column 25 at line 3, Change "11 C" to --11C--.

In column 27 at line 41, Change "cyclodextrine," to --cyclodextrin,--.

In column 35 at line 36, Change "assembly'" to --assembly--.

Claims

In column 50 at line 33 (approx.), In Claim 17, change "measurement" to --measurement exceeds--.

Signed and Sealed this
Tenth Day of November, 2015

Michelle K. Lee
*Director of the United States Patent and Trademark Office*